US010941423B2

(12) United States Patent
Anissimova et al.

(10) Patent No.: US 10,941,423 B2
(45) Date of Patent: Mar. 9, 2021

(54) METHOD FOR THE PRODUCTION OF ISOAMYL ALCOHOL

(71) Applicant: Global Bioenergies, Evry (FR)

(72) Inventors: Maria Anissimova, Nozay (FR); Mathieu Allard, Saint-Vrain (FR)

(73) Assignee: Global Bioenergies, Evry (FR)

( * ) Notice: Subject to any disclaimer, the term of this patent is extended or adjusted under 35 U.S.C. 154(b) by 295 days.

(21) Appl. No.: 15/739,311

(22) PCT Filed: Jun. 23, 2016

(86) PCT No.: PCT/EP2016/064504
§ 371 (c)(1),
(2) Date: Dec. 22, 2017

(87) PCT Pub. No.: WO2016/207267
PCT Pub. Date: Dec. 29, 2016

(65) Prior Publication Data
US 2020/0010858 A1    Jan. 9, 2020

(30) Foreign Application Priority Data
Jun. 26, 2015    (EP) .................................. 15174104

(51) Int. Cl.
*C12P 7/16*        (2006.01)
*C12N 9/04*        (2006.01)
*C12N 9/02*        (2006.01)
*C12N 9/10*        (2006.01)
*C12P 7/24*        (2006.01)
*C12P 7/62*        (2006.01)

(52) U.S. Cl.
CPC .............. *C12P 7/16* (2013.01); *C12N 9/001* (2013.01); *C12N 9/0006* (2013.01); *C12N 9/0008* (2013.01); *C12N 9/1029* (2013.01); *C12P 7/24* (2013.01); *C12P 7/62* (2013.01); *C12Y 101/0108* (2013.01); *C12Y 102/01084* (2015.07); *C12Y 203/01084* (2013.01)

(58) Field of Classification Search
None
See application file for complete search history.

(56) References Cited

U.S. PATENT DOCUMENTS 7,985,565 B2 *    7/2011    Mayer .................. C12Q 1/6834
                                                 435/91.2
2014/0256008 A1    9/2014    Boisart et al.

FOREIGN PATENT DOCUMENTS

WO    2013150100        10/2013
WO    2016042011         3/2016
WO    2016207267 A1    12/2016

OTHER PUBLICATIONS

Rodriguez et al. Expanding ester biosynthesis in *Escherichia coli*. Nat Chem Biol 2014; 10(4): 259-265.*
International Preliminary Report on Patentability received in PCT/EP2016/064504 dated Jan. 4, 2018.
Afzal, et. al., "Identification of Metabolic Pathways Involved in the Biosynthesis of Flavor Compound 3-Methylbutanal From Leuicine Catabolism by Carnobacterium Maltaromaticum LMA 28", International Journal of Food Microbiology, vol. 157, 2012, pp. 332-339 (XP028426512).
Avalos, et. al., "Compartmentalization of Metabolic Pathways in Yeast Mitochondria Improves the Production of Branched-Chain Alcohols", Nature Biotechnology, vol. 31, No. 4, Apr. 2013, pp. 335-341 (XP002760980).
Boumba, et. al., "Biochemical Pathways Generating Post-Mortem Volatile Compounds Co-Detected During Forensic Ethanol Analyses", Forensic Science International, vol. 174, 2008, pp. 133-151 (XP022413303).
Dickinson, el. al., "A 13C Nuclear Magnetic Resonance Investigation of the Metabolism of Leucine to Isoamyl Alcohol in *Saccharomyces* Cerevisiae", The Journal of Biological Chemistry, vol. 272, Jun. 17, 1997, pp. 26871-26878 (XP008112497).
International Search Report and Written Opinion received in PCT/EP2016/064504 dated Sep. 2, 2017.
Li, et. al., "An Alternative Isovaleryl CoA Biosynthetic Pathway Involving a Previously Unknown 3-Methylglutaconyl CoA Decarboxylase", Angewandte Chemie International Edition, vol. 52, 2013, pp. 1304-1308 (XP002744276).
Liu, et. al., "Combining Chemoinformatics With Bioinformatics: In Silico Prediction of Bacterial Flavor-Forming Pathways by a Chemical Systems Biology Approach Reverse Pathway Engineering", PLOS One, vol. 9, No. 1., Jan. 2014, pp. 1-11 (XP002744274).

(Continued)

*Primary Examiner* — Iqbal H Chowdhury
(74) *Attorney, Agent, or Firm* — Michele M. Wales; Inhouse Patent Counsel, LLC

(57) ABSTRACT

Described is a method for the production isoamyl alcohol (3-methylbutan-1-ol) comprising the enzymatic conversion of 3-methylbutyryl-CoA (isovaleryl-CoA) into isoamyl alcohol comprising: (a) two enzymatic steps comprising (i) first the enzymatic conversion of 3-methylbutyryl-CoA into 3-methylbutyraldehyde (3-methylbutanal or isovaleraldehyde); and (ii) then enzymatically converting the thus obtained 3-methylbutyraldehyde into said isoamyl alcohol; or (b) a single enzymatic reaction in which 3-methylbutyryl-CoA is directly converted into isoamyl alcohol by making use of an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84). Further, described is the above method wherein the 3-methylbutyryl-CoA can be provided by the enzymatic conversion of 3-methylcrotonyl-CoA into said 3-methylbutyryl-CoA. It is also described that the thus obtained isoamyl alcohol can be further enzymatically converted into 3-methylbutyl acetate (isoamyl acetate) as described herein. Described are also recombinant organisms or microorganisms which are capable of performing the above enzymatic conversions. Furthermore, described are uses of enzymes and enzyme combinations which allow the above enzymatic conversions.

Figure 1:
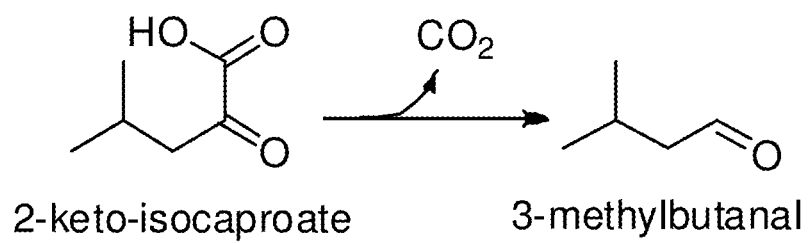

33 Claims, 7 Drawing Sheets
Specification includes a Sequence Listing.

(56) References Cited

OTHER PUBLICATIONS

Rodriguez, et. al., "Expanding Ester Biosynthesis in *Escherichia coli*", Nature Chemical Biology, vol. 10, No. 4, Apr. 2014, pp. 259-265 (XP002744275).
Office communication 94(3) from the EPO dated Oct. 15, 2018.
Straathof et al., "Transformation of Biomass into Commodity Chemicals Using Enzymes or Cells", Chemical Reviews, vol. 114, pp. 1871-1908, (2014).

* cited by examiner

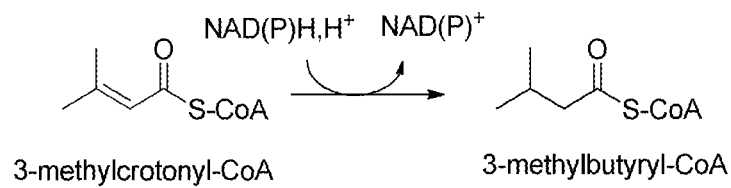
3-methylcrotonyl-CoA → 3-methylbutyryl-CoA
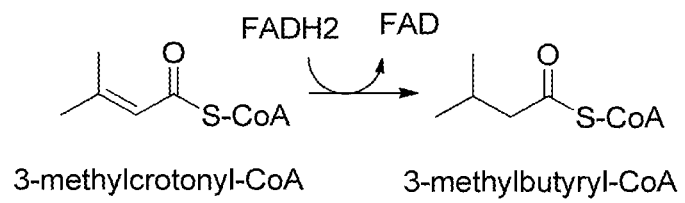
3-methylcrotonyl-CoA → 3-methylbutyryl-CoA
Figures 7a and b
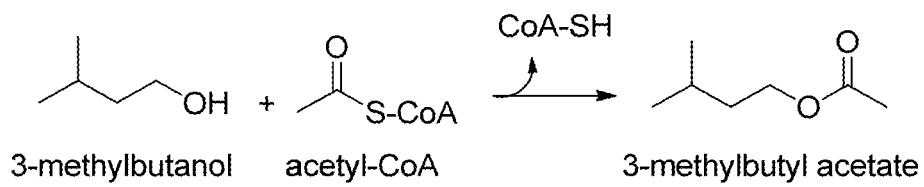
3-methylbutanol + acetyl-CoA → 3-methylbutyl acetate
Figure 8
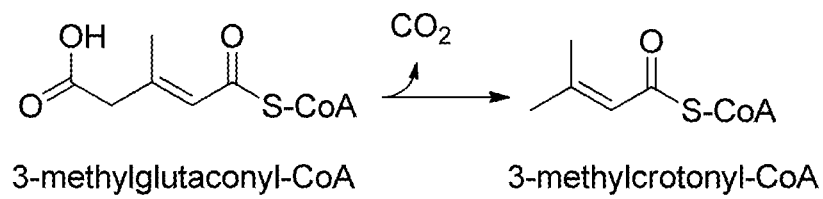
3-methylglutaconyl-CoA → 3-methylcrotonyl-CoA
Figure 9
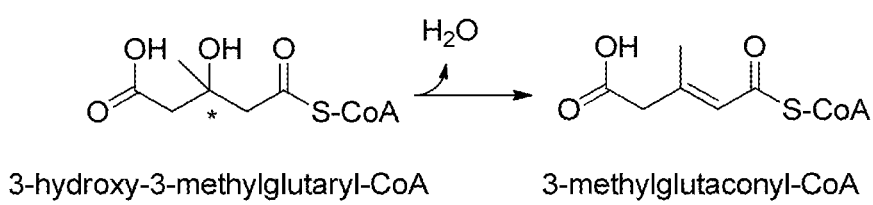
3-hydroxy-3-methylglutaryl-CoA → 3-methylglutaconyl-CoA
Figure 10

SEQUENCE LISTING

<160> NUMBER OF SEQ ID NOS: 13

<210> SEQ ID NO 1
<211> LENGTH: 661
<212> TYPE: PRT
<213> ORGANISM: Marinobacter hydrocarbonoclasticus
<220> FEATURE:
<223> OTHER INFORMATION: strain ATCC 700491 / DSM 11845 / VT8

<400> SEQUENCE: 1

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

-continued

Lys Val Val Arg Glu Glu Cys Lys Val Pro Phe Arg Ile Tyr Arg Pro
            165                 170                 175
Gly Met Val Ile Gly His Ser Glu Thr Gly Glu Met Asp Lys Val Asp
            180                 185                 190
Gly Pro Tyr Tyr Phe Phe Lys Met Ile Gln Lys Ile Arg His Ala Leu
            195                 200                 205
Pro Gln Trp Val Pro Thr Ile Gly Ile Glu Gly Gly Arg Leu Asn Ile
    210                 215                 220
Val Pro Val Asp Phe Val Asp Ala Leu Asp His Ile Ala His Leu
225                 230                 235                 240
Glu Gly Glu Asp Gly Asn Cys Phe His Leu Val Asp Ser Asp Pro Tyr
                245                 250                 255
Lys Val Gly Glu Ile Leu Asn Ile Phe Cys Glu Ala Gly His Ala Pro
            260                 265                 270
Arg Met Gly Met Arg Ile Asp Ser Arg Met Phe Gly Phe Ile Pro Pro
            275                 280                 285
Phe Ile Arg Gln Ser Ile Lys Asn Leu Pro Pro Val Lys Arg Ile Thr
    290                 295                 300
Gly Ala Leu Leu Asp Asp Met Gly Ile Pro Pro Ser Val Met Ser Phe
305                 310                 315                 320
Ile Asn Tyr Pro Thr Arg Phe Asp Thr Arg Glu Leu Glu Arg Val Leu
                325                 330                 335
Lys Gly Thr Asp Ile Glu Val Pro Arg Leu Pro Ser Tyr Ala Pro Val
            340                 345                 350
Ile Trp Asp Tyr Trp Glu Arg Asn Leu Asp Pro Asp Leu Phe Lys Asp
    355                 360                 365
Arg Thr Leu Lys Gly Thr Val Glu Gly Lys Val Cys Val Val Thr Gly
370                 375                 380
Ala Thr Ser Gly Ile Gly Leu Ala Thr Ala Glu Lys Leu Ala Glu Ala
385                 390                 395                 400
Gly Ala Ile Leu Val Ile Gly Ala Arg Thr Lys Glu Thr Leu Asp Glu
            405                 410                 415
Val Ala Ala Ser Leu Glu Ala Lys Gly Gly Asn Val His Ala Tyr Gln
            420                 425                 430
Cys Asp Phe Ser Asp Met Asp Asp Cys Asp Arg Phe Val Lys Thr Val
            435                 440                 445
Leu Asp Asn His Gly His Val Asp Val Leu Val Asn Asn Ala Gly Arg
    450                 455                 460
Ser Ile Arg Arg Ser Leu Ala Leu Ser Phe Asp Arg Phe His Asp Phe
465                 470                 475                 480
Glu Arg Thr Met Gln Leu Asn Tyr Phe Gly Ser Val Arg Leu Ile Met
                485                 490                 495
Gly Phe Ala Pro Ala Met Leu Glu Arg Arg Gly His Val Val Asn
            500                 505                 510
Ile Ser Ser Ile Gly Val Leu Thr Asn Ala Pro Arg Phe Ser Ala Tyr
            515                 520                 525
Val Ser Ser Lys Ser Ala Leu Asp Ala Phe Ser Arg Cys Ala Ala Ala
    530                 535                 540
Glu Trp Ser Asp Arg Asn Val Thr Phe Thr Thr Ile Asn Met Pro Leu
545                 550                 555                 560
Val Lys Thr Pro Met Ile Ala Pro Thr Lys Ile Tyr Asp Ser Val Pro
                565                 570                 575
Thr Leu Thr Pro Asp Glu Ala Ala Gln Met Val Ala Asp Ala Ile Val

-continued

```
                580                 585                 590
Tyr Arg Pro Lys Arg Ile Ala Thr Arg Leu Gly Val Phe Ala Gln Val
            595                 600                 605
Leu His Ala Leu Ala Pro Lys Met Gly Glu Ile Ile Met Asn Thr Gly
            610                 615                 620
Tyr Arg Met Phe Pro Asp Ser Pro Ala Ala Gly Ser Lys Ser Gly
625                 630                 635                 640
Glu Lys Pro Lys Val Ser Thr Glu Gln Val Ala Phe Ala Ala Ile Met
            645                 650                 655
Arg Gly Ile Tyr Trp
            660

<210> SEQ ID NO 2
<211> LENGTH: 661
<212> TYPE: PRT
<213> ORGANISM: Marinobacter manganoxydans
<220> FEATURE:
<223> OTHER INFORMATION: strain MnI7-9

<400> SEQUENCE: 2

Met Asn Tyr Phe Leu Thr Gly Gly Thr Gly Phe Ile Gly Arg Phe Leu
1               5                   10                  15
Val Glu Lys Leu Leu Ala Arg Gly Gly Thr Val His Val Leu Val Arg
            20                  25                  30
Glu Gln Ser Gln Asp Lys Leu Asp Lys Leu Arg Glu Arg Trp Gly Ala
        35                  40                  45
Asp Glu Thr Gln Val Lys Ala Val Ile Gly Asp Leu Thr Ser Lys Asn
    50                  55                  60
Leu Gly Ile Asp Ala Lys Thr Met Lys Ala Leu Lys Gly Lys Ile Asp
65                  70                  75                  80
His Phe Phe His Leu Ala Ala Val Tyr Asp Met Gly Ala Asp Glu Glu
                85                  90                  95
Ala Gln Gln Ala Thr Asn Ile Glu Gly Thr Arg Ala Ala Val Asn Ala
            100                 105                 110
Ala Glu Ala Met Gly Ala Lys His Phe His His Val Ser Ser Ile Ala
        115                 120                 125
Ala Ala Gly Leu Phe Lys Gly Ile Phe Arg Glu Asp Met Phe Glu Glu
    130                 135                 140
Ala Glu Lys Leu Asp His Pro Tyr Leu Arg Thr Lys His Glu Ser Glu
145                 150                 155                 160
Lys Val Val Arg Glu Glu Cys Lys Val Pro Phe Arg Ile Tyr Arg Pro
                165                 170                 175
Gly Met Val Ile Gly His Thr Ala Thr Gly Glu Met Asp Lys Val Asp
            180                 185                 190
Gly Pro Tyr Tyr Phe Phe Lys Met Ile Gln Lys Ile Arg His Ala Leu
        195                 200                 205
Pro Gln Trp Val Pro Thr Ile Gly Val Glu Gly Arg Leu Asn Ile
    210                 215                 220
Val Pro Val Asp Phe Val Val Asn Ala Met Asp His Ile Ala His Leu
225                 230                 235                 240
Glu Gly Glu Asp Gly Lys Cys Phe His Leu Val Asp Thr Asp Pro Tyr
                245                 250                 255
Lys Val Gly Glu Ile Leu Asn Ile Phe Ser Glu Ala Gly His Ala Pro
            260                 265                 270
Arg Met Gly Met Arg Ile Asp Ser Arg Met Phe Gly Phe Ile Pro Pro
```

```
            275                 280                 285
Phe Ile Arg Gln Ser Leu Lys Asn Leu Pro Val Lys Arg Leu Thr
290                 295                 300

Ser Ala Ile Leu Asp Asp Met Gly Ile Pro Ser Val Met Ser Phe
305                 310                 315                 320

Ile Asn Tyr Pro Thr Arg Phe Asp Ala Arg Glu Thr Glu Arg Val Leu
                325                 330                 335

Lys Gly Thr Gly Ile Glu Val Pro Arg Leu Pro Asp Tyr Ala Pro Val
                340                 345                 350

Ile Trp Asp Tyr Trp Glu Arg Asn Leu Asp Pro Asp Leu Phe Lys Asp
                355                 360                 365

Arg Thr Leu Lys Gly Thr Val Glu Gly Arg Val Cys Val Thr Gly
370                 375                 380

Ala Thr Ser Gly Ile Gly Leu Ala Thr Ala Gln Lys Leu Ala Asp Ala
385                 390                 395                 400

Gly Ala Ile Leu Val Ile Gly Ala Arg Lys Leu Glu Arg Leu Lys Glu
                405                 410                 415

Val Ala Ala Glu Leu Glu Ser Arg Gly Ala Ser Val His Ala Tyr Pro
                420                 425                 430

Cys Asp Phe Ser Asp Met Asp Ala Cys Asp Glu Phe Val Lys Thr Val
                435                 440                 445

Leu Asp Asn His Gly Gln Val Asp Val Leu Val Asn Asn Ala Gly Arg
450                 455                 460

Ser Ile Arg Arg Ser Leu Asp Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Lys Met Leu Glu Asn Arg Arg Gly His Val Val Asn
                500                 505                 510

Ile Ser Ser Ile Gly Val Leu Thr Asn Ala Pro Arg Phe Ser Ala Tyr
                515                 520                 525

Val Ala Ser Lys Ser Ala Leu Asp Ala Phe Ser Arg Cys Ala Ala Ser
                530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Thr Met Val Ala Asp Ala Ile Val
                580                 585                 590

Tyr Arg Pro Lys Arg Ile Ala Thr Arg Leu Gly Ile Phe Ala Gln Val
                595                 600                 605

Leu His Ala Leu Ala Pro Lys Met Ala Glu Ile Val Met Asn Thr Gly
                610                 615                 620

Tyr Arg Met Phe Pro Asp Ser Pro Ala Ala Gly Ser Arg Ser Gly
625                 630                 635                 640

Glu Lys Pro Lys Val Ser Ser Glu Gln Val Ala Phe Ala Ala Ile Met
                645                 650                 655

Arg Gly Ile Tyr Trp
                660
```

<210> SEQ ID NO 3
<211> LENGTH: 661
<212> TYPE: PRT
<213> ORGANISM: Marinobacter sp. ELB17

<400> SEQUENCE: 3

```
Met Asn Tyr Phe Val Thr Gly Gly Thr Gly Phe Ile Gly Arg Phe Leu
1               5                   10                  15

Ile Ala Arg Leu Leu Ala Arg Gly Ala Ile Val His Val Leu Val Arg
            20                  25                  30

Glu Gln Ser Val Gln Lys Leu Ala Asp Leu Arg Glu Lys Leu Gly Ala
        35                  40                  45

Asp Glu Lys Gln Ile Lys Ala Val Val Gly Asp Leu Thr Ala Pro Gly
    50                  55                  60

Leu Gly Leu Asp Lys Lys Thr Leu Lys Gln Leu Ser Gly Lys Ile Asp
65                  70                  75                  80

His Phe Phe His Leu Ala Ala Ile Tyr Asp Met Ser Ala Ser Glu Glu
                85                  90                  95

Ser Gln Gln Ala Ala Asn Ile Asp Gly Thr Arg Ala Ala Val Ala Ala
            100                 105                 110

Ala Glu Ala Leu Gly Ala Gly Ile Phe His His Val Ser Ser Ile Ala
        115                 120                 125

Val Ala Gly Leu Phe Lys Gly Thr Phe Arg Glu Asp Met Phe Ala Glu
    130                 135                 140

Ala Gly Lys Leu Asp His Pro Tyr Phe Ser Thr Lys His Glu Ser Glu
145                 150                 155                 160

Arg Val Val Arg Asp Glu Cys Lys Leu Pro Phe Arg Ile Tyr Arg Pro
                165                 170                 175

Gly Met Val Ile Gly Asp Ser Ala Thr Gly Glu Met Asp Lys Val Asp
            180                 185                 190

Gly Pro Tyr Tyr Phe Phe Lys Met Ile Gln Lys Ile Arg Gly Ala Leu
        195                 200                 205

Pro Gln Trp Val Pro Thr Ile Gly Leu Glu Gly Gly Arg Leu Asn Ile
    210                 215                 220

Val Pro Val Asn Phe Val Ala Asp Ala Leu Asp His Ile Ala His Leu
225                 230                 235                 240

Pro Asp Glu Asp Gly Lys Cys Phe His Leu Val Asp Ser Asp Pro Tyr
                245                 250                 255

Lys Val Gly Glu Ile Leu Asn Ile Phe Cys Glu Ala Gly His Ala Pro
            260                 265                 270

Lys Met Gly Met Arg Ile Asp Ser Arg Met Phe Gly Phe Val Pro Pro
        275                 280                 285

Phe Ile Arg Gln Ser Leu Lys Asn Leu Pro Pro Val Lys Arg Met Gly
    290                 295                 300

Arg Ala Leu Leu Asp Asp Leu Gly Ile Pro Ala Ser Val Leu Ser Phe
305                 310                 315                 320

Ile Asn Tyr Pro Thr Arg Phe Asp Ala Arg Glu Thr Glu Arg Val Leu
                325                 330                 335

Gln Gly Thr Gly Ile Glu Val Pro Arg Leu Pro Asp Tyr Ala Pro Val
            340                 345                 350

Ile Trp Asp Tyr Trp Glu Arg Asn Leu Asp Pro Asp Leu Phe Thr Asp
        355                 360                 365

Arg Thr Leu Arg Gly Thr Val Glu Gly Lys Val Cys Val Val Thr Gly
    370                 375                 380

Ala Thr Ser Gly Ile Gly Leu Ala Thr Ala Glu Lys Leu Ala Asp Ala
385                 390                 395                 400

Gly Ala Ile Leu Val Ile Gly Ala Arg Thr Gln Glu Thr Leu Asp Gln
```

405                 410                 415
Val Ser Ala Gln Leu Asn Ala Arg Gly Ala Asp Val His Ala Tyr Gln
                420                 425                 430

Cys Asp Phe Ala Asp Met Asp Ala Cys Asp Arg Phe Ile Gln Thr Val
            435                 440                 445

Ser Glu Asn His Gly Ala Val Asp Val Leu Ile Asn Asn Ala Gly Arg
    450                 455                 460

Ser Ile Arg Arg Ser Leu Asp Lys Ser Phe Asp Arg Phe His Asp Phe
465                 470                 475                 480

Glu Arg Thr Met Gln Leu Asn Tyr Phe Gly Ser Leu Arg Leu Ile Met
                485                 490                 495

Gly Phe Ala Pro Ala Met Leu Glu Arg Arg Gly His Ile Ile Asn
                500                 505                 510

Ile Ser Ser Ile Gly Val Leu Thr Asn Ala Pro Arg Phe Ser Ala Tyr
                515                 520                 525

Val Ala Ser Lys Ala Ala Leu Asp Ser Phe Ser Arg Cys Ala Ala Ala
    530                 535                 540

Glu Trp Ser Asp Arg His Val Cys Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Ser Pro Glu Glu Ala Ala Asp Met Val Val Asn Ala Ile Val
                580                 585                 590

Tyr Arg Pro Lys Arg Ile Ala Thr Arg Met Gly Val Phe Ala Gln Val
                595                 600                 605

Leu Asn Ala Val Ala Pro Lys Ala Ser Glu Ile Leu Met Asn Thr Gly
    610                 615                 620

Tyr Lys Met Phe Pro Asp Ser Met Pro Lys Lys Gly Lys Glu Val Ser
625                 630                 635                 640

Ala Glu Lys Gly Ala Ser Thr Asp Gln Val Ala Phe Ala Ala Ile Met
                645                 650                 655

Arg Gly Ile His Trp
            660

<210> SEQ ID NO 4
<211> LENGTH: 661
<212> TYPE: PRT
<213> ORGANISM: Marinobacter algicola
<220> FEATURE:
<223> OTHER INFORMATION: strain DG893

<400> SEQUENCE: 4

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val His Val Leu Val Arg
                20                  25                  30

Glu Gln Ser Gln Glu Lys Leu Asp Lys Leu Arg Glu Arg Trp Gly Ala
            35                  40                  45

Asp Glu Ser Arg Val Lys Ala Val Ile Gly Asp Leu Thr Ser Pro Asn
    50                  55                  60

Leu Gly Ile Asp Ala Lys Thr Met Lys Ser Leu Lys Gly Asn Ile Asp
65                  70                  75                  80

His Phe Phe His Leu Ala Ala Val Tyr Asp Met Gly Ala Asp Glu Lys
                85                  90                  95

Ser Gln Gln Ala Thr Asn Ile Glu Gly Thr His Ser Ala Val Asn Ala

```
            100                 105                 110
Ala Ala Ala Met Glu Ala Gly Cys Phe His His Val Ser Ser Ile Ala
        115                 120                 125
Ala Ala Gly Leu Phe Lys Gly Thr Phe Arg Glu Asp Met Phe Glu Glu
        130                 135                 140
Ala Glu Lys Leu Asp His Pro Tyr Leu Leu Thr Lys His Glu Ser Glu
145                 150                 155                 160
Lys Val Val Arg Glu Ser Cys Lys Val Pro Phe Arg Ile Tyr Arg Pro
                165                 170                 175
Gly Met Val Val Gly His Ser Lys Thr Gly Glu Met Asp Lys Val Asp
                180                 185                 190
Gly Pro Tyr Tyr Phe Phe Lys Met Ile Gln Lys Ile Arg His Ala Leu
                195                 200                 205
Pro Gln Trp Val Pro Thr Ile Gly Ile Glu Gly Gly Arg Leu Asn Ile
        210                 215                 220
Val Pro Val Asp Phe Val Val Asn Ala Met Asp His Ile Ala His Leu
225                 230                 235                 240
Lys Gly Glu Asp Gly Asn Cys Phe His Leu Val Asp Ser Asp Pro Tyr
                245                 250                 255
Lys Val Gly Glu Ile Leu Asn Ile Phe Ser Glu Ala Gly His Ala Pro
                260                 265                 270
Arg Met Ala Met Arg Ile Asp Ser Arg Met Phe Gly Phe Val Pro Pro
                275                 280                 285
Phe Ile Arg Gln Ser Leu Lys Asn Leu Pro Pro Val Lys Arg Leu Thr
        290                 295                 300
Thr Ala Leu Leu Asp Asp Met Gly Ile Pro Pro Ser Val Leu Ser Phe
305                 310                 315                 320
Ile Asn Tyr Pro Thr Arg Phe Asp Ala Arg Glu Thr Glu Arg Val Leu
                325                 330                 335
Lys Asp Thr Gly Ile Val Val Pro Arg Leu Glu Ser Tyr Ala Ala Val
                340                 345                 350
Leu Trp Asp Phe Trp Glu Arg Asn Leu Asp Pro Asp Leu Phe Lys Asp
                355                 360                 365
Arg Thr Leu Arg Gly Thr Val Glu Gly Lys Val Cys Val Ile Thr Gly
        370                 375                 380
Gly Thr Ser Gly Ile Gly Leu Ala Thr Ala Gln Lys Leu Ala Asp Ala
385                 390                 395                 400
Gly Ala Ile Leu Val Ile Gly Ala Arg Lys Lys Glu Arg Leu Met Glu
                405                 410                 415
Val Ala Ala Glu Leu Glu Ala Arg Gly Gly Asn Val His Ala Tyr Gln
                420                 425                 430
Cys Asp Phe Ala Asp Met Asp Asp Cys Asp Arg Phe Val Lys Thr Val
                435                 440                 445
Leu Asp Asn His Gly His Val Asp Val Leu Val Asn Asn Ala Gly Arg
        450                 455                 460
Ser Ile Arg Arg Ser Leu Ala Leu Ser Phe Asp Arg Phe His Asp Phe
465                 470                 475                 480
Glu Arg Thr Met Gln Leu Asn Tyr Phe Gly Ser Val Arg Leu Ile Met
                485                 490                 495
Gly Phe Ala Pro Ala Met Leu Glu Arg Arg Gly His Val Val Asn
                500                 505                 510
Ile Ser Ser Ile Gly Val Leu Thr Asn Ala Pro Arg Phe Ser Ala Tyr
        515                 520                 525
```

```
Val Ala Ser Lys Ser Ala Leu Asp Thr Phe Ser Arg Cys Ala Ala Ala
        530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Glu Met Val Ala Asp Ala Ile Val
            580                 585                 590

Tyr Arg Pro Lys Arg Ile Ala Thr Arg Leu Gly Ile Phe Ala Gln Val
        595                 600                 605

Met Gln Ala Leu Ala Pro Lys Met Gly Glu Ile Val Met Asn Thr Gly
610                 615                 620

Tyr Arg Met Phe Pro Asp Ser Pro Ala Ala Gly Ser Arg Ser Gly
625                 630                 635                 640

Ala Lys Pro Lys Val Ser Ser Glu Gln Val Ala Phe Ala Ala Ile Met
                645                 650                 655

Arg Gly Ile Tyr Trp
            660

<210> SEQ ID NO 5
<211> LENGTH: 345
<212> TYPE: PRT
<213> ORGANISM: Myxococcus xanthus
<220> FEATURE:
<223> OTHER INFORMATION: strain DK 1622

<400> SEQUENCE: 5

Met Lys Ala Val Val Leu Arg Ser Phe Gly Glu Ala Gly Asn Leu Lys
1               5                   10                  15

Met Glu Thr Met Pro Met Pro Arg Pro Gly Arg Gly Glu Val Leu Leu
            20                  25                  30

Arg Val His Ala Cys Gly Val Cys Tyr His Asp Val Ile Asn Arg Arg
        35                  40                  45

Gly Asn Leu Pro Arg Thr Ser Val Pro Ala Ile Leu Gly His Glu Ala
    50                  55                  60

Ala Gly Glu Val Ile Glu Val Gly Pro Asp Thr Pro Gly Trp Lys Thr
65                  70                  75                  80

Gly Asp Arg Ala Ala Thr Leu Gln Arg Met Ser Cys Gly Asp Cys Ala
                85                  90                  95

Leu Cys Arg Ser Gly Arg Asn Ser Leu Cys Lys Thr Asp Asn Arg Phe
            100                 105                 110

Phe Gly Glu Glu Leu Pro Gly Gly Tyr Ala Gln Phe Met Val Ala Pro
        115                 120                 125

Val Gly Gly Leu Gly Arg Val Pro Ala Ser Leu Pro Trp Asn Glu Ala
    130                 135                 140

Ala Thr Val Cys Cys Thr Thr Gly Thr Ala Val His Thr Val Arg Thr
145                 150                 155                 160

Arg Gly Lys Val Arg Ala Gly Glu Thr Val Leu Ile Thr Gly Ala Ser
                165                 170                 175

Gly Gly Val Gly Leu Ser Ser Val Gln Leu Ala Arg Leu Asp Gly Ala
            180                 185                 190

Arg Val Ile Ala Val Thr Ser Ser Glu Ala Lys Val Gln Ala Leu Lys
        195                 200                 205

Glu Ala Gly Ala Asp Glu Val Ile Val Ser Arg Gly Leu Asp Phe Ala
    210                 215                 220
```

```
Ser Asp Val Arg Lys Arg Thr Gln Gly Ala Gly Val Asp Val Ala Val
225                 230                 235                 240

Glu Ile Val Gly Ser Ala Thr Phe Asp Gln Thr Leu Lys Ser Met Ala
            245                 250                 255

Pro Gly Gly Arg Val Val Val Gly Asn Leu Glu Ser Gly Met Val
        260                 265                 270

Gln Leu Asn Pro Gly Leu Val Ile Val Lys Glu Leu Glu Ile Leu Gly
        275                 280                 285

Ala Tyr Ala Thr Thr Gln Ala Glu Leu Asp Glu Ala Leu Arg Leu Thr
        290                 295                 300

Ala Thr Gly Gly Val Arg Gln Phe Val Thr Asp Ala Val Pro Leu Ala
305                 310                 315                 320

Glu Ala Ala Lys Ala His Phe Arg Leu Glu Asn Arg Glu Val Ala Gly
                325                 330                 335

Arg Leu Val Leu Val Pro Pro Glu Ala
            340                 345

<210> SEQ ID NO 6
<211> LENGTH: 258
<212> TYPE: PRT
<213> ORGANISM: Myxococcus sp.

<400> SEQUENCE: 6

Met Pro Glu Phe Lys Val Asp Ala Arg Gly Pro Ile Glu Ile Trp Thr
1               5                   10                  15

Ile Asp Gly Glu Ser Arg Arg Asn Ala Ile Ser Arg Ala Met Leu Gln
            20                  25                  30

Glu Leu Gly Glu Met Val Thr Arg Val Ser Ser Ser Arg Glu Val Arg
        35                  40                  45

Ala Val Val Ile Thr Gly Ala Gly Asp Lys Ala Phe Cys Ala Gly Ala
    50                  55                  60

Asp Leu Lys Glu Arg Ala Thr Met Ala Glu Asp Glu Val Arg Ala Phe
65                  70                  75                  80

Leu Asp Gly Leu Arg Arg Thr Phe Arg Ala Leu Glu Lys Ser Asp Cys
                85                  90                  95

Val Phe Ile Ala Ala Ile Asn Gly Ala Ala Phe Gly Gly Gly Thr Glu
            100                 105                 110

Leu Ala Leu Ala Cys Asp Leu Arg Val Ala Ala Pro Ala Ala Glu Leu
        115                 120                 125

Gly Leu Thr Glu Val Lys Leu Gly Ile Ile Pro Gly Gly Gly Thr
    130                 135                 140

Gln Arg Leu Thr Arg Leu Val Gly Pro Gly Arg Ala Lys Asp Leu Ile
145                 150                 155                 160

Leu Thr Ala Arg Arg Ile Asn Ala Ala Glu Ala Phe Ser Val Gly Leu
                165                 170                 175

Val Asn Arg Leu Ala Pro Glu Gly His Leu Leu Ala Val Ala Tyr Gly
            180                 185                 190

Leu Ala Glu Ser Val Val Glu Asn Ala Pro Ile Ala Val Ala Thr Ala
        195                 200                 205

Lys His Ala Ile Asp Glu Gly Thr Gly Leu Glu Leu Asp Asp Ala Leu
    210                 215                 220

Ala Leu Glu Leu Arg Lys Tyr Glu Glu Ile Leu Lys Thr Glu Asp Arg
225                 230                 235                 240

Leu Glu Gly Leu Arg Ala Phe Ala Glu Lys Arg Ala Pro Val Tyr Lys
```

Gly Arg

<210> SEQ ID NO 7
<211> LENGTH: 447
<212> TYPE: PRT
<213> ORGANISM: Schizosaccharomyces pombe
<220> FEATURE:
<223> OTHER INFORMATION: strain 972 / ATCC 24843

<400> SEQUENCE: 7

Met Ser Phe Asp Arg Lys Asp Ile Gly Ile Lys Gly Leu Val Leu Tyr
1               5                   10                  15

Thr Pro Asn Gln Tyr Val Glu Gln Ala Ala Leu Glu Ala His Asp Gly
            20                  25                  30

Val Ser Thr Gly Lys Tyr Thr Ile Gly Leu Gly Leu Thr Lys Met Ala
        35                  40                  45

Phe Val Asp Asp Arg Glu Asp Ile Tyr Ser Phe Gly Leu Thr Ala Leu
    50                  55                  60

Ser Gln Leu Ile Lys Arg Tyr Gln Ile Asp Ile Ser Lys Ile Gly Arg
65                  70                  75                  80

Leu Glu Val Gly Thr Glu Thr Ile Ile Asp Lys Ser Lys Ser Val Lys
                85                  90                  95

Ser Val Leu Met Gln Leu Phe Gly Asp Asn His Asn Val Glu Gly Ile
            100                 105                 110

Asp Cys Val Asn Ala Cys Tyr Gly Gly Val Asn Ala Leu Phe Asn Thr
        115                 120                 125

Ile Asp Trp Ile Glu Ser Ser Ala Trp Asp Gly Arg Asp Gly Ile Val
    130                 135                 140

Val Ala Gly Asp Ile Ala Leu Tyr Ala Lys Gly Asn Ala Arg Pro Thr
145                 150                 155                 160

Gly Gly Ala Gly Cys Val Ala Leu Leu Val Gly Pro Asn Ala Pro Ile
                165                 170                 175

Val Phe Glu Pro Gly Leu Arg Gly Thr Tyr Met Gln His Ala Tyr Asp
            180                 185                 190

Phe Tyr Lys Pro Asp Leu Thr Ser Glu Tyr Pro Tyr Val Asp Gly His
        195                 200                 205

Phe Ser Leu Glu Cys Tyr Val Lys Ala Leu Asp Gly Ala Tyr Ala Asn
    210                 215                 220

Tyr Asn Val Arg Asp Val Ala Lys Asn Gly Lys Ser Gln Gly Leu Gly
225                 230                 235                 240

Leu Asp Arg Phe Asp Tyr Cys Ile Phe His Ala Pro Thr Cys Lys Gln
                245                 250                 255

Val Gln Lys Ala Tyr Ala Arg Leu Leu Tyr Thr Asp Ser Ala Ala Glu
            260                 265                 270

Pro Ser Asn Pro Glu Leu Glu Gly Val Arg Glu Leu Leu Ser Thr Leu
        275                 280                 285

Asp Ala Lys Lys Ser Leu Thr Asp Lys Ala Leu Glu Lys Gly Leu Met
    290                 295                 300

Ala Ile Thr Lys Glu Arg Phe Asn Lys Arg Val Ser Pro Ser Val Tyr
305                 310                 315                 320

Ala Pro Thr Asn Cys Gly Asn Met Tyr Thr Ala Ser Ile Phe Ser Cys
                325                 330                 335

Leu Thr Ala Leu Leu Ser Arg Val Pro Ala Asp Glu Leu Lys Gly Lys
            340                 345                 350

-continued

Arg Val Gly Ala Tyr Ser Tyr Gly Ser Gly Leu Ala Ala Ser Phe Phe
          355                 360                 365

Ser Phe Val Val Lys Gly Asp Val Ser Glu Ile Ala Lys Lys Thr Asn
370                 375                 380

Leu Val Asn Asp Leu Asp Asn Arg His Cys Leu Thr Pro Thr Gln Tyr
385                 390                 395                 400

Glu Glu Ala Ile Glu Leu Arg His Gln Ala His Leu Lys Lys Asn Phe
                405                 410                 415

Thr Pro Lys Gly Ser Ile Glu Arg Leu Arg Ser Gly Thr Tyr Tyr Leu
                420                 425                 430

Thr Gly Ile Asp Asp Met Phe Arg Arg Ser Tyr Ser Val Lys Pro
          435                 440                 445

<210> SEQ ID NO 8
<211> LENGTH: 392
<212> TYPE: PRT
<213> ORGANISM: Clostridium acetobutylicum
<220> FEATURE:
<223> OTHER INFORMATION: strain ATCC 824 / DSM 792 / JCM 1419 / LMG
      5710 / VKM B-1787

<400> SEQUENCE: 8

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu

```
                    260                 265                 270
Ala Lys Ile Val Ser Tyr Gly Ser Ala Gly Val Asp Pro Ala Ile Met
            275                 280                 285

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
            370                 375                 380

Thr Ala Ile Leu Leu Glu Lys Cys
385                 390

<210> SEQ ID NO 9
<211> LENGTH: 462
<212> TYPE: PRT
<213> ORGANISM: Klebsiella pneumoniae
<220> FEATURE:
<223> OTHER INFORMATION: Subspecies pneumoniae

<400> SEQUENCE: 9

Met Asn Thr Ala Glu Leu Glu Thr Leu Ile Arg Thr Ile Leu Ser Glu
1               5                   10                  15

Lys Leu Ala Pro Thr Pro Pro Ala Pro Gln Gln Glu Gln Gly Ile Phe
            20                  25                  30

Cys Asp Val Gly Ser Ala Ile Asp Ala Ala His Gln Ala Phe Leu Arg
        35                  40                  45

Tyr Gln Gln Cys Pro Leu Lys Thr Arg Ser Ala Ile Ile Ser Ala Leu
    50                  55                  60

Arg Glu Thr Leu Ala Pro Glu Leu Ala Thr Leu Ala Glu Glu Ser Ala
65                  70                  75                  80

Thr Glu Thr Gly Met Gly Asn Lys Glu Asp Lys Tyr Leu Lys Asn Lys
                85                  90                  95

Ala Ala Leu Glu Asn Thr Pro Gly Ile Glu Asp Leu Thr Thr Ser Ala
            100                 105                 110

Leu Thr Gly Asp Gly Gly Met Val Leu Phe Glu Tyr Ser Pro Phe Gly
        115                 120                 125

Val Ile Gly Ala Val Ala Pro Ser Thr Asn Pro Thr Glu Thr Ile Ile
    130                 135                 140

Asn Asn Ser Ile Ser Met Leu Ala Ala Gly Asn Ser Val Tyr Phe Ser
145                 150                 155                 160

Pro His Pro Gly Ala Lys Lys Val Ser Leu Lys Leu Ile Ala Arg Ile
                165                 170                 175

Glu Glu Ile Ala Tyr Arg Cys Ser Gly Ile Arg Asn Leu Val Val Thr
            180                 185                 190

Val Ala Glu Pro Thr Phe Glu Ala Thr Gln Gln Met Met Ser His Pro
        195                 200                 205

Leu Ile Ala Val Leu Ala Ile Thr Gly Gly Pro Gly Ile Val Ala Met
    210                 215                 220

Gly Met Lys Ser Gly Lys Lys Val Ile Gly Ala Gly Ala Gly Asn Pro
```

```
                225                 230                 235                 240
        Pro Cys Ile Val Asp Glu Thr Ala Asp Leu Val Lys Ala Ala Glu Asp
                        245                 250                 255
        Ile Ile Ser Gly Ala Ala Phe Asp Tyr Asn Leu Pro Cys Ile Ala Glu
                        260                 265                 270
        Lys Ser Leu Ile Val Val Ala Ser Val Ala Asp Arg Leu Ile Gln Gln
                        275                 280                 285
        Met Gln Asp Phe Asp Ala Leu Leu Leu Ser Arg Gln Glu Ala Asp Thr
                290                 295                 300
        Leu Arg Ala Val Cys Leu Pro Asp Gly Ala Ala Asn Lys Lys Leu Val
        305                 310                 315                 320
        Gly Lys Ser Pro Ala Ala Leu Ala Ala Ala Gly Leu Ala Val Pro
                        325                 330                 335
        Pro Arg Pro Arg Leu Leu Ile Ala Glu Val Glu Ala Asn Asp Pro
                        340                 345                 350
        Trp Val Thr Cys Glu Gln Leu Met Pro Val Leu Pro Ile Val Arg Val
                        355                 360                 365
        Ala Asp Phe Asp Ser Ala Leu Ala Leu Ala Leu Arg Val Glu Glu Gly
                370                 375                 380
        Leu His His Thr Ala Ile Met His Ser Gln Asn Val Ser Arg Leu Asn
        385                 390                 395                 400
        Leu Ala Ala Arg Thr Leu Gln Thr Ser Ile Phe Val Lys Asn Gly Pro
                        405                 410                 415
        Ser Tyr Ala Gly Ile Gly Val Gly Glu Gly Phe Thr Thr Phe Thr
                        420                 425                 430
        Ile Ala Thr Pro Thr Gly Glu Gly Thr Thr Ser Ala Arg Thr Phe Ala
                        435                 440                 445
        Arg Leu Arg Arg Cys Val Leu Thr Asn Gly Phe Ser Ile Arg
                450                 455                 460

<210> SEQ ID NO 10
<211> LENGTH: 464
<212> TYPE: PRT
<213> ORGANISM: Salmonella enterica
<220> FEATURE:
<223> OTHER INFORMATION: Subspecies enterica serovar Typhimurium

<400> SEQUENCE: 10

Met Asn Thr Ser Glu Leu Glu Thr Leu Ile Arg Thr Ile Leu Ser Glu
1               5                   10                  15
Gln Leu Thr Thr Pro Ala Gln Thr Pro Val Gln Pro Gln Gly Lys Gly
                20                  25                  30
Ile Phe Gln Ser Val Ser Glu Ala Ile Asp Ala Ala His Gln Ala Phe
            35                  40                  45
Leu Arg Tyr Gln Gln Cys Pro Leu Lys Thr Arg Ser Ala Ile Ile Ser
        50                  55                  60
Ala Met Arg Gln Glu Leu Thr Pro Leu Leu Ala Pro Leu Ala Glu Glu
65                  70                  75                  80
Ser Ala Asn Glu Thr Gly Met Gly Asn Lys Glu Asp Lys Phe Leu Lys
                85                  90                  95
Asn Lys Ala Ala Leu Asp Asn Thr Pro Gly Val Glu Asp Leu Thr Thr
            100                 105                 110
Thr Ala Leu Thr Gly Asp Gly Gly Met Val Leu Phe Glu Tyr Ser Pro
        115                 120                 125
Phe Gly Val Ile Gly Ser Val Ala Pro Ser Thr Asn Pro Thr Glu Thr
```

```
                130                 135                 140
Ile Ile Asn Asn Ser Ile Ser Met Leu Ala Ala Gly Asn Ser Ile Tyr
145                 150                 155                 160

Phe Ser Pro His Pro Gly Ala Lys Lys Val Ser Leu Lys Leu Ile Ser
                165                 170                 175

Leu Ile Glu Glu Ile Ala Phe Arg Cys Cys Gly Ile Arg Asn Leu Val
            180                 185                 190

Val Thr Val Ala Glu Pro Thr Phe Glu Ala Thr Gln Gln Met Met Ala
        195                 200                 205

His Pro Arg Ile Ala Val Leu Ala Ile Thr Gly Gly Pro Gly Ile Val
    210                 215                 220

Ala Met Gly Met Lys Ser Gly Lys Lys Val Ile Gly Ala Gly Ala Gly
225                 230                 235                 240

Asn Pro Pro Cys Ile Val Asp Glu Thr Ala Asp Leu Val Lys Ala Ala
                245                 250                 255

Glu Asp Ile Ile Asn Gly Ala Ser Phe Asp Tyr Asn Leu Pro Cys Ile
            260                 265                 270

Ala Glu Lys Ser Leu Ile Val Val Glu Ser Val Ala Glu Arg Leu Val
        275                 280                 285

Gln Gln Met Gln Thr Phe Gly Ala Leu Leu Leu Ser Pro Ala Asp Thr
    290                 295                 300

Asp Lys Leu Arg Ala Val Cys Leu Pro Glu Gly Gln Ala Asn Lys Lys
305                 310                 315                 320

Leu Val Gly Lys Ser Pro Ser Ala Met Leu Glu Ala Ala Gly Ile Ala
                325                 330                 335

Val Pro Ala Lys Ala Pro Arg Leu Leu Ile Ala Leu Val Asn Ala Asp
            340                 345                 350

Asp Pro Trp Val Thr Ser Glu Gln Leu Met Pro Met Leu Pro Val Val
        355                 360                 365

Lys Val Ser Asp Phe Asp Ser Ala Leu Ala Leu Ala Leu Lys Val Glu
    370                 375                 380

Glu Gly Leu His His Thr Ala Ile Met His Ser Gln Asn Val Ser Arg
385                 390                 395                 400

Leu Asn Leu Ala Ala Arg Thr Leu Gln Thr Ser Ile Phe Val Lys Asn
                405                 410                 415

Gly Pro Ser Tyr Ala Gly Ile Gly Val Gly Gly Glu Gly Phe Thr Thr
            420                 425                 430

Phe Thr Ile Ala Thr Pro Thr Gly Glu Gly Thr Thr Ser Ala Arg Thr
        435                 440                 445

Phe Ala Arg Ser Arg Arg Cys Val Leu Thr Asn Gly Phe Ser Ile Arg
    450                 455                 460

<210> SEQ ID NO 11
<211> LENGTH: 661
<212> TYPE: PRT
<213> ORGANISM: Hallella chejuensis
<220> FEATURE:
<223> OTHER INFORMATION: strain KCTC 2396

<400> SEQUENCE: 11

Met Asn Tyr Phe Val Thr Gly Gly Thr Gly Phe Ile Gly Arg Phe Leu
1               5                   10                  15

Val Pro Lys Leu Leu Lys Arg Gly Gly Thr Val Tyr Leu Leu Val Arg
            20                  25                  30

Glu Ala Ser Leu Pro Lys Leu Asp Glu Leu Arg Glu Arg Trp Asn Ala
```

```
                    35                  40                  45
Ser Asp Glu Gln Val Val Gly Val Gly Asp Leu Ala Gln Pro Met
        50                  55                  60
Leu Gly Val Ser Glu Lys Asp Ala Ala Met Leu Arg Gly Lys Val Gly
65                  70                  75                  80
His Phe Phe His Leu Ala Ala Ile Tyr Asp Met Gln Ala Ser Ala Glu
                85                  90                  95
Ser Gln Glu Gln Ala Asn Ile Glu Gly Thr Arg Asn Ala Val Lys Leu
            100                 105                 110
Ala Asp Ser Leu Lys Ala Ala Cys Phe His His Val Ser Ser Ile Ala
            115                 120                 125
Ala Ala Gly Leu Tyr Arg Gly Ile Phe Arg Glu Asp Met Phe Glu Glu
            130                 135                 140
Ala Glu Lys Leu Asp Asn Pro Tyr Leu Arg Thr Lys His Glu Ser Glu
145                 150                 155                 160
Lys Val Val Arg Glu Glu Cys Gln Thr Pro Trp Arg Val Tyr Arg Pro
                165                 170                 175
Gly Met Val Val Gly His Ser Lys Thr Gly Glu Ile Asp Lys Ile Asp
                180                 185                 190
Gly Pro Tyr Tyr Phe Phe Lys Leu Ile Gln Lys Leu Arg Ser Ala Leu
            195                 200                 205
Pro Gln Trp Met Pro Thr Val Gly Leu Glu Gly Gly Arg Ile Asn Ile
            210                 215                 220
Val Pro Val Asp Phe Val Val Asp Ala Met Asp His Ile Ala His Ala
225                 230                 235                 240
Glu Gly Glu Asp Gly Lys Cys Phe His Leu Thr Asp Pro Asp Pro Tyr
                245                 250                 255
Lys Val Gly Glu Ile Leu Asn Ile Phe Ala Glu Ala Gly His Ala Pro
                260                 265                 270
Lys Met Ala Met Arg Ile Asp Ala Arg Met Phe Gly Phe Ile Pro Pro
            275                 280                 285
Met Ile Arg Gln Gly Ile Ala Arg Leu Pro Pro Val Gln Arg Met Lys
            290                 295                 300
Asn Ala Val Leu Asn Asp Leu Gly Ile Pro Asp Glu Val Met Ser Phe
305                 310                 315                 320
Ile Asn Tyr Pro Thr Arg Phe Asp Asn Arg Glu Thr Glu Arg Leu Leu
                325                 330                 335
Lys Gly Thr Ala Ile Ala Val Pro Arg Leu Gln Asp Tyr Ser Pro Ala
            340                 345                 350
Ile Trp Asp Tyr Trp Glu Arg His Leu Asp Pro Asp Leu His Lys Asp
            355                 360                 365
Arg Thr Leu Arg Gly Ala Val Glu Gly Arg Val Cys Val Ile Thr Gly
            370                 375                 380
Ala Thr Ser Gly Ile Gly Leu Ser Ala Ala Arg Lys Leu Ala Glu Ala
385                 390                 395                 400
Gly Ala Lys Val Val Ile Ala Ala Arg Thr Leu Glu Lys Leu Gln Glu
                405                 410                 415
Val Lys Lys Glu Leu Glu Glu Leu Gly Gly Glu Val Tyr Glu Tyr Ser
            420                 425                 430
Val Asp Leu Ser Asp Leu Glu Asp Cys Asp Arg Phe Val Ala Asn Val
            435                 440                 445
Leu Lys Asp Leu Gly His Val Asp Val Leu Val Asn Asn Ala Gly Arg
            450                 455                 460
```

-continued

```
Ser Ile Arg Arg Ser Ile Gln His Ala Phe Asp Arg Phe His Asp Phe
465                 470                 475                 480

Glu Arg Thr Met Gln Leu Asn Tyr Phe Gly Ser Leu Arg Leu Ile Met
            485                 490                 495

Gly Phe Ala Pro Ser Met Leu Glu Arg Arg Gly His Ile Val Asn
        500                 505                 510

Ile Ser Ser Ile Gly Val Leu Thr Asn Ala Pro Arg Phe Ser Ala Tyr
        515                 520                 525

Val Ala Ser Lys Ala Ala Leu Asp Ala Phe Ser Arg Cys Ala Ala Ala
530                 535                 540

Glu Phe Ser Asp Lys Asn Val Thr Phe Thr Ile Asn Met Pro Leu
545                 550                 555                 560

Val Arg Thr Pro Met Ile Ser Pro Thr Lys Ile Tyr Asp Ser Val Pro
                565                 570                 575

Thr Leu Thr Pro Glu Glu Ala Ala Asp Leu Val Ala Glu Ala Ile Ile
            580                 585                 590

His Arg Pro Lys Arg Ile Ala Thr Arg Leu Gly Val Phe Ala Gln Val
        595                 600                 605

Leu His Ser Met Ala Pro Lys Phe Ser Glu Ile Ile Met Asn Thr Gly
    610                 615                 620

Phe Lys Met Phe Pro Asp Ser Ser Ala Ala Thr Gly Gly Lys Asp Gly
625                 630                 635                 640

Glu Lys Pro Lys Val Ser Thr Glu Gln Val Ala Phe Ala Ala Ile Met
                645                 650                 655

Arg Gly Ile His Trp
            660

<210> SEQ ID NO 12
<211> LENGTH: 418
<212> TYPE: PRT
<213> ORGANISM: Myxococcus xanthus
<220> FEATURE:
<223> OTHER INFORMATION: strain DK 1622

<400> SEQUENCE: 12

Met Lys Lys Arg Val Gly Ile Glu Ala Leu Ala Val Ala Val Pro Ser
1               5                   10                  15

Arg Tyr Val Asp Ile Glu Asp Leu Ala Arg Ala Arg Gly Val Asp Pro
            20                  25                  30

Ala Lys Tyr Thr Ala Gly Leu Gly Ala Arg Glu Met Ala Val Thr Asp
        35                  40                  45

Pro Gly Glu Asp Thr Val Ala Leu Ala Ala Thr Ala Ala Ala Arg Leu
    50                  55                  60

Ile Arg Gln Gln Asp Val Asp Pro Ser Arg Ile Gly Met Leu Val Val
65                  70                  75                  80

Gly Thr Glu Thr Gly Ile Asp His Ser Lys Pro Val Ala Ser His Val
                85                  90                  95

Gln Gly Leu Leu Lys Leu Pro Arg Thr Met Arg Thr Tyr Asp Thr Gln
            100                 105                 110

His Ala Cys Tyr Gly Gly Thr Ala Gly Leu Met Ala Ala Val Glu Trp
        115                 120                 125

Ile Ala Ser Gly Ala Gly Ala Gly Lys Val Ala Val Val Cys Ser
    130                 135                 140

Asp Ile Ala Arg Tyr Gly Leu Asn Thr Ala Gly Glu Pro Thr Gln Gly
145                 150                 155                 160
```

Gly Gly Ala Val Ala Leu Leu Val Ser Glu Gln Pro Asp Leu Leu Ala
            165                 170                 175

Met Asp Val Gly Leu Asn Gly Val Cys Ser Met Asp Val Tyr Asp Phe
        180                 185                 190

Trp Arg Pro Val Gly Arg Arg Glu Ala Leu Val Asp Gly His Tyr Ser
        195                 200                 205

Ile Thr Cys Tyr Leu Glu Ala Leu Ser Gly Ala Tyr Arg Gly Trp Arg
        210                 215                 220

Glu Lys Ala Leu Ala Ala Gly Leu Val Arg Trp Ser Asp Ala Leu Pro
225                 230                 235                 240

Gly Glu Gln Leu Ala Arg Ile Ala Tyr His Val Pro Phe Cys Lys Met
            245                 250                 255

Ala Arg Lys Ala His Thr Gln Leu Arg Leu Cys Asp Leu Glu Asp Ala
            260                 265                 270

Ala Asp Ala Ala Ala Ser Thr Pro Glu Ser Arg Glu Ala Gln Ala Lys
            275                 280                 285

Ser Ala Ala Ser Tyr Asp Ala Gln Val Ala Thr Ser Leu Gly Leu Asn
        290                 295                 300

Ser Arg Ile Gly Asn Val Tyr Thr Ala Ser Leu Tyr Leu Ala Leu Ala
305                 310                 315                 320

Gly Leu Leu Gln His Glu Ala Gly Ala Leu Ala Gly Gln Arg Ile Gly
            325                 330                 335

Leu Leu Ser Tyr Gly Ser Gly Cys Ala Ala Glu Phe Tyr Ser Gly Thr
            340                 345                 350

Val Gly Glu Lys Ala Ala Glu Arg Met Ala Lys Ala Asp Leu Glu Ala
        355                 360                 365

Val Leu Ala Arg Arg Glu Arg Val Ser Ile Glu Glu Tyr Glu Arg Leu
    370                 375                 380

Met Lys Leu Pro Ala Asp Ala Pro Glu Ala Val Ala Pro Ser Pro Gly
385                 390                 395                 400

Ala Phe Arg Leu Thr Glu Ile Arg Asp His Arg Arg Gln Tyr Ala Glu
            405                 410                 415

Gly Asn

<210> SEQ ID NO 13
<211> LENGTH: 660
<212> TYPE: PRT
<213> ORGANISM: Marinobacter hydrocarbonoclasticus
<220> FEATURE:
<223> OTHER INFORMATION: strain ATCC 49840 (Uniprot H8W980)
<220> FEATURE:
<223> OTHER INFORMATION: short chain dehydrogenase/reductase

<400> SEQUENCE: 13

Met Asn Tyr Phe Leu Thr Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
        50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu

```
                    85                  90                  95
Ala Gln Ala Ala Thr Asn Ile Glu Gly Thr Arg Ala Ala Val Gln Ala
                100                 105                 110
Ala Glu Ala Met Gly Ala Lys His Phe His His Val Ser Ser Ile Ala
                115                 120                 125
Ala Ala Gly Leu Phe Lys Gly Ile Phe Arg Glu Asp Met Phe Glu Glu
                130                 135                 140
Ala Glu Lys Leu Asp His Pro Tyr Leu Arg Thr Lys His Glu Ser Glu
145                 150                 155                 160
Lys Val Val Arg Glu Glu Cys Lys Val Pro Phe Arg Ile Tyr Arg Pro
                165                 170                 175
Gly Met Val Ile Gly His Ser Glu Thr Gly Glu Met Asp Lys Val Asp
                180                 185                 190
Gly Pro Tyr Tyr Phe Phe Lys Met Ile Gln Lys Ile Arg His Ala Leu
                195                 200                 205
Pro Gln Trp Val Pro Thr Ile Gly Ile Glu Gly Gly Arg Leu Asn Ile
                210                 215                 220
Val Pro Val Asp Phe Val Val Asp Ala Leu Asp His Ile Ala His Leu
225                 230                 235                 240
Glu Gly Glu Asp Gly Asn Cys Phe His Leu Val Asp Ser Asp Pro Tyr
                245                 250                 255
Lys Val Gly Glu Ile Leu Asn Ile Phe Cys Glu Ala Gly His Ala Pro
                260                 265                 270
Arg Met Gly Met Arg Ile Asp Ser Arg Met Phe Gly Phe Ile Pro Pro
                275                 280                 285
Phe Ile Arg Gln Ser Ile Lys Asn Leu Pro Pro Val Lys Arg Ile Thr
                290                 295                 300
Gly Ala Leu Leu Asp Asp Met Gly Ile Pro Pro Ser Val Met Ser Phe
305                 310                 315                 320
Ile Asn Tyr Pro Thr Arg Phe Asp Thr Arg Glu Leu Glu Arg Val Leu
                325                 330                 335
Lys Gly Thr Asp Ile Glu Val Pro Arg Leu Pro Ser Tyr Ala Pro Val
                340                 345                 350
Ile Trp Asp Tyr Trp Glu Arg Asn Leu Asp Pro Asp Leu Phe Lys Asp
                355                 360                 365
Arg Thr Leu Lys Gly Thr Val Glu Gly Lys Val Cys Val Val Thr Gly
                370                 375                 380
Ala Thr Ser Gly Ile Gly Leu Ala Thr Ala Glu Lys Leu Ala Glu Ala
385                 390                 395                 400
Gly Ala Ile Leu Val Ile Gly Ala Arg Thr Lys Glu Thr Leu Asp Glu
                405                 410                 415
Val Ala Ala Ser Leu Glu Ala Lys Gly Gly Asn Val His Ala Tyr Gln
                420                 425                 430
Cys Asp Phe Ser Asp Met Asp Asp Cys Asp Arg Phe Val Lys Thr Val
                435                 440                 445
Leu Asp Asn His Gly His Val Asp Val Leu Val Asn Asn Ala Gly Arg
                450                 455                 460
Ser Ile Arg Arg Ser Leu Ala Leu Ser Phe Asp Arg Phe His Asp Phe
465                 470                 475                 480
Glu Arg Thr Met Gln Leu Asn Tyr Phe Gly Ser Val Arg Leu Ile Met
                485                 490                 495
Gly Phe Ala Pro Ala Met Leu Glu Arg Arg Gly His Val Val Asn
                500                 505                 510
```

```
Ile Ser Ser Ile Gly Val Leu Thr Asn Ala Pro Arg Phe Ser Ala Tyr
        515                 520                 525

Val Ala Ser Lys Ser Ala Leu Asp Ala Phe Ser Arg Cys Ala Ala Ala
        530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
                580                 585                 590

Tyr Arg Pro Lys Arg Ile Ala Thr Arg Leu Gly Val Phe Ala Gln Val
        595                 600                 605

Leu His Ala Leu Ala Pro Lys Met Gly Glu Ile Ile Met Asn Thr Gly
        610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr
            660
```

METHOD FOR THE PRODUCTION OF ISOAMYL ALCOHOL

CROSS-REFERENCE TO RELATED APPLICATIONS

This application is a § 371 National Stage Application of PCT/EP2016/064504 filed on Jun. 23, 2016, which claims priority to EP 15174104.8 filed on Jun. 26, 2015. All of these documents are hereby incorporated by reference in their entirety.

The present invention relates to a method for the production isoamyl alcohol (2-methylbutan-1-ol) comprising the enzymatic conversion of 3-methylbutyryl-CoA (isovaleryl-CoA) into isoamyl alcohol comprising: (a) two enzymatic steps comprising (i) first the enzymatic conversion of 3-methylbutyryl-CoA into 3-methylbutyraldehyde (3-methylbutanal or isovaleraldehyde); and (ii) then enzymatically converting the thus obtained 3-methylbutyraldehyde into said isoamyl alcohol; or (b) a single enzymatic reaction in which 3-methylbutyryl-CoA is directly converted into isoamyl alcohol by making use of an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84). Further, the present invention relates to the above method wherein the 3-methylbutyryl-CoA can be provided by the enzymatic conversion of 3-methylcrotonyl-CoA into said 3-methylbutyryl-CoA as described herein. The thus obtained isoamyl alcohol can be further enzymatically converted into 3-methylbutyl acetate (isoamyl acetate) as described herein. The present invention also relates to recombinant organisms or microorganisms which are capable of performing the above enzymatic conversions. Furthermore, the present invention relates to uses of enzymes and enzyme combinations which allow the above enzymatic conversions.

Isoamyl alcohol (also termed 3-methylbutan-1-ol or isopentanol) is an aliphatic alcohol. Isoamyl alcohol is a very important chemical commonly used as solvent for fats, oils, resins and alkaloids. There is a demand for isoamyl alcohol in perfumery industry, for example in the manufacture of isoamyl salicylate used in soap and cosmetic fragrances. It is also used in the manufacture of phosphoric acid. Furthermore, it is used in the synthesis of pyrethroids. Isoamyl alcohol is also used as raw material for the preparation of synthetic apricot, banana, cherry, greengage, malt, orange, plum and whiskey flavours, and in the production of synthetic banana oil. Various derivatives of isoamyl alcohol, i.e., isoamyl esters are used as fragrances as, e.g., isoamyl acetate, isoamyl acetoacetate, isoamyl benzoate, isoamyl butyrate, isoamyl cinnamate, isoamyl formate, isoamyl 2-furanbutyrate; [alpha]-isoamyl furfurylpropionate, isoamyl 2-furanpropionate, [alpha]-isoamyl furfurylacetate, isoamyl hexanoate, isoamyl isobutyrate, isoamyl isovalerate, isoamyl laurate, isoamyl-2-methylbutyrate, isopentyl-2-methyl butyrate, isoamyl nonanoate, isoamyl octanoate, isoamyl phenylacetate and isoamyl propionate.

Commercial processes for the production of isoamyl alcohol include fractionation of fusel oils, chlorination of alkanes with subsequent hydrolysis to produce a mixture of isomers and a low pressure oxo-process or hydroformylation of n-butenes followed by hydrogenation of the resulting isovaleraldehyde.

A way to biosynthesize isoamyl alcohol has recently been described (WO 2011/076261). More specifically, in WO 2011/076261, a method for the production of isoamyl alcohol is described comprising a method for the production of isoprenol using mevalonate as a substrate and enzymatically converting it by a decarboxylation step into isoprenol and further comprising the step of converting the thus produced isoprenol into isoamyl alcohol.

Moreover, the microbial production of esters, including isoamyl acetate from isoamyl alcohol and acetyl-CoA has recently been described (WO 2015/031859). More specifically, it has been described that isoamyl alcohol is biosynthesized from α-ketoisocaproate via 3-methylbutyraldehyde by making use of an α-keto acid decarboxylase (2-keto acid decarboxylase) and a subsequent reaction utilizing an alcohol dehydrogenase catalyzing the conversion of 3-methylbutyraldehyde into isoamyl alcohol while it is also described that said isoamyl alcohol may then further enzymatically be converted into isoamyl acetate.

Recently, genes, metabolic pathways, microbial strains and methods to produce the compound isoamyl alcohol from renewable feedstock utilizing a natural occurring metabolic pathway have been described while this compound has been suggested as an advanced biofuel (WO 2009/076480). Moreover, the biosynthesis of isoamyl alcohol from glucose has recently been described in engineered *E. coli* cells utilizing the host's amino acid biosynthetic pathways including the anabolic pathway for L-leucine; Appl. Environ. Microbiol. 74 (2008), 5769-5775; Appl. Microbiol. Biotechnol. 86 (2010), 1155-1164. The key step of these natural metabolic pathways include the decarboxylation of an alpha-keto acid (2-keto-isocaproate) into 3-methylbutanal as it is illustrated in FIG. 1. Yet, in the prior art, these metabolic engineered strains utilizing the native pathways are known to produce levels of isoamyl alcohol which are still too low for immediate industrial applications.

Another reason for the increasing demand of isoamyl alcohol is the fact that isoamyl alcohol may also be used as a starting molecule for the production of isoamyl acetate. Isoamyl acetate, also known as isopentyl acetate, is an organic compound that is the ester formed from isoamyl alcohol and acetic acid. It is a colourless liquid that is only slightly soluble in water, but very soluble in most organic solvents. Isoamyl acetate has a strong odour which is also described as similar to both banana and pear. Isoamyl acetate is particularly used to confer banana flavour in, e.g., foods. The bioconversion of exogenous isoamyl alcohol into isoamyl acetate has recently been described in modified *E. coli* by making use of the *S. cerevisiae* gene ATF2 (alcohol O-acetyl transferase) (Appl. Microbiol. Biotechnol. 63 (2004), 698-704). In this bioconversion, isoamyl alcohol and acetyl-CoA are coupled to result in the ester form, i.e., isoamyl acetate. Isoamyl acetate is not only widely used in the flavour industry given the characteristic banana aroma, but may also be used as a biodiesel.

Accordingly, given the numerous applications of isoamyl alcohol (and isoamyl acetate) there is an increasing demand for this compound. Thus, there is an increasing need to provide alternative methods for the environmentally friendly, cost efficient and simple production of isoamyl alcohol (and isoamyl acetate).

The present invention meets this demand for an alternative process for the enzymatic production of isoamyl acetate and, in particular, its precursor isoamyl alcohol which allows producing isoamyl alcohol (and isoamyl acetate) in vitro or in vivo in a microorganism and in other species, in particular by providing the subject-matter as recited in the claims.

Therefore, the present invention relates to a method for the production isoamyl alcohol (3-methylbutan-1-ol) comprising the enzymatic conversion of 3-methylbutyryl-CoA into isoamyl alcohol comprising: (a) two enzymatic steps comprising (i) first the enzymatic conversion of 3-methylbutyryl-CoA into 3-methylbutyraldehyde; and (ii) then enzymatically converting the thus obtained 3-methylbutyraldehyde into said isoamyl alcohol; or (b) a single enzymatic reaction in which 3-methylbutyryl-CoA is directly converted into isoamyl alcohol by making use of an alcohol-forming short chain acyl-CoA dehydrogenase/fatty acyl-CoA reductase.

The present invention not only relates to a method for the production of isoamyl alcohol from 3-methylbutyryl-CoA. Rather, this conversion is preferably embedded in a pathway for the production of isoamyl alcohol (and/or isoamyl acetate; also termed 3-methylbutyl acetate) starting from acetyl-CoA which is a central component and an important key molecule in metabolism used in many biochemical reactions.

Therefore, the present invention also relates to a pathway starting from acetyl-CoA wherein two acetyl-CoA molecules are enzymatically condensed into acetoacetyl-CoA which can further enzymatically be converted into 3-hydroxy-3-methylglutaryl-CoA. Further, 3-hydroxy-3-methylglutaryl-CoA can enzymatically be converted into 3-methylglutaconyl-CoA. Moreover, the thus produced 3-methylglutaconyl-CoA can further enzymatically be converted into 3-methylcrotonyl-CoA (also termed 3-methylbut-2-enoyl-CoA). Further, the thus produced 3-methylcrotonyl-CoA can enzymatically be converted into 3-methylbutyryl-CoA (also termed isovaleryl-CoA). The produced 3-methylbutyryl-CoA can enzymatically be converted into isoamyl alcohol via alternative routes. In one alternative, the produced 3-methylbutyryl-CoA can enzymatically be converted into 3-methylbutyraldehyde (also termed 3-methylbutanal or isovaleraldehyde). The thus produced 3-methylbutyraldehyde can enzymatically be converted into isoamyl alcohol (also termed 3-methylbutanol or isopentanol). Alternatively, the produced 3-methylbutyryl-CoA can directly be converted into isoamyl alcohol by a single enzymatic reaction. The thus produced isoamyl alcohol can be converted into isoamyl acetate. The corresponding reactions are schematically shown in FIG. 2.

Figure 2:
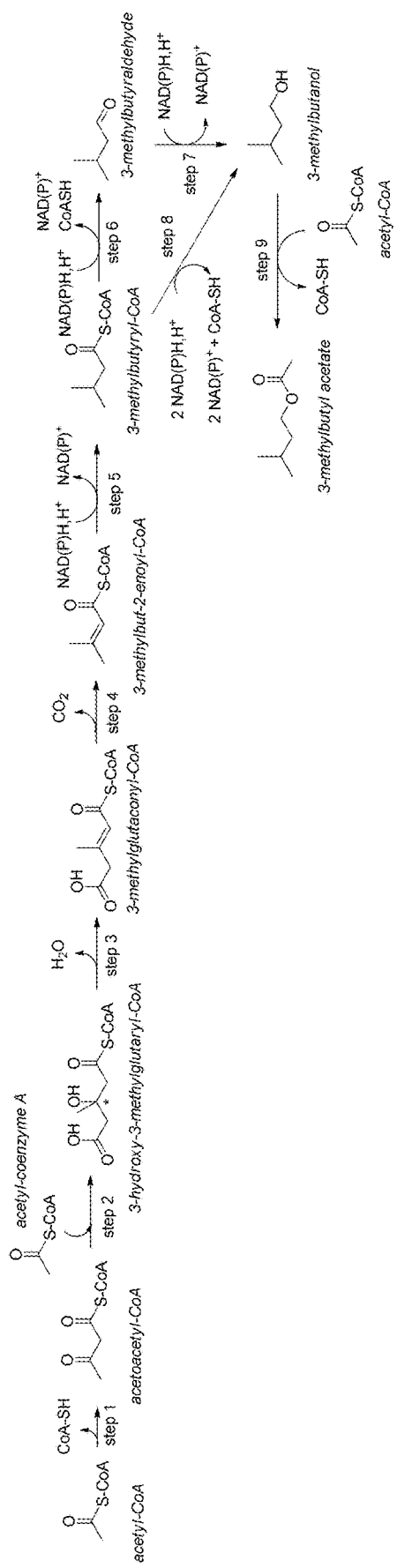

Parts of the reactions as schematically shown in FIG. 2 are already known. The biosynthesis of 3-methylbutyryl-CoA from acetyl-CoA has recently been described (Angew. Chem. Int. Ed. 52 (2013), 1304-1308) while the reverse biosynthetic pathway from 3-methylbutyryl-CoA to acetyl-CoA is known to occur in *Pseudomonas* (FEMS Microbiol. Lett. 286 (2008), 78-84).

The Enzymatic Conversion of 3-Methylbutyryl-CoA into Isoamyl Alcohol (Steps 6 and 7 or Step 8 in FIG. 2)

Figure 3:
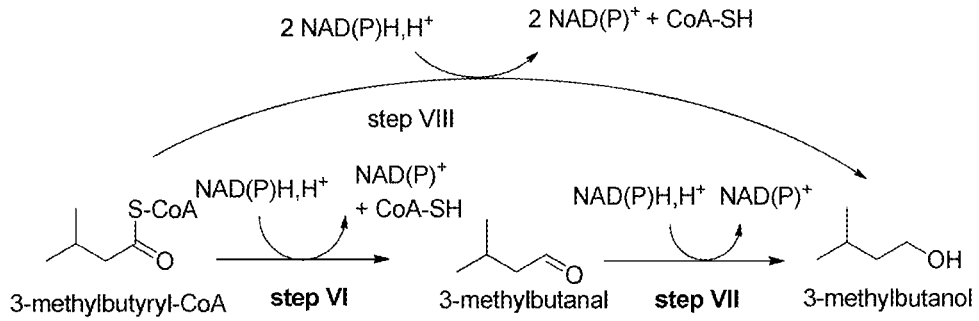

The present invention relates to a method for the production of isoamyl alcohol (3-methylbutan-1-ol) comprising the enzymatic conversion of 3-methylbutyryl-CoA into isoamyl alcohol. According to the present invention, the enzymatic conversion of 3-methylbutyryl-CoA into isoamyl alcohol can be achieved via different routes. One possibility is a two-step conversion via 3-methylbutyraldehyde. Another option involves a direct conversion of 3-methylbutyryl-CoA into isoamyl alcohol. These options will be outlined in the following and these reactions are schematically illustrated in FIG. 3.

Thus, the present invention relates to a method for the production of isoamyl alcohol (3-methylbutan-1-ol) comprising the enzymatic conversion of 3-methylbutyryl-CoA into isoamyl alcohol comprising:
(a) two enzymatic steps comprising
 (i) first the enzymatic conversion of 3-methylbutyryl-CoA into 3-methylbutyraldehyde (step 6 in FIG. 2); and
 (ii) then enzymatically converting the thus obtained 3-methylbutyraldehyde into said isoamyl alcohol (step 7 in FIG. 2); or
(b) a single enzymatic reaction in which 3-methylbutyryl-CoA is directly converted into isoamyl alcohol by making use of an alcohol-forming short chain acyl-CoA dehydrogenase/fatty acyl-CoA reductase (step 8 in FIG. 2).

Thus, in one embodiment, the enzymatic conversion of 3-methylbutyryl-CoA into isoamyl alcohol can be achieved by a two-step conversion via 3-methylbutyraldehyde. Accordingly, in one embodiment, the enzymatic conversion 3-methylbutyryl-CoA into isoamyl alcohol is achieved by two enzymatic steps comprising (i) first the enzymatic conversion of 3-methylbutyryl-CoA into 3-methylbutyraldehyde (step 6 as illustrated in FIG. 2); and (ii) then enzymatically converting the thus obtained 3-methylbutyraldehyde into said isoamyl alcohol (step 7 as illustrated in FIG. 2). This first alternative for the production of isoamyl alcohol via the two step conversion is described in the following while the second alternative, i.e., the direct conversion of 3-methylbutyryl-CoA into isoamyl alcohol is described further below.

The Enzymatic Conversion of 3-Methylbutyryl-CoA into 3-Methylbutyraldehyde (Step 6 in FIG. 2)

In a preferred embodiment, the present invention relates to a method for the production of isoamyl alcohol, wherein the enzymatic conversion of said 3-methylbutyryl-CoA into said 3-methylbutyraldehyde according to the above (i) (step 6 in FIG. 2) is achieved by making use of an enzyme which is classified as EC 1.2.1.-. These enzymes are oxidoreductases which catalyze the oxidation by acting on the aldehyde or oxo group of donors with $NAD^+$ or $NADP^+$ as acceptor and which are also able to catalyze the reverse reaction, i.e., the reduction of a CoA thioester group of acyl-CoA using NADH or NADPH as cofactor. In the context of the present invention in the enzymatic conversion of 3-methylbutyryl-CoA into 3-methylbutyraldehyde use is made of the reductase activity of such an enzyme.

Figure 4:
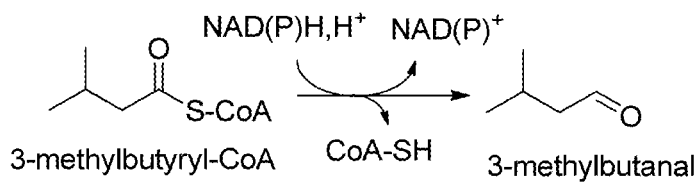

In this reaction, the Coenzyme A thioester of 3-methylbutyryl-CoA, by using NADH or NADPH as donor, is reduced into the corresponding aldehyde, i.e., 3-methylbutyraldehyde (which is also termed 3-methylbutanal or isovaleraldehyde). The corresponding reaction can be achieved by the use of an enzyme which is classified as (EC 1.2.1.-) and which is an oxidoreductase acting on the CoA thioester group of acyl-CoA as acceptor with NADH or NADPH as donor. This reaction is schematically illustrated in FIG. 4.

In a preferred embodiment, the conversion of 3-methylbutyryl-CoA into said 3-methylbutyraldehyde is achieved by the use of an acetaldehyde dehydrogenase (acetylating) (EC 1.2.1.10) or a propanal dehydrogenase (CoA-propanoylating) (EC 1.2.1.87).

Acetaldehyde dehydrogenases (acetylating) (EC 1.2.1.10) naturally catalyze the following reaction

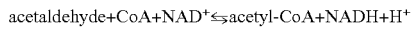
acetaldehyde+CoA+$NAD^+$⇌acetyl-CoA+NADH+$H^+$

This enzyme has been described to occur in a number of organisms, in particular in bacteria. In one embodiment, the enzyme is from a bacterium of the genus *Acinetobacter, Burkholderii, Clostridium, Escherichia, Giardia, Leuconostoc, Propionibacterium, Pseudomonas* or *Thermoanaerobacter*. In a preferred embodiment, the enzyme is from a bacterium of the species *Acinetobacter* sp. HBS-2 (UniProt Accession number A5JT11), *Burkholderia xenovorans* (UniProt Accession number Q79AF6), *Clostridium beijerinckii, Clostridium klyveri, E. coli, Giardia intestinalis, Leuconos-*

*toc mesenteroides* (SwissProt Accession number Q5RLY6), *Propionibacterium freudenreichii*, *Pseudomonas* sp. (SwissProt Accession number Q52060) or *Thermoanaerobacter ethanolicus*.

Propanal dehydrogenases (CoA-propanoylating) (EC 1.2.1.87) naturally catalyze the following reaction

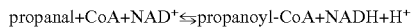

These enzymes are often encoded by the pduP gene and have been described to occur in a number of organisms, in particular in bacteria. The pduP gene is part of the propanediol (pdu) operon which is involved in the utilization of propanediol (J. Bacteriol. 181 (1999), 5967-5975). The pathway of 1,2-propanediol degradation starts with the conversion of 1,2-propanediol to propionaldehyde by an AdoCbl-dependent propanediol dehydratase (as derivable under the InterPro accession numbers IPR003207, IPR003208, or IPR009204 in the InterPro database of protein families). Propionaldehyde is subsequently oxidized by propionaldehyde dehydrogenase to form propionyl-CoA. Subsequently, propionyl-CoA can be metabolized either aerobically into pyruvate (presumably in three steps) or anaerobically into propionate (presumably in two steps) (J. Bacteriol. 179 (1997), 1013-1022). PduP is closely related to EutE and is assumed to be a CoA-dependent aldehyde dehydrogenase used in the pdu pathway for the conversion of propionaldehyde to propionyl-CoA (J. Bacteriol. 181 (1999), 5967-5975).

In one embodiment, the enzyme is from a bacterium of the genus *Burkholderia* or *Thermus*. In a preferred embodiment, the enzyme is from a bacterium of the species *Burkholderia xenovarans* (UniProt Accession number Q79AF6) or *Thermus thermophilus* (UniProt Accession number Q53WH9). In a more preferred embodiment, the enzyme is from a bacterium of the species *Klebsiella pneumonia* subsp. *pneumoniae* (strain ATCC 700721/MGH 78578) (i.e., the CoA-dependent propionaldehyde dehydrogenase from *Klebsiella pneumonia*; Uniprot Accession number A6TDE3) or *Salmonella typhimurium* (i.e., the CoA-acylating propionaldehyde dehydrogenase from *Salmonella typhimurium*; Uniprot Accession number H9L4I6).

The sequence of the propanal dehydrogenase (CoA-propanoylating)/CoA-dependent propionaldehyde dehydrogenase from *Klebsiella pneumonia* subsp. *pneumoniae* (strain ATCC 700721/MGH 78578) is shown in SEQ ID NO: 9. The sequence of the propanal dehydrogenase (CoA-propanoylating)/CoA-acylating propionaldehyde dehydrogenase from *Salmonella typhimurium* is shown in SEQ ID NO: 10. In a particularly preferred embodiment any protein showing an amino acid sequence as shown in SEQ ID NO: 9 or SEQ ID NO: 10 or showing an amino acid sequence which is at least 80% homologous to in SEQ ID NO: 9 or SEQ ID NO: 10 and having the activity of a propanal dehydrogenase (CoA-propanoylating) wherein such an enzyme is capable of catalyzing the enzymatic conversion of 3-methylbutyryl-CoA into 3-methylbutyraldehyde can be employed in a method according to the present invention.

In a preferred embodiment such an enzyme has an amino acid sequence as shown in SEQ ID NO: 9 or SEQ ID NO: 10 or shows an amino acid sequence which is at least x % homologous to SEQ ID NO: 9 or SEQ ID NO: 10 and has the activity of a propanal dehydrogenase (CoA-propanoylating) with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylbutyryl-CoA into said 3-methylbutyraldehyde as set forth herein above.

As regards the determination of sequence identity, the following should apply: When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Amino acid residues located at a position corresponding to a position as indicated herein-below in the amino acid sequence shown in any one of SEQ ID NOs:9 and 10 can be identified by the skilled person by methods known in the art. For example, such amino acid residues can be identified by aligning the sequence in question with the sequence shown in any one of SEQ ID NOs:9 and 10 and by identifying the positions which correspond to the above indicated positions of any one of SEQ ID NOs:9 and 10. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

The Enzymatic Conversion of 3-Methylbutyraldehyde into Isoamyl Alcohol (Step 7 in FIG. 2)

In a preferred embodiment, the present invention relates to a method for the production of isoamyl alcohol, wherein the enzymatic conversion of said 3-methylbutyraldehyde into said isoamyl alcohol according to the above (ii) (step 7 of FIG. 2) is achieved by making use of an enzyme which is classified as EC 1.1.1.-. These enzymes are oxidoreductases which catalyze the oxidation of the CH—OH group of donors with $NAD^+$ or $NADP^+$ as acceptor and which are also able to catalyze the reverse reaction, i.e., the reduction of the aldehyde or keto group (—CH=O, C=O) using NADPH or NADH as cofactor. In the context of the present invention in the enzymatic conversion of 3-methylbutyraldehyde into isoamyl alcohol use is made of the reductase activity of such an enzyme. Thus, in the context of the present invention, an enzyme which is classified as EC 1.1.1.- is an oxidoreductase acting on the aldehyde group as acceptor with NADH and NADPH as donor.

In this reaction, the carbonyl group of 3-methylbutyrylaldehyde is reduced into its corresponding alcohol, i.e., isoamyl alcohol (also termed 3-methylbutanol or isopentanol) by making use of an oxidoreductase (reductase activity) acting on the carbonyl group of 3-methylbutyrylaldehyde with NADH or NADPH as hydride donor (EC 1.1.1.-). The enzymatic conversion of 3-methylbutyraldehyde into isoamyl alcohol has already been described in Appl. Environ. Microbiol. 74 (2008), 5769-5775 to naturally occur by a methylbutanal reductase (EC 1.1.1.265).

Figure 5:
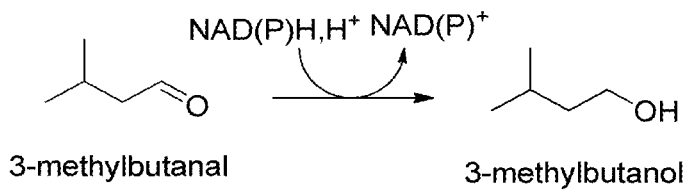

The reaction is schematically illustrated in FIG. 5.

Thus, in a preferred embodiment, the enzymatic conversion of said 3-methylbutyraldehyde into said isoamyl alcohol is achieved by the use of a methylbutanal reductase (EC 1.1.1.265). In other preferred embodiments, the enzymatic conversion of said 3-methylbutyraldehyde into said isoamyl alcohol is achieved by the use of an alcohol dehydrogenase (EC 1.1.1.1) or an NADP dependent alcohol dehydrogenase (EC 1.1.1.2).

Methylbutanal reductases (EC 1.1.1.265) naturally catalyze the following reaction

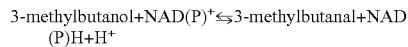

3-methylbutanol+NAD(P)$^+$⇌3-methylbutanal+NAD(P)H+H$^+$

This enzyme has been described to occur in a number of organisms, in particular eukaryotes. In a preferred embodiment, the enzyme is from a fungus, more preferably from a yeast. In a further preferred embodiment, the enzyme is from the genus *Candida* or *Sacharomyces*. In a more preferred embodiment, the enzyme is from a fungus of the species *Candida boidinii, Saccharomyces cerevisiae, Saccharomyces bayanus* or *Saccharomyces ludwigii*.

Alcohol dehydrogenases (EC 1.1.1.1) naturally catalyze the following reaction

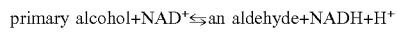

primary alcohol+NAD$^+$⇌an aldehyde+NADH+H$^+$

This enzyme has been described to occur in a number of organisms, in particular bacteria and eukaryotes. In one preferred embodiment, the enzyme is from a bacterium, preferably from a bacterium of the genus *Aeropyrum, Brevibacterium, Corynebacterium, Flavobacterium, Geobacillus, Haloferax, Klebsiella, Pseudomonas, Pyrococcus, Rhodococcus, Sulfolobus, Thermoanaerobacter, Thermoplasma, Thermus* or *Zymomoas*, more preferably from a bacterium of the species *Aeropyrum pernix* (UniProt Accession number Q9Y9P9), *Brevibacterium* sp., *Corynebacterium glutamicum, Flavobacterium frigidimaris* (SwissProt Accession number Q8L3C9), *Geobacillus stearothermophilus* (UniProt Accession number P42328), *Haloferax volcanii, Klebsiella oxytoca, Klebsiella pneumoniae, Pseudomonas aeruginosa, Pseudomonas fluorescens, Pseudomonas putida* (UniProt Accession number Q76HN6), *Pyrococcus furiosus* (SwissProt Q8U259), *Rhodococcus erythropolis, Rhodococcus ruber, Sulfolobus acidocaldarius* (UniProt Accession number Q4J9F2), *Sulfolobus solfataricus* (UniProt Accession number P39462), *Thermoanaerobacter brockii, Thermoanaerobacter ethanolicus* (UniProt Accession number Q0PH30), *Thermoplasma acidophilum* (UniProt Accession number Q9HIM3), *Thermus* sp. (UniProt Accession number B2ZRE3) or *Zymomonas mobilis*.

In another embodiment, the enzyme is from a eukaryote. In one preferred embodiment, the enzyme is from the genus *Bombyx, Drosophila, Gallus, Homo, Mus* or *Rattus*, more preferably from the species *Bombyx mori, Drosophila funebris, Drosophila melanogaster, Drosophila virilis, Drosophila simulans, Gallus gallus, Homo sapiens* (UniProt Accession number P00326 or P08319), *Mus musculus* (UniProt Accession number Q9QYY9) or *Rattus norvegicus*.

In another embodiment, the enzyme is from yeast, preferably *Saccharomyces* or *Schizosaccharomyces*, more preferably from the species *Saccharomyces carlsbergensis* (UniProt accession number B6UQD0), *Saccharomyces cerevisiae* (UniProt Accession number P00331) or *Schizosaccharomyces pombe* (SwissProt Accession number Q09669).

In another embodiment, the enzyme is from a fungus, preferably *Candida* or *Neurospora*, more preferably of the species *Candida maris, Candida parapsilosis* (UniProt Accession number B2KJ46) or *Neurospora grassa* (SwissProt Accession number Q9P6C8).

In another embodiment, the enzyme is from a plant or an algae, preferably from the genus *Chlamydomonas, Glycine, Oryza, Vica* or *Zea* even more preferably from the species *Chlamydomonas moewusii, Glycine max* (UniProt Accession number D4GSN2), *Oryza sativa, Vica faba* or *Zea mays*.

In another embodiment, the enzyme is from an organism of the genus *Entamoeba*, more preferably from the species *Entamoeba histolytica*.

NADP-dependent alcohol dehydrogenases (EC 1.1.1.2) naturally catalyze the following reaction

a primary alcohol+NADP$^+$⇌an aldehyde+NADPH+H$^+$

This enzyme has been described to occur in a number of organisms, in particular bacteria and eukaryotes. In one preferred embodiment, the enzyme is from a bacterium, preferably from a bacterium of the genus *Acetobacter, Acinetobacter, Bacillus, Brevibacillus, Clostridium, Escherichia, Geobacillus, Haloferax, Heliobacter, Lactobacillus, Leuconostoc, Methanobacterium, Mycobacterium, Pseudomonas, Pyrobaculum, Pyrococcus, Thermoanaerobacter* or *Thermococcus* more preferably from a bacterium of the species *Acetobacter aceti, Acinetobacter calcoaceticus, Bacillus methanolicus, Bacillus subtilis, Brevibacillus brevis, Clostridium acetobutylicum, Clostridium beijerinckii, Clostridium kluyveri, Clostridium thermocellum, Escherichia coli, Geobacillus stearothermophilus, Haloferax volcanii, Helicobacter pylori, Lactobacillus brevis, Lactobacillus kefiri, Leuconostoc mesenteroides, Methanobacterium palustre, Mycobacterium avium, Mycobacterium bovis, Mycobacterium leprae, Mycobacterium smegmatis, Mycobacterium tuberculosis, Pseudomonas aeruginosa, Pyrobaculum aerophilum* (UniProt Accession number Q8ZUP0), *Pyrococcus furiosus* (UniProt Accession number O73949), *Thermoanaerobacter brockii, Thermoanaerobacter ethanolicus, Thermoanaerobacter thermohydrosulfuricus, Thermococcus litoralis, Thermococcus sibiricus* (SwissProt C6A190) or *Thermococcus* sp. (UniProt Accession number C1IWT4).

In a particularly preferred embodiment, the NADP-dependent alcohol dehydrogenase (EC 1.1.1.2) is the NADP-dependent alcohol dehydrogenase from *Mycobacterium smegmatis* (Uniprot accession number P0CH36).

In another embodiment, the enzyme is from a eukaryote. In one preferred embodiment, the enzyme is from the genus *Bos, Drosophila, Felis, Homo, Mus, Rattus* or *Sus*, more preferably of the species *Bos taurus, Drosophila melanogaster, Felis* sp., *Homo sapiens* (UniProt Accession number P14550), *Mus musculus* (SwissProt Accession number 09J116), *Rattus norvegicus* or *Sus scrofa* (UniProt Accession number P50578).

In another embodiment, the enzyme is from a fungus, preferably from a fungus of the genus *Candida, Kluyveromyces, Saccharomyces* or *Schizosaccharomyces*, more preferably from the species *Candida tropicalis, Kluyveromyces lactis* (UniProt Accession number P49384), *Saccharomyces cerevisiae* or *Schizosaccharomyces pombe*.

In another embodiment, the enzyme is from an organism of the genus *Entamoeba*, more preferably of the species *Entamoeba histolytica*.

The Enzymatic Conversion of 3-Methylbutyryl-CoA into Isoamyl Alcohol (Step 8 in FIG. 2)

As mentioned above, the present invention relates to a method for the production of isoamyl alcohol (3-methylbutan-1-ol) comprising the enzymatic conversion of 3-methylbutyryl-CoA into isoamyl alcohol wherein in an alternative possibility to the above, 3-methylbutyryl-CoA is directly converted into isoamyl alcohol. Thus, similar to the above described conversion of 3-methylbutyryl-CoA into isoamyl alcohol which proceeds via 3-methylbutyraldehyde, in an alternative possibility, this two-step reaction is catalyzed by one enzyme which catalyzes both reduction steps. An enzyme which may be employed in this conversion is a short-chain acyl-CoA dehydrogenase/fatty acyl-CoA reductase or an alcohol-forming fatty acyl-CoA reductase which is also termed long-chain acyl-CoA:NADPH reductase (EC 1.2.1.84). In Example 2, various individual enzymes from different organisms have been tested with respect to their capability to directly convert 3-methylbutyryl-CoA into isoamyl alcohol and in Example 2, these enzymes are collectively abbreviated with the term "SDR reductase".

Thus, the present invention relates to a method for the production isoamyl alcohol (3-methylbutan-1-ol) comprising the enzymatic conversion of 3-methylbutyryl-CoA into isoamyl alcohol comprising: (b) a single enzymatic reaction in which 3-methylbutyryl-CoA is directly converted into isoamyl alcohol by making use of an alcohol-forming short chain acyl-CoA dehydrogenase/fatty acyl-CoA reductase or an alcohol-forming acyl-CoA reductase (long-chain acyl-CoA:NADPH reductase) (EC 1.2.1.84) (step 8 as illustrated in FIG. 2).

Figure 6:
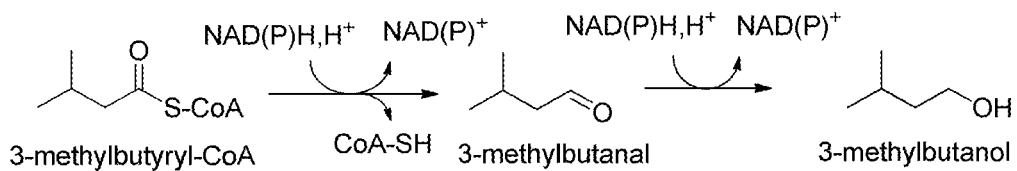

Thus, the two reductions as illustrated in FIG. 6, i.e., the enzymatic conversion of 3-methylbutyryl-CoA into isoamyl alcohol (3-methylbutan-1-ol) via 3-methylbutyraldehyde, are catalyzed by a single enzyme. In one preferred embodiment, the direct conversion of 3-methylbutyryl-CoA into isoamyl alcohol can be achieved by making use of an alcohol-forming short chain acyl-CoA dehydrogenase/fatty acyl-CoA reductase.

Alcohol-forming short chain acyl-CoA dehydrogenase/fatty acyl-CoA reductases which can be employed for catalyzing the enzymatic conversion of 3-methylbutyryl-CoA into isoamyl alcohol (3-methylbutan-1-ol) via 3-methylbutyraldehyde, also referred to as "short-chain dehydrogenase/fatty acyl-CoA reductase" or "short-chain dehydrogenases/reductases (SDR)", in the context of the present invention refer to enzymes which are characterized by the features that they catalyze a two-step reaction in which fatty acyl-CoA is reduced to fatty alcohol and that they show a substrate specificity for acyl-CoA containing aliphatic carbon chains.

The short-chain dehydrogenase/fatty acyl-CoA reductase or short-chain dehydrogenases/reductases (SDR) enzymes constitute a family of enzymes, most of which are known to be NAD- or NADP-dependent oxidoreductase (Jornvall H. et al., Biochemistry 34 (1995), 6003-6013). Recently, a novel bacterial NADP-dependent reductase from *Marinobacter aquaeolei* VT8 was characterized (Willis et al., Biochemistry 50 (2011), 10550-10558). This enzyme catalyzes the four-electron reduction of fatty acyl-CoA substrates to the corresponding fatty alcohols.

The enzymatic conversion of fatty acyl-CoA into fatty alcohol occurs through an aldehyde intermediate according to the following scheme:

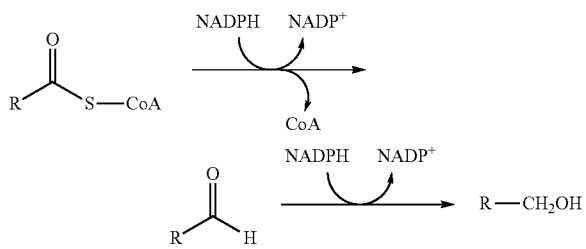

The enzyme displays activity on fatty acyl-CoA substrates (both saturated and unsaturated) as well as on fatty aldehyde substrates. Characteristically, proteins of this family possess two NAD(P)(H)-binding motifs, which have the conserved sequence GXGX(1-2X)G (Willis et al., Biochemistry 50 (2011), 10550-10558; Jornvall H. et al., Biochemistry 34 (1995), 6003-6013). The first pattern, GTGFIG, is identified near the N-terminus and the second signature sequence, GXXXGXG, is located between residues 384-390.

In principle any "short-chain dehydrogenase/fatty acyl-CoA reductase" or "short-chain dehydrogenases/reductases (SDR)" can be applied in the method according to the invention.

Preferably, the short-chain dehydrogenase/fatty acyl-CoA reductase is a short-chain dehydrogenase/fatty acyl-CoA reductase from a marine bacterium, preferably from the genus *Marinobacter* or *Hahella*, even more preferably from the species *Marinobacter aquaeolei*, more preferably *Marinobacter aquaeolei* VT8, *Marinobacter manganoxydans, Marinobacter algicola, Marinobacter* sp. ELB17 or *Hahella chejuensis*. Examples of such enzymes are the short-chain dehydrogenase/fatty acyl-CoA reductase from *Marinobacter aquaeolei* VT8 (Uniprot accession number A1U3L3; Willis et al., Biochemistry 50 (2011), 10550-10558), the short-chain dehydrogenase from *Marinobacter manganoxydans* (Uniprot accession number G6YQS9), the short-chain dehydrogenase from *Marinobacter algicola* (Uniprot accession number A6EUH6), the short-chain dehydrogenase from *Marinobacter* sp. ELB17 (Uniprot accession number A3JCC5), the short-chain dehydrogenase from *Hahella chejuensis* (Uniprot accession number Q2SCE0) and the short chain dehydrogenase/reductase from *Marinobacter hydrocarbonoclasticus* ATCC 49840 (Uniprot accession number H8W980).

The sequence of the short-chain dehydrogenase/fatty acyl-CoA reductase from *Marinobacter aquaeolei* VT8 (also termed *Marinobacter hydrocarbonoclasticus* (strain ATCC 700491/DSM 11845/VT8)) is shown in SEQ ID NO: 1. The sequence of the short-chain dehydrogenase/fatty acyl-CoA reductase from *Marinobacter manganoxydans* (also termed *Marinobacter manganoxydans* Mnl7-9) is shown in SEQ ID NO: 2. The sequence of the short-chain dehydrogenase/fatty acyl-CoA reductase from *Marinobacter sp. ELB17 is shown in SEQ ID NO: 3. The sequence of the short-chain dehydrogenase/fatty acyl-CoA reductase from *Marinobacter algicola* (also termed *Marinobacter algicola* DG893) is shown in SEQ ID NO: 4. The sequence of the short-chain dehydrogenase/fatty acyl-CoA reductase from *Hahella chejuensis* (also termed *Hahella chejuensis* (strain KCTC 2396)) is shown in SEQ ID NO: 11. The sequence of the short chain dehydrogenase/reductase from *Marinobacter hydrocarbonoclasticus* ATCC 49840 (Uniprot accession number H8W980) is shown in SEQ ID NO: 13. In a particularly preferred embodiment any protein showing an amino acid sequence as shown in any one of SEQ ID NOs: 1 to 4, 11, and 13 or showing an amino acid sequence which is at least 80% homologous to any of SEQ ID NOs: 1 to 4, 11 and 13 and having the activity of a short-chain dehydrogenase/fatty acyl-CoA reductase wherein such an enzyme is capable of catalyzing the enzymatic conversion of 3-methylbutyryl-CoA into 3-methylbutanol via 3-methylbutyraldehyde can be employed in a method according to the present invention.

In a preferred embodiment such an enzyme has an amino acid sequence as shown in any one of SEQ ID NOs: 1 to 4, 11 and 13 or shows an amino acid sequence which is at least x % homologous to any one of SEQ ID NOs:1 to 4, 11 and 13 and has the activity of a short-chain dehydrogenase/fatty acyl-CoA reductase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylbutyryl-CoA into 3-methylbutanol via 3-methylbutyraldehyde as set forth herein above.

As regards the determination of sequence identity, the same applies as has been set forth above.

In another preferred embodiment, the conversion of 3-methylbutyryl-CoA into isoamyl alcohol is catalyzed by making use of a short-chain dehydrogenase/reductase from a photoheterotrophic marine bacterium belonging to the genus *Erythrobacter* and using NADH or NADPH as cofactors, preferably by making use of a short-chain dehydrogenase/reductase from the photoheterotrophic marine bacterium *Erythrobacter* sp. NAP1 (Uniprot Accession Number: A3WE13). In another embodiment, the conversion of 3-methylbutyryl-CoA into isoamyl alcohol is catalyzed by making use of a short-chain dehydrogenase/reductase from a bacteria of the genus *Chloroflexus*, preferably by making use of a short-chain dehydrogenase/reductase from *Chloroflexus aggregans* strain MD-66/DSM 9485 (Uniprot Accession Number B8G7Y5).

As mentioned above, in another preferred embodiment, the direct conversion of 3-methylbutyryl-CoA into isoamyl alcohol can be achieved by making use of an alcohol-forming acyl-CoA reductase (long-chain acyl-CoA:NADPH reductase) (EC 1.2.1.84).

Alcohol-forming acyl-CoA reductases (long-chain acyl-CoA:NADPH reductase) (EC 1.2.1.84) naturally catalyze the following reaction:

a long-chain acyl-CoA+2NADPH+2H⁺⇌a long-chain alcohol+2NADP⁺+Coenzyme A

This enzyme occurs in a variety of organisms, in particular in eukaryotes. In a preferred embodiment, the enzyme is from a plant, preferably of a plant of the genus *Arabidopsis* or *Simmondsia*, more preferably from the species *Arabidopsis thaliana* (UniProt Accession number Q93ZB9, Q0WRB0, Q39152, or Q9LXN3) or from the species *Simmondsia chinensis* (UniProt Accession number Q9XGY7). In another preferred embodiment, the enzyme is from an animal, more preferably from a mammal, even more preferably from a rodent, particularly from a rodent of the genus *Cavia* or *Mus*. Preferred are the species *Cavia porcellus* and *Mus musculus* (SwissProt Accession number Q7TNT2 or Q922J9).

The Enzymatic Conversion of Isoamyl Alcohol into Isoamyl Acetate (Step 9 in FIG. 2)

As mentioned above, the isoamyl alcohol which is produced according to any of the methods described herein may further be converted into isoamyl acetate (also referred to as 3-methylbutyl acetate) by an enzymatic reaction, namely the enzymatic conversion of isoamyl alcohol into isoamyl acetate. The conversion of isoamyl alcohol into isoamyl acetate is schematically illustrated in FIG. 8.

Thus, the present invention also relates to a method for the production of isoamyl acetate in which 3-methylbutyryl-CoA is first converted into isoamyl alcohol as described herein above wherein said isoamyl alcohol is then further enzymatically converted into isoamyl acetate.

In a preferred embodiment, the enzymatic conversion of isoamyl alcohol into isoamyl acetate can be achieved by making use of any alcohol-O-acetyl-transferase (EC 2.3.1.84).

Alcohol-O-acetyl-transferases (EC 2.3.1.84) are enzymes which naturally catalyze the following reaction:

acetyl-CoA+a primary alcohol⇌CoA+an acetyl ester

This enzyme occurs in a variety of organisms, including eukaryotic and prokaryotic organisms such as plants and yeasts.

In a preferred embodiment, the enzyme is an enzyme from a fungus, more preferably from a yeast. Preferably, the enzyme is from an organism of the genus *Cyberlindnera*, *Hanseniaspora*, *Kluyveromyces*, *Wickerhamomyces* or *Saccharomyces*, more preferably from the species *Cyberlindnera mrakii*, *Hanseniaspora valbyensis*, *Kluyveromyces lactis*, *Wickerhamomyces anomalus*, *Saccharomyces pastorianus*, *Saccharomyces uvarum* or *Saccharomyces cerevisiae* (UniProt Accession number Q6XBT0).

The enzymatic condensation of exogenous isoamyl alcohol (3-methylbutan-1-ol) and endogenous acetyl-CoA into isoamyl acetate (3-methylbutyl acetate) in a modified *Escherichia coli* by using an alcohol-O-acetyl-transferase of *S. cerevisiae* has already been described (Appl. Microbiol. Biotechnol. 63 (2004), 698-704).

Thus, according to the present invention, the enzymatic conversion of isoamyl alcohol into isoamyl acetate is preferably achieved by an alcohol-O-acetyl-transferase of *S. cerevisiae*. In a particularly preferred embodiment, the enzyme is an alcohol-O-acetyl-transferase from *S. cerevisiae* which is encoded by the gene ATF2 (UniProt Accession number Q6XBT0). In another particularly preferred embodiment, the alcohol-O-acetyl-transferase encoded by the gene ATF2 is from another *S. cerevisiae* genotype which has the UniProt Accession number P53296).

In a preferred embodiment, the enzyme is an enzyme from a plant, preferably from the genus *Cucumis*, *Cymbopogon*, *Fragaria*, *Petunia*, *Rosa*, *Solanum*, *Malus*, *Vasconcellea* or *Musa*, more preferably from the species *Cucumis melo*, *Cymbopogon martini*, *Fragaria ananassa* (UniProt Accession number G1 EFQ3), *Petunia hybrida* (UniProt Accession number A1XWY7), *Rosa* hybrid cultivar (UniProt Accession number Q5I6B5), *Solanum lycopersicum*, *Vasconcellea cundinamarcensis* (UniProt Accession number D0QJ94), *Musa acuminate*, *Musa paradisiacal* or *Malus domestica*.

The Enzymatic Conversion of 3-Methylcrotonyl-CoA into 3-Methylbutyryl-CoA (Step 5 in FIG. 2)

The 3-methylbutyryl-CoA which is converted according to the present invention into isoamyl alcohol according to any of the above described methods (and further converted to isoamyl acetate according to any of the above described methods) may itself be provided by an enzymatic reaction, namely the enzymatic conversion of 3-methylcrotonyl-CoA (also referred to as 3-methylbut-2-enoyl-CoA) into 3-methylbutyryl-CoA. The conversion of 3-methylcrotonyl-CoA into 3-methylbutyryl-CoA is schematically illustrated in FIG. 7.

Thus, the present invention also relates to a method for producing isoamyl alcohol (or isoamyl acetate) from 3-methylcrotonyl-CoA in which 3-methylbutyryl-CoA is first provided by the enzymatic conversion of 3-methylcrotonyl-CoA into said 3-methylbutyryl-CoA. Further, 3-methylbutyryl-CoA is then further converted into isoamyl alcohol (or further to isoamyl acetate) as described herein above.

The enzymatic conversion of 3-methylcrotonyl-CoA into 3-methylbutyryl-CoA, i.e., the reduction of the double bond in 3-methylcrotonyl-CoA, can, for example, be achieved by employing an enzyme classified as EC 1.3._._. Enzymes classified as EC 1.3._._ are oxidoreductases acting on a CH—CH group. Sub-subclasses of EC 1.3._._ are classified depending on the acceptor. In one particular preferred embodiment, the enzyme is an enzyme which uses NAD+ or NADP+ as a co-substrate and which belongs to the EC 1.3.1._ sub-subclass.

Many oxidoreductases of the subgroup EC 1.3.1._ acting on carbon-carbon double bonds in the α,β-position in relation to a carbonyl group are known. Many of these enzymes catalyze the reduction of α,β-unsaturated ketones or CoA-esters. Thus, in a preferred embodiment, according to the present invention, the enzymatic conversion of 3-methylcrotonyl-CoA into said 3-methylbutyryl-CoA is achieved by making use of an enzyme which is classified as EC 1.3.1._ and which is an oxidoreductase acting on the C=C double bond of 3-methylcrotonyl-CoA with NADH or NADPH as hydride donors.

In one particularly preferred embodiment the enzyme is an enzyme which uses NADPH as a co-factor. The conversion using such an enzyme is schematically shown in FIG. 1. In a preferred embodiment the enzyme is selected from the group consisting of:
- acyl-CoA dehydrogenase (NADP+) (EC 1.3.1.8);
- enoyl-[acyl-carrier-protein] reductase (NADPH, Si-specific) (EC 1.3.1.10);
- cis-2-enoyl-CoA reductase (NADPH) (EC 1.3.1.37);
- trans-2-enoyl-CoA reductase (NADPH) (EC 1.3.1.38);
- enoyl-[acyl-carrier-protein] reductase (NADPH, Re-specific) (EC 1.3.1.39); and
- crotonyl-CoA reductase (EC 1.3.1.86).

Thus, in one preferred embodiment the conversion of 3-methylcrotonyl-CoA into 3-methylbutyryl-CoA is achieved by making use of an acyl-CoA dehydrogenase (NADP+) (EC 1.3.1.8). Acyl-CoA dehydrogenases are enzymes which catalyze the following reaction:

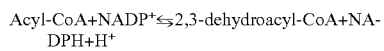
Acyl-CoA+NADP⁺⇌2,3-dehydroacyl-CoA+NADPH+H⁺

This enzyme occurs in a variety of organisms, including eukaryotic and prokaryotic organisms, such as plants, animals, fungi and bacteria. The enzyme has, e.g., been described in *Bos taurus, Rattus novegicus, Mus musculus, Columba* sp., *Arabidopsis thaliana, Nicotiana benthamiana, Allium ampeloprasum, Euglena gracilis, Candida albicans, Streptococcus collinus, Rhodobacter sphaeroides* and *Mycobacterium smegmatis*.

In a further preferred embodiment the conversion of 3-methylcrotonyl-CoA into 3-methylbutyryl-CoA is achieved by making use of an enoyl-[acyl-carrier-protein] reductase (NADPH, Si-specific) (EC 1.3.1.10). Enoyl-[acyl-carrier-protein] reductases (NADPH, Si-specific) are enzymes which catalyze the following reaction:

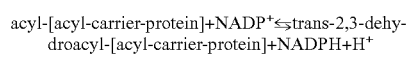
acyl-[acyl-carrier-protein]+NADP⁺⇌trans-2,3-dehydroacyl-[acyl-carrier-protein]+NADPH+H⁺

This enzyme occurs in a variety of organisms, including eukaryotic and prokaryotic organisms, such as plants, fungi and bacteria. The enzyme has, e.g., been described in *Carthamus tinctorius, Candida tropicalis, Saccharomyces cerevisiae, Streptococcus collinus, Streptococcus pneumoniae, Staphylococcus aureus, Bacillus subtilis, Bacillus cereus, Porphyromonas gingivalis, Escherichia coli* and *Salmonella enterica*.

In a further preferred embodiment the conversion of 3-methylcrotonyl-CoA into 3-methylbutyryl-CoA is achieved by making use of a cis-2-enoyl-CoA reductase (NADPH) (EC 1.3.1.37). Cis-2-enoyl-CoA reductases (NADPH) are enzymes which catalyze the following reaction:

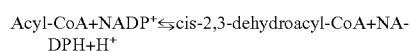
Acyl-CoA+NADP⁺⇌cis-2,3-dehydroacyl-CoA+NADPH+H⁺

This enzyme has been described to occur in *Escherichia coli*.

In a further preferred embodiment the conversion of 3-methylcrotonyl-CoA into 3-methylbutyryl-CoA is achieved by making use of a trans-2-enoyl-CoA reductase (NADPH) (EC 1.3.1.38). Trans-2-enoyl-CoA reductases (NADPH) are enzymes which catalyze the following reaction:

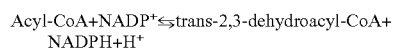
Acyl-CoA+NADP⁺⇌trans-2,3-dehydroacyl-CoA+NADPH+H⁺

This enzyme occurs in a variety of organisms, including eukaryotic and prokaryotic organisms, such as plants, animals and bacteria. The enzyme has, e.g., been described in *Homo sapiens, Rattus norvegicus, Mus musculus, Cavia porcellus, Caenorhabditis elegans, Phalaenopsis amabilis, Gossypium hirsutum, Mycobacterium tuberculosis, Streptococcus collinu* and *Escherichia coli*.

In a further preferred embodiment the conversion of 3-methylcrotonyl-CoA into 3-methylbutyryl-CoA is achieved by making use of an enoyl-[acyl-carrier-protein] reductase (NADPH, Re-specific) (EC 1.3.1.39). Enoyl-[acyl-carrier-protein] reductases (NADPH, Re-specific) are enzymes which catalyze the following reaction:

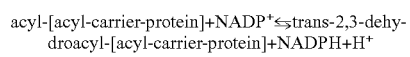
acyl-[acyl-carrier-protein]+NADP⁺⇌trans-2,3-dehydroacyl-[acyl-carrier-protein]+NADPH+H⁺

This enzyme occurs in a variety of organisms, including eukaryotic and prokaryotic organisms, such as animals and bacteria. The enzyme has, e.g., been described in *Gallus gallus*, Pigeon, *Rattus norvegicus, Cavia porcellus, Staphylococcus aureus, Bacillus subtilis* and *Porphyromonas gingivalis*.

In a further preferred embodiment the conversion of 3-methylcrotonyl-CoA into 3-methylbutyryl-CoA is achieved by making use of a crotonyl-CoA reductase (EC 1.3.1.86). Crotonyl-CoA reductases are enzymes which catalyze the following reaction:

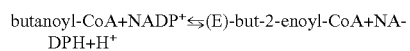
butanoyl-CoA+NADP⁺⇌(E)-but-2-enoyl-CoA+NADPH+H⁺

This enzyme occurs in a variety of organisms, including eukaryotic and prokaryotic organisms, such as animals, fungi and bacteria. The enzyme has, e.g., been described in *Bos taurus, Salinospora tropica, Clostridium difficile, Streptomyces collinus, Streptomyces cinnamonensis* and *Streptomyces hygroscopicus*.

In another particularly preferred embodiment the enzyme is an enzyme which uses NADH as a co-factor. The conversion using such an enzyme is schematically shown in FIG. 2. In a preferred embodiment the enzyme is selected from the group consisting of:
 enoyl-[acyl-carrier-protein] reductase (NADH) (EC 1.3.1.9); and
 trans-2-enoyl-CoA reductase (NAD⁺) (EC 1.3.1.44).

Thus, in one preferred embodiment the conversion of 3-methylcrotonyl-CoA into 3-methylbutyryl-CoA is achieved by making use of an enoyl-[acyl-carrier-protein] reductase (NADH) (EC 1.3.1.9). Enoyl-[acyl-carrier-protein] reductases (NADH) are enzymes which catalyze the following reaction:

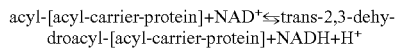

acyl-[acyl-carrier-protein]+NAD⁺⇌trans-2,3-dehydroacyl-[acyl-carrier-protein]+NADH+H⁺

This enzyme occurs in a variety of organisms, including eukaryotic and prokaryotic organisms, such as plants and bacteria. The enzyme has, e.g., been described in *Arabidopsis thaliana, Plasmodium falciparum, Eimeria tenella, Toxoplasma gondii, Mycobacterium tuberculosis, Streptococcus pneumoniae, Escherichia coli, Staphylococcus aureus, Bacillus anthracis, Birkholderia mallei, Pseudomonas aeruginosa, Helicobacter pylori, Yersinia pestis* and many others.

In a further preferred embodiment the conversion of 3-methylcrotonyl-CoA into 3-methylbutyryl-CoA is achieved by making use of a trans-2-enoyl-CoA reductase (NAD⁺) (EC 1.3.1.44). Trans-2-enoyl-CoA reductases (NAD⁺) are enzymes which catalyze the following reaction:

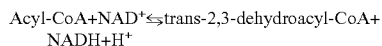

Acyl-CoA+NAD⁺⇌trans-2,3-dehydroacyl-CoA+ NADH+H⁺

This enzyme occurs in a variety of organisms, including eukaryotic and prokaryotic organisms, such as plants, animals and bacteria. The enzyme has, e.g., been described in *Rattus norvegicus, Euglena gracilis, Mycobacterium smegmatis, Pseudomonas fluorescens, Clostridium acetobutylicum, Butyrivibrio fibrisolvens, Pseudomonas aeruginosa, Mycobacterium tuberculosis* and *Treponema denticola*.

In another preferred embodiment the enzyme is an enzyme which is classified as EC 1.3.8 and which uses a flavin prosthetic group as acceptor. The conversion using such an enzyme is schematically shown in FIG. 3. In a preferred embodiment the enzyme is an isovaleryl-CoA dehydrogenase (EC 1.3.8.4). Isovaleryl-CoA dehydrogenases are enzymes which catalyze the following reaction:

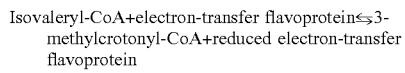

Isovaleryl-CoA+electron-transfer flavoprotein⇌3-methylcrotonyl-CoA+reduced electron-transfer flavoprotein This enzyme occurs in a variety of organisms, including eukaryotic and prokaryotic organisms, such as plants, animals, fungi and bacteria. The enzyme has, e.g., been described in *Homo sapiens, Bos taurus, Rattus norvegicus, Mus musculus, Cavia porcellus, Bombyx mori, Caenorhabditis elegans, Solanum tuberosum, Arabidopsis thaliana, Pisum sativum, Aspergillus oryzae, Pseudomonas aeruginosa* and *Halobacterium salinarum*.

In another embodiment the conversion of 3-methylcrotonyl-CoA into 3-methylbutyryl-CoA may, for example, be achieved by making use of the enzyme from *Myxococcus* sp. which is encoded by the liuA gene (Li et al., Angew. Chem. Int. Ed. 52 (2013), 1304-1308). This enzyme (AibC, LiuA) was annotated as an oxidoreductase and as belonging to the zinc-binding dehydrogenase family. The enzyme was shown to reduce 3-methylcrotonyl-CoA into 3-methylbutyryl-CoA using NADH as co-factor. The amino acid sequence of said protein is available under Uniprot Accession Number Q1 D412.

In a preferred embodiment such an enzyme has an amino acid sequence as shown in SEQ ID NO:5 or shows an amino acid sequence which is at least x % homologous to SEQ ID NO:5 and has the activity of an oxidoreductase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-CoA into 3-methylbutyryl-CoA as set forth herein above.

As regards the determination of sequence identity, the same applies as has been set forth above.

The Enzymatic Conversion of 3-Methylglutaconyl-CoA into 3-Methylcrotonyl-CoA (Step 4 in FIG. 2)

The 3-methylcrotonyl-CoA which is converted according to the present invention into 3-methylbutyryl-CoA according to any of the above described methods (and further converted to isoamyl alcohol according to any of the above described methods which is further converted into isoamyl acetate according to any of the above described methods) may itself be provided by an enzymatic reaction, namely the enzymatic conversion of 3-methylglutaconyl-CoA via decarboxylation into said 3-methylcrotonyl-CoA. The conversion of 3-methylglutaconyl-CoA into 3-methylcrotonyl-CoA is schematically illustrated in FIG. 9.

Thus, the present invention also relates to a method for producing isoamyl alcohol (or isoamyl acetate) from 3-methylglutaconyl-CoA in which 3-methylcrotonyl-CoA is first provided by the enzymatic conversion 3-methylglutaconyl-CoA into 3-methylcrotonyl-CoA which is then further converted into 3-methylbutyryl-CoA. Further, 3-methylbutyryl-CoA is then further converted into isoamyl alcohol (or further to isoamyl acetate) as described herein above.

According to the present invention, the enzymatic conversion of 3-methylglutaconyl-CoA into said 3-methylcrotonyl-CoA can be catalyzed by different enzymes. In one preferred embodiment, the enzymatic conversion of 3-methylglutaconyl-CoA into said 3-methylcrotonyl-CoA makes use of a 3-methylcrotonyl-CoA carboxylase (EC 6.4.1.4). Methylcrotonyl-CoA carboxylases have been described to catalyze the following reaction:

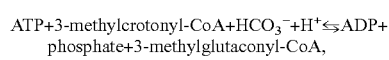

ATP+3-methylcrotonyl-CoA+HCO₃⁻+H⁺⇌ADP+ phosphate+3-methylglutaconyl-CoA, i.e., the carboxylation, but they can be used to catalyze the reaction of decarboxylation. Methylcrotonyl-CoA carboxylases occur in a variety of organisms, including eukaryotic and prokaryotic organisms, such as plants, animals, fungi and bacteria. The enzyme has, e.g., been described in *Daucus carota, Glycine max, Hordeum vulgare, Pisum sativum, Solanum lycopersicum, Solanum tuberosum, Zea mays, Arabidopsis* sp., *Lens culinaris, Homo sapiens, Bos taurus, Rattus norvegicus, Mus musculus, Pagrus major, Emericella nidulans, Pseudomonas aeruginosa, Pseudomonas citronellolis, Acidaminococcus fermentans, Escherichia coli, Mycobacterium* sp. and *Achromobacter* sp.

In another preferred embodiment the conversion of 3-methylglutaconyl-CoA via decarboxylation into 3-methylcrotonyl-CoA is catalyzed by a geranoyl-CoA carboxylase (EC 6.4.1.5). Geranoyl-CoA carboxylases naturally catalyze the following reaction:

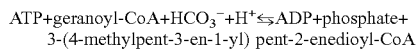
3-(4-methylpent-3-en-1-yl) pent-2-enedioyl-CoA

The enzymes occurs in eukaryotes and prokaryotes, such as plants and bacteria. The enzyme has, e.g., been described in *Daucus carota, Glycine max, Zea mays, Pseudomonas* sp., *Pseudomonas aeruginosa, Pseudomonas citronellolis* and *Pseudomonas mendocina*.

In another preferred embodiment the conversion of 3-methylglutaconyl-CoA via decarboxylation into 3-methylcrotonyl-CoA is catalyzed by a 3-methylglutaconyl-CoA decarboxylase, e.g. a 3-methylglutaconyl-CoA decarboxylase of *Myxococcus xanthus* encoded by the liuB gene (UniProt Accession numbers Q1D4I4 and Q1 D4I3). This gene codes for an enzyme having the two subunits AibA and AibB (Li et al., Angew. Chem. Int. Ed. 52 (2013), 1304-1308).

In another preferred embodiment, the conversion of 3-methylglutaconyl-CoA via decarboxylation into 3-methylcrotonyl-CoA is catalyzed by a glutaconyl-CoA decarboxylase (EC 4.1.1.70). This enzyme naturally catalyzes the decarboxylation of glutaconyl-CoA into 2-butenoyl-CoA also referred to as crotonyl-CoA.

Thus, glutaconyl-CoA decarboxylases (EC 4.1.1.70) naturally catalyze the following reaction:

carboxybut-2-enoyl-CoA⇌but-2-enoyl-CoA+CO$_2$

This enzyme occurs in a variety of organisms, in particular in bacteria, and has, e.g., been described in *Acidaminococcus fermentas* (UniProt Accession number Q06700), *Clostridium symbiosum* (UniProt Accession number B7TVP1), *Clostridium tetanomorphum, Fusobacterium nucleatum, Peptoniphilus asaccharolyticus, Pseudomonas* sp. and *Syntrophus gentianae*.

The Enzymatic Conversion of 3-Hydroxy-3-Methylglutaryl-CoA into 3-Methylglutaconyl-CoA (Step 3 in FIG. 2)

The 3-methylglutaconyl-CoA which is converted according to the present invention into 3-methylcrotonyl-CoA according to any of the above described methods (and which is further converted according to the present invention into 3-methylbutyryl-CoA according to any of the above described methods and further converted to isoamyl alcohol according to any of the above described methods which is further converted into isoamyl acetate according to any of the above described methods) may itself be provided by an enzymatic reaction, namely the enzymatic conversion of 3-hydroxy-3-methylglutaryl-CoA into said 3-methylglutaconyl-CoA by dehydration. The conversion of 3-hydroxy-3-methylglutaryl-CoA into said 3-methylglutaconyl-CoA is schematically illustrated in FIG. 10.

Thus, the present invention also relates to a method for producing isoamyl alcohol (or isoamyl acetate) from 3-hydroxy-3-methylglutaryl-CoA in which 3-methylglutaconyl-CoA is first provided by the enzymatic conversion of 3-hydroxy-3-methylglutaryl-CoA into 3-methylglutaconyl-CoA which is then further converted into 3-methylcrotonyl-CoA. Further, the 3-methylcrotonyl-CoA is then further converted into 3-methylbutyryl-CoA. Further, 3-methylbutyryl-CoA is then further converted into isoamyl alcohol (or further to isoamyl acetate) as described herein above.

According to the present invention, the conversion of 3-hydroxy-3-methylglutaryl-CoA into 3-methylglutaconyl-CoA preferably makes use of an enzyme catalyzing 3-hydroxy-3-methylglutaryl-CoA dehydration. The term "dehydration" is generally referred to as a reaction involving the removal of H$_2$O. Enzymes catalyzing 3-hydroxy-3-methylglutaryl-CoA dehydration are enzymes which catalyze the reaction as shown in FIG. 10.

This reaction is naturally catalyzed by the enzyme 3-methylglutaconyl-coenzyme A hydratase (EC 4.2.1.18) and is shown in FIG. 10.

Thus, in one preferred embodiment, the enzymatic conversion of 3-hydroxy-3-methylglutaryl-CoA into 3-methylglutaconyl-CoA makes use of a 3-methylglutaconyl-coenzyme A hydratase (EC 4.2.1.18).

3-methylglutaconyl-coenzyme A hydratases are enzymes which catalyze the following reaction:

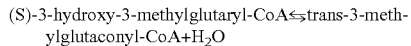

This enzyme occurs in a variety of organisms, including eukaryotic and prokaryotic organisms, such as plants, animals and bacteria. The enzyme has, e.g., been described in *Catharantus roseus, Homo sapiens, Bos taurus, Ovis aries, Acinetobacter* sp., *Myxococcus* sp. and *Pseudomonas putida*. In a preferred embodiment the conversion of 3-hydroxy-3-methylglutaryl-CoA into 3-methylglutaconyl-CoA makes use of a 3-methylglutaconyl-coenzyme A hydratase from *Myxococcus* sp. (UniProt Accession number U2TLJ6). In a preferred embodiment the 3-methylglutaconyl-coenzyme A hydratase is an enzyme from *Myxococcus* sp., and even more preferably an enzyme which has an amino acid sequence as shown in SEQ ID NO:6 or shows an amino acid sequence which is at least x % homologous to SEQ ID NO:6 and has the activity of a 3-methylglutaconyl-coenzyme A hydratase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxy-3-methylglutaryl-CoA into 3-methylglutaconyl-CoA as set forth herein above. As regards the determination of the degree of identity, the same applies as has been set forth herein above.

The conversion of 3-hydroxy-3-methylglutaryl-CoA into 3-methylglutaconyl-CoA can also be achieved by making use of a 3-hydroxy-3-methylglutaryl-coenzyme A dehydratase activity which has been identified, e.g., in *Myxococcus xanthus* and which is encoded by the liuC gene (UniProt Accession number Q1D5Y4) (Li et al., Angew. Chem. Int. Ed. 52 (2013), 1304-1308).

The conversion of 3-hydroxy-3-methylglutaryl-CoA into 3-methylglutaconyl-CoA can not only be achieved by making use of the above 3-hydroxyl-3-methylglutaryl-coenzyme A dehydratase activity which has been identified in *Myxococcus xanthus* and which belongs to enzymes classified as 3-hydroxybutyryl-CoA dehydratases (EC 4.2.1.55). Rather, according to the present invention, the conversion of 3-hydroxy-3-methylglutaryl-CoA into 3-methylglutaconyl-CoA preferably makes use of a 3-hydroxybutyryl-CoA dehydratase (EC 4.2.1.55).

3-hydroxybutyryl-CoA dehydratases (EC 4.2.1.55) are enzymes which naturally catalyze the following reaction:

(3R)-3-hydroxybutanoyl-CoA⇌crotonoyl-CoA+H$_2$O

This enzyme occurs in a variety of organisms, including eukaryotic and prokaryotic organisms and has, e.g., been described in *Rattus norvegicus* and *Rhodospirillum rubrum*.

In a preferred embodiment the conversion of 3-hydroxy-3-methylglutaryl-CoA into 3-methylglutaconyl-CoA makes use of a 3-hydroxybutyryl-CoA dehydratase from a bacterium belonging to a genus selected from the group consisting of *Myxococcus, Corallococcus* and *Stigmatella*. In a more preferred embodiment the 3-hydroxybutyryl-CoA dehydratase is an enzyme from *Myxococcus fulvus* (Uniprot Accession Number F8CDH2), *Myxococcus stipitatus* (Uniprot Accession number L7U993), *Corallococcus coralloides* (Uniprot Accession number H8N0F4) or *Stigmatella aurantiaca* (Uniprot Accession number Q08YS1).

The Enzymatic Condensation of Acetoacetyl-CoA and Acetyl-CoA into 3-Hydroxy-3-Methylglutaryl-CoA (Step 2 in FIG. 2)

Figure 11:
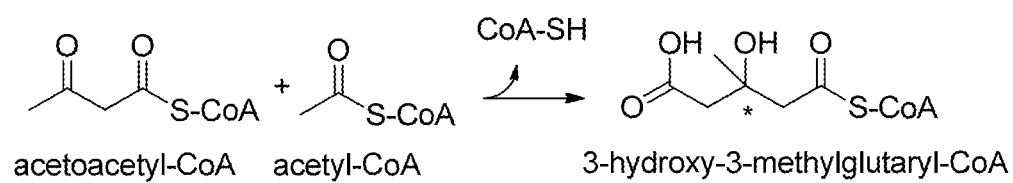

The 3-hydroxy-3-methylglutaryl-CoA which is converted according to the present invention into 3-methylglutaconyl-CoA according to any of the above described methods (and which is further converted according to the present invention into 3-methylcrotonyl-CoA according to any of the above described methods and which is further converted according to the present invention into 3-methylbutyryl-CoA according to any of the above described methods and further converted to isoamyl alcohol according to any of the above described methods which is further converted into isoamyl acetate according to any of the above described methods) may itself be provided by an enzymatic reaction, namely the enzymatic condensation of acetoacetyl-CoA and acetyl-CoA into said 3-hydroxy-3-methylglutaryl-CoA. The condensation of acetoacetyl-CoA and acetyl-CoA into said 3-hydroxy-3-methylglutaryl-CoA is schematically illustrated in FIG. 11.

Thus, the present invention also relates to a method for producing isoamyl alcohol (or isoamyl acetate) from acetoacetyl-CoA in which 3-hydroxy-3-methylglutaryl-CoA is first provided by the enzymatic condensation of acetoacetyl-CoA and acetyl-CoA into 3-hydroxy-3-methylglutaryl-CoA which is then further converted into 3-methylglutaconyl-CoA which is then further converted into 3-methylcrotonyl-CoA. Further, the 3-methylcrotonyl-CoA is then further converted into 3-methylbutyryl-CoA. Further, 3-methylbutyryl-CoA is then further converted into isoamyl alcohol (or further to isoamyl acetate) as described herein above.

Thus, according to the present invention, the 3-hydroxy-3-methylglutaryl-CoA which is converted into 3-methylglutaconyl-CoA can itself be provided enzymatically, e.g., by the condensation of acetyl-CoA and acetoacetyl-CoA, a reaction which is naturally catalyzed by the enzyme 3-hydroxy-3-methylglutaryl-CoA synthase (also referred to as HMG-CoA synthase). HMG-CoA synthases are classified in EC 2.3.3.10 (formerly, HMG-CoA synthase has been classified as EC 4.1.3.5 but has been transferred to EC 2.3.3.10). The term "HMG-CoA synthase" refers to any enzyme which is able to catalyze the reaction where acetyl-CoA condenses with acetoacetyl-CoA to form 3-hydroxy-3-methylglutaryl-CoA (HMG-CoA) (see FIG. 11). HMG-CoA synthase is part of the mevalonate pathway. Two pathways have been identified for the synthesis of isopentenyl pyrophosphate (IPP), i.e. the mevalonate pathway and the glyceraldehyde 3-phosphate-pyruvate pathway. HMG-CoA synthase catalyzes the biological Claisen condensation of acetyl-CoA with acetoacetyl-CoA and is a member of a superfamily of acyl-condensing enzymes that includes beta-ketothiolases, fatty acid synthases (beta-ketoacyl carrier protein synthase) and polyketide synthases. HMG-CoA synthase has been described for various organisms. Also amino acid and nucleic acid sequences encoding HMG-CoA synthases from numerous sources are available. Generally, the sequences only share a low degree of overall sequence identity. For example, the enzymes from *Staphylococcus* or *Streptococcus* show only about 20% identity to those of human and avian HMG-CoA synthase. In some sources it is reported that the bacterial HMG-CoA synthases and their animal counterparts exhibit only about 10% overall sequence identity (Sutherlin et al., J. Bacteriol. 184 (2002), 4065-4070). However, the amino acid residues involved in the acetylation and condensation reactions are conserved among bacterial and eukaryotic HMG-CoA synthases (Campobasso et al., J. Biol. Chem. 279 (2004), 44883-44888). The three-dimensional structure of three HMG-CoA synthase enzymes has been determined and the amino acids crucial for the enzymatic reaction are in principle well characterized (Campobasso et al., loc. cit.; Chun et al., J. Biol. Chem. 275 (2000), 17946-17953; Nagegowda et al., Biochem. J. 383 (2004), 517-527; Hegardt, Biochem. J. 338 (1999), 569-582). In eukaryotes there exist two forms of the HMG-CoA synthase, i.e. a cytosolic and a mitochondrial form. The cytosolic form plays a key role in the production of cholesterol and other isoprenoids and the mitochondrial form is involved in the production of ketone bodies.

In principle any HMG-CoA synthase enzyme can be used in the context of the present invention, in particular from prokaryotic or eukaryotic organisms.

Prokaryotic HMG-CoA synthases are described, e.g., from *Staphylococcus aureus* (Campobasso et al., loc. cit.; Uniprot accession number Q9FD87), *Staphylococcus epidermidis* (Uniprot accession number Q9FD76), *Staphylococcus haemolyticus* (Uniprot accession number Q9FD82), *Enterococcus faecalis* (Sutherlin et al., loc. cit.; Uniprot accession number Q9FD7), *Enterococcus faecium* (Uniprot accession number Q9FD66), *Streptococcus pneumonia* (Uniprot accession number Q9FD56), *Streptococcus pyogenes* (Uniprot accession number Q9FD61) and *Methanobacterium thermoautotrophicum* (accession number AE000857), *Borrelia burgdorferi* (NCBI accession number BB0683). Further HMG-CoA synthases are, e.g., described in WO 2011/032934.

In a preferred embodiment the condensation of acetyl-CoA and acetoacetyl-CoA into 3-hydroxy-3-methylglutaryl-CoA makes use of an HMG-CoA synthase from a bacterium of a genus selected from the group consisting of *Enterococcus, Schizosaccharomyces, Saccharomyces, Lactobacillus* or *Myxococcus*. In a more preferred embodiment the HMG-CoA synthase is from *Enterococcus faecalis*, even more preferably from *Enterococcus faecalis* (strain ATCC 700802/V583) (Uniprot Accession number Q835L4), *Schizosaccharomyces pombe*, even more preferably from *Schizosaccharomyces pombe* (strain 972/ATCC 24843) (Uniprot Accession number P54874), *Saccharomyces cerevisae*, even more preferably from *Saccharomyces cerevisiae* (strain ATCC 204508/S288c) (Uniprot Accession number P54839), *Lactobacillus delbrueckii*, even more preferably from *Lactobacillus delbrueckii* subsp. *bulgaricus* (strain ATCC 11842) (Uniprot Accession number Q1GAH5) or *Myxococcus xanthus* (UniProt Accession number Q1 D411).

A preferred HMG-CoA synthase is the enzyme from *Schizosaccharomyces pombe* (Uniprot P54874). The sequence of the HMG-CoA synthase from *Schizosaccharomyces pombe* (Uniprot P54874) is shown in SEQ ID NO: 7. In a particularly preferred embodiment, the HMG-CoA synthase employed in the method of the invention has an amino acid sequence as shown in SEQ ID NO: 7 or shows an amino acid sequence which is at least x % homologous to SEQ ID NO: 7 and has the activity of a HMG-CoA synthase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of catalyzing the condensation of acetyl-CoA and acetoacetyl-CoA into 3-hydroxy-3-methylglutaryl-CoA. As regards the determination of the degree of identity, the same applies as has been set forth herein above.

Another preferred HMG-CoA synthase is the enzyme from *Myxococcus xanthus* (UniProt Accession number Q1 D411). The sequence of the HMG-CoA synthase from *Myxococcus xanthus* (UniProt Accession number Q1 D411) is shown in SEQ ID NO: 12. In a particularly preferred embodiment, the HMG-CoA synthase employed in the method of the invention has an amino acid sequence as shown in SEQ ID NO: 12 or shows an amino acid sequence which is at least x % homologous to SEQ ID NO: 12 and has the activity of a HMG-CoA synthase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of catalyzing the condensation of acetyl-CoA and acetoacetyl-CoA into 3-hydroxy-3-methylglutaryl-CoA. As regards the determination of the degree of identity, the same applies as has been set forth herein above.

The Enzymatic Biosynthesis of Acetoacetyl-CoA from Acetyl-CoA (Step 1 in FIG. 2)

The acetoacetyl-CoA which is condensed with acetyl-CoA according to the present invention into 3-hydroxy-3-methylglutaryl-CoA according of any of the above described methods (and which is converted according to the present invention into 3-methylglutaconyl-CoA according to any of the above described methods and which is further converted according to the present invention into 3-methylcrotonyl-CoA according to any of the above described methods and which is further converted according to the present invention into 3-methylbutyryl-CoA according to any of the above described methods and further converted to isoamyl alcohol according to any of the above described methods which is further converted into isoamyl acetate according to any of the above described methods) may itself be provided by enzymatic reactions.

In one alternative, according to the present invention, acetoacetyl-CoA can be produced by the enzymatic condensation of two acetyl-CoA molecules into acetoacetyl-CoA.

In another alternative, acetoacetyl-CoA can be produced by the enzymatic condensation of malonyl-CoA and acetyl-CoA into acetoacetyl-CoA.

Thus, the present invention also relates to a method for producing isoamyl alcohol (or isoamyl acetate) from acetyl-CoA in which acetoacetyl-CoA is first provided by (i) the enzymatic condensation of two acetyl-CoA molecules into acetoacetyl-CoA and/or (ii) the enzymatic condensation of acetyl-CoA and malonyl-CoA into acetoacetyl-CoA wherein acetoacetyl-CoA and acetyl-CoA are then further enzymatically condensed into 3-hydroxy-3-methylglutaryl-CoA. 3-hydroxy-3-methylglutaryl-CoA is then further converted into 3-methylglutaconyl-CoA which is then further converted into 3-methylcrotonyl-CoA. Further, the 3-methylcrotonyl-CoA is then further converted into 3-methylbutyryl-CoA. Further, 3-methylbutyryl-CoA is then further converted into isoamyl alcohol (or further to isoamyl acetate) as described herein above.

Thus, in one alternative (i), acetoacetyl-CoA can be produced from acetyl-CoA as, e.g., described in WO 2013/057194. According to the present invention, acetyl-CoA can, for example, be converted into acetoacetyl-CoA by the following reaction:

This reaction is catalyzed by enzymes called acetyl-CoA C-acetyltransferases which are classified as EC 2.3.1.9. These enzymes catalyze the (claisen type) condensation of two acetyl-CoA molecules into acetoacetyl-CoA. Enzymes which belong to this class of enzymes catalyze the above shown conversion of two molecules of acetyl-CoA into acetoacetyl-CoA which is also schematically illustrated in FIG. 12.

Enzymes belonging to this class and catalyzing the above shown conversion of two molecules of acetyl-CoA into acetoacetyl-CoA and CoA occur in organisms of all kingdoms, i.e. plants, animals, fungi, bacteria etc. and have extensively been described in the literature. Nucleotide and/or amino acid sequences for such enzymes have been determined for a variety of organisms, like *Homo sapiens*, *Arabidopsis thaliana*, *E. coli*, *Bacillus subtilis*, *Clostridium acetobutylicum* and *Candida*, to name just some examples. In principle, any acetyl-CoA C-acetyltransferase (EC 2.3.1.9) can be used in the context of the present invention. In one preferred embodiment the enzyme is an acetyl-CoA acetyltransferase from *Clostridium acetobutylicum* (Uniprot P45359). In a particularly preferred embodiment, the acetyl-CoA acetyltransferase employed in the method of the invention has an amino acid sequence as shown in SEQ ID NO:8 or shows an amino acid sequence which is at least x % homologous to SEQ ID NO:8 and has the activity of an acetyl-CoA acetyltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting acetyl-CoA into acetoacetyl-CoA as set forth herein above.

As regards the determination of the degree of identity, the same applies as has been set forth herein above.

In the other alternative (ii), the provision of acetoacetyl-CoA may also be achieved by the enzymatic conversion of acetyl-CoA and malonyl-CoA into acetoacetyl-CoA according to the following reaction.

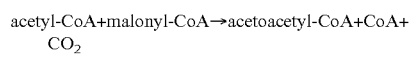

This reaction is catalyzed by an enzyme called acetoacetyl-CoA synthase (EC 2.3.1.194). Enzymes belonging to this class of enzymes catalyze the above shown conversion of one molecule of acetyl-CoA and one molecule of malonyl-CoA into acetoacetyl-CoA and the concomitant release of $CO_2$. This reaction is also schematically illustrated in FIG. 12.

The gene encoding this enzyme was identified in the mevalonate pathway gene cluster for terpenoid production in a soil-isolated Gram-positive *Streptomyces* sp. Strain CL190 (Okamura et al., PNAS USA 107 (2010), 11265-11270, 2010). Moreover a biosynthetic pathway using this enzyme for acetoacetyl-CoA production was recently developed in *E. coli* (Matsumoto K et al., Biosci. Biotechnol. Biochem, 75 (2011), 364-366). Accordingly, in a preferred embodiment, the enzymatic conversion of acetyl-CoA into said acetoacetyl-CoA consists of a single enzymatic reaction in which acetyl-CoA is directly converted into acetoacetyl-CoA. Preferably, the enzymatic conversion of acetyl-CoA into acetoacetyl-CoA is achieved by making use of an acetyl-CoA acetyltransferase (EC 2.3.1.9) as described above.

Alternatively, the acetoacetyl-CoA can also be provided by an enzymatic conversion which comprises two steps, i.e.;
(i) the enzymatic conversion of acetyl-CoA into malonyl-CoA; and
(ii) the enzymatic conversion of malonyl-CoA and acetyl-CoA into acetoacetyl-CoA.

Preferably, the enzymatic conversion of acetyl-CoA into malonyl-CoA is achieved by the use of an acetyl-CoA carboxylase (EC 6.4.1.2). This enzyme catalyzes the following reaction:

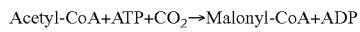

Acetyl-CoA+ATP+CO$_2$→Malonyl-CoA+ADP

Preferably, the enzymatic conversion of malonyl-CoA and acetyl-CoA into acetoacetyl-CoA is achieved by the use of an acetoacetyl-CoA synthase (EC 2.3.1.194). In principle, any acetyl-CoA acetyltransferase (EC 2.3.1.9), acetyl-CoA carboxylase (EC 6.4.1.2) and/or acetoacetyl-CoA synthase (EC 2.3.1.194) can be applied in the method according to the invention.

Figure 12:
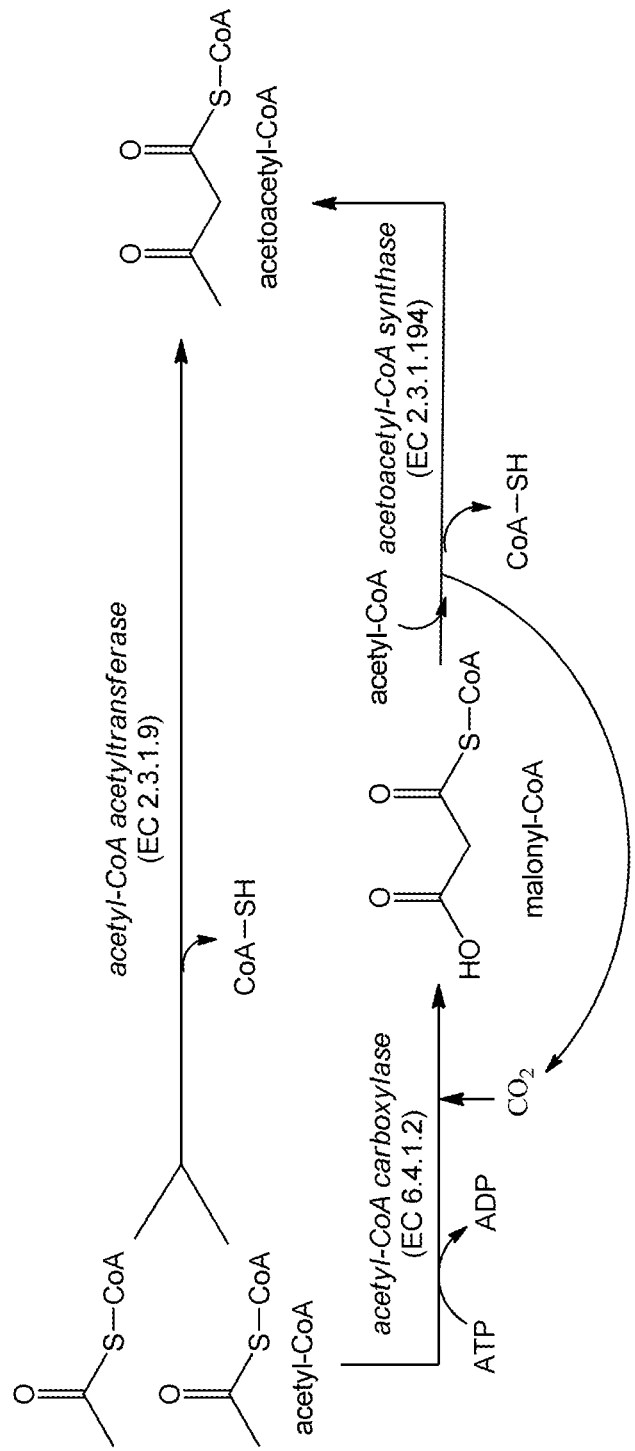

FIG. 12 shows schematically possible ways of producing acetoacetyl-CoA from acetyl-CoA.

The Enzymatic Conversion of 3-Methylbutyryl-CoA into 3-Methylbutyraldehyde (step 6 in FIG. 2)

The present invention also relates to a method for the production of 3-methylbutyraldehyde from 3-methylbutyryl-CoA comprising the enzymatic conversion of 3-methylbutyryl-CoA into 3-methylbutyraldehyde (step 6 as illustrated in FIG. 2). In a preferred method for the production of 3-methylbutyraldehyde, the enzymatic conversion of said 3-methylbutyryl-CoA into said 3-methylbutyraldehyde is achieved by making use of an enzyme which is classified as EC 1.2.1.- and which is an oxidoreductase acting on the CoA thioester group of acyl-CoA as acceptor with NADH or NADPH as donor (EC 1.2.1.-). In a more preferred embodiment, the enzymatic conversion of said 3-methylbutyryl-CoA into said 3-methylbutyraldehyde is achieved by making use of an acetaldehyde dehydrogenase (acetylating) (EC 1.2.1.10) or a propanal dehydrogenase (CoA-propanoylating) (EC 1.2.1.87).

As regards the afore-mentioned embodiment, for the enzyme which is classified as EC 1.2.1.- and which is an oxidoreductase acting on the CoA thioester group of acyl-CoA as acceptor with NADH or NADPH as donor (EC 1.2.1.-), the acetaldehyde dehydrogenase (acetylating) (EC 1.2.1.10) and the propanal dehydrogenase (CoA-propanoylating) (EC 1.2.1.87), the same applies as has been set forth above in connection with the other methods of the present invention.

The Direct Enzymatic Conversion of 3-Methylbutyryl-CoA into Isoamyl Alcohol (Step 8 in FIG. 2)

The present invention also relates to a method for the production of isoamyl alcohol from 3-methylbutyryl-CoA comprising the enzymatic conversion of 3-methyl butyryl-CoA into isoamyl alcohol wherein 3-methylbutyryl-CoA is directly converted into isoamyl alcohol. Thus, the present invention relates to a method for the production isoamyl alcohol (3-methylbutan-1-ol) comprising the enzymatic conversion of 3-methylbutyryl-CoA into isoamyl alcohol comprising: a single enzymatic reaction in which 3-methylbutyryl-CoA is directly converted into isoamyl alcohol by making use of an alcohol-forming short chain acyl-CoA dehydrogenase/fatty acyl-CoA reductase (step 8 as illustrated in FIG. 2) or an alcohol-forming fatty acyl-CoA reductase (long-chain acyl-CoA:NADPH reductase) (EC 1.2.1.84).

As regards the afore-mentioned embodiment, for the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84), the same applies as has been set forth above in connection with the other methods of the present invention.

A method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

In another embodiment the method according to the invention is carried out in culture, in the presence of an organism, preferably a microorganism, producing the enzymes described above for the conversions of the methods according to the present invention as described herein above. A method which employs a microorganism for carrying out a method according to the invention is referred to as an "in vivo" method. It is possible to use a microorganism which naturally produces the enzymes described above for the conversions of the methods according to the present invention or a microorganism which had been genetically modified so that it expresses (including overexpresses) one or more of such enzymes. Thus, the microorganism can be an engineered microorganism which expresses enzymes described above for the conversions of the methods according to the present invention, i.e. which has in its genome a nucleotide sequence encoding such enzymes and which has been modified to overexpress them. The expression may occur constitutively or in an induced or regulated manner.

In another embodiment the microorganism can be a microorganism which has been genetically modified by the introduction of one or more nucleic acid molecules containing nucleotide sequences encoding one or more enzymes described above for the conversions of the methods according to the present invention. The nucleic acid molecule can be stably integrated into the genome of the microorganism or may be present in an extrachromosomal manner, e.g. on a plasmid.

Such a genetically modified microorganism can, e.g., be a microorganism that does not naturally express enzymes described above for the conversions of the methods according to the present invention and which has been genetically modified to express such enzymes or a microorganism which naturally expresses such enzymes and which has been genetically modified, e.g. transformed with a nucleic acid, e.g. a vector, encoding the respective enzyme(s), and/or insertion of a promoter in front of the endogenous nucleotide sequence encoding the enzyme in order to increase the respective activity in said microorganism.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme. Thus, the enzymes and (micro)organisms employed in connection with the present invention are preferably non-naturally occurring enzymes or (micro)organisms, i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

Thus, it is also possible in the context of the present invention that the microorganism is a microorganism which naturally does not have the respective enzyme activity but which is genetically modified so as to comprise a nucleotide sequence allowing the expression of a corresponding enzyme. Similarly, the microorganism may also be a microorganism which naturally has the respective enzyme activity but which is genetically modified so as to enhance such an activity, e.g. by the introduction of an exogenous nucleotide sequence encoding a corresponding enzyme or by the introduction of a promoter for the endogenous gene encoding the enzyme to increase endogenous production to overexpressed (non-natural) levels.

If a microorganism is used which naturally expresses a corresponding enzyme, it is possible to modify such a microorganism so that the respective activity is overexpressed in the microorganism. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

By using microorganisms which express enzymes described above for the conversions of the methods according to the present invention, it is possible to carry out the methods according to the invention directly in the culture medium, without the need to separate or purify the enzymes.

In one embodiment the organism employed in a method according to the invention is a microorganism which has been genetically modified to contain a foreign nucleic acid molecule encoding at least one enzyme described above for the conversions of the methods according to the present invention. The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In another embodiment, the method according to the invention makes use of a photosynthetic microorganism expressing at least one enzyme for the conversion according to the invention as described above. Preferably, the microorganism is a photosynthetic bacterium, or a microalgae. In a further embodiment the microorganism is an algae, more preferably an algae belonging to the diatomeae.

It is also conceivable to use in the method according to the invention a combination of microorganisms wherein different microorganisms express different enzymes as described above. The genetic modification of microorganisms to express an enzyme of interest will also be further described in detail below.

In a preferred embodiment, the method of the present invention makes use of an organism, preferably a microorganism, which is genetically modified in order to avoid the leakage of acetyl-CoA, thereby increasing the intracellular concentration of acetyl-CoA. Genetic modifications leading to an increase in the intracellular concentration of acetyl-CoA are known in the art. Without being bound to theory, such an organism, preferably a microorganism, may preferably be genetically modified by deleting or inactivating the following genes:
$\Delta$ackA (acetate kinase), $\Delta$ldh (lactate dehydrogenase), $\Delta$adhE (alcohol dehydrogenase), $\Delta$frdB and/or $\Delta$frdC (fumarate reductase and fumarate dehydrogenase).

Alternatively, or in addition to any of the above deletions, the organism or microorganism may genetically be modified by overexpressing the gene panK/coaA encoding Pantothenate kinase, thereby increasing the CoA/acetyl-CoA intracellular pool.

These modifications which avoid the leakage of acetyl-CoA are known in the art and corresponding modified organisms have been used in methods for the bioconversion of exogenous isoamyl alcohol into isoamyl acetate by an *E. coli* strain expressing ATF2 (Metab. Eng. 6 (2004), 294-309).

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above.

Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harbouring the above described enzyme(s). In a bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

In a preferred embodiment the method according to the present invention also comprises the step of recovering the isoamyl alcohol (or the isoamyl acetate) produced by the method. For example, if the method according to the present invention is carried out in vivo by fermenting a corresponding microorganism expressing the necessary enzymes, the isoamyl alcohol (or the isoamyl acetate) can be recovered by solvent liquid/liquid extraction. Alternatively, the isoamyl alcohol (or the isoamyl acetate) can be recovered by a stripping process as it has been described for the butanol or isobutanol extraction from bioreactors. Such recovery methods are known to the skilled person and are, e.g., described in Appl. Microbiol. Biotechnol. 90 (2011), 1681-1690 which exemplarily describes a fermentation process for the production of isobutanol by *E. coli* and its recovery by a gas stripping process.

In a preferred embodiment, the present invention relates to a method as described herein above in which a microorganism as described herein above is employed, wherein the microorganism is capable of enzymatically converting acetyl-CoA into isoamyl alcohol (and preferably further into isoamyl acetate), wherein said method comprises culturing the microorganism in a culture medium.

The enzymes used in the method according to the invention can be naturally occurring enzymes or enzymes which are derived from a naturally occurring enzymes, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding a corresponding enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a corresponding enzyme. Thus, in a preferred embodiment, the microorganism is a recombinant microorganism which has been genetically modified to have an increased activity of at least one enzyme described above for the conversions of the method according to the present invention. This can be achieved e.g. by transforming the microorganism with a nucleic acid encoding a corresponding enzyme. A detailed description of genetic modification of microorganisms will be given further below. Preferably, the nucleic acid molecule introduced into the microorganism is a nucleic acid molecule which is heterologous with respect to the microorganism, i.e. it does not naturally occur in said microorganism.

In the context of the present invention, an "increased activity" means that the expression and/or the activity of an enzyme in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3

(1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to a (recombinant) organism or microorganism which is able to express one or more, preferably at least two of the above described enzymes required for the enzymatic conversion of acetyl-CoA into isoamyl alcohol (or isoamyl acetate).

Thus, the present invention relates to a recombinant organism or microorganism which expresses
(i) an enzyme capable of enzymatically converting 3-methylbutyryl-CoA into 3-methylbutyraldehyde as defined above (step 6 as shown in FIG. 2);
(ii) an enzyme capable of enzymatically converting 3-methylbutyraldehyde into isoamyl alcohol as defined above (step 7 as shown in FIG. 2);
(iii) an enzyme capable of enzymatically converting 3-methylglutaconyl-CoA into 3-methylcrotonyl-CoA (step 4 as shown in FIG. 2); and
(iv) an enzyme capable of enzymatically converting 3-methylcrotonyl-CoA into 3-methylbutyryl-CoA (step 5 as shown in FIG. 2).

In a preferred embodiment, the recombinant organism or microorganism which expresses (i) an enzyme capable of enzymatically converting 3-methylbutyryl-CoA into 3-methylbutyraldehyde as defined above (step 6 as shown in FIG. 2); (ii) an enzyme capable of enzymatically converting 3-methylbutyraldehyde into isoamyl alcohol as defined above (step 7 as shown in FIG. 2); (iii) an enzyme capable of enzymatically converting 3-methylglutaconyl-CoA into 3-methylcrotonyl-CoA (step 4 as shown in FIG. 2); and (iv) an enzyme capable of enzymatically converting 3-methylcrotonyl-CoA into 3-methylbutyryl-CoA (step 5 as shown in FIG. 2) is a recombinant organism or microorganism, wherein the enzyme capable of enzymatically converting said 3-methyl butyryl-CoA into said 3-methylbutyraldehyde (step 6 as shown in FIG. 2) is an enzyme which is classified as EC 1.2.1.- and which is an oxidoreductase acting on the CoA thioester group of acyl-CoA as acceptor with NADH or NADPH as donor as defined herein above.

In a preferred embodiment, this recombinant organism or microorganism is a recombinant organism or microorganism, wherein the enzyme capable of enzymatically converting said 3-methyl butyryl-CoA into said 3-methylbutyraldehyde (step 6 as shown in FIG. 2) is an acetaldehyde dehydrogenase (acetylating) (EC 1.2.1.10) or a propanal dehydrogenase (CoA-propanoylating) (EC 1.2.1.87) as defined above.

In a preferred embodiment, the recombinant organism or microorganism which expresses (i) an enzyme capable of enzymatically converting 3-methylbutyryl-CoA into 3-methylbutyraldehyde as defined above (step 6 as shown in FIG. 2); (ii) an enzyme capable of enzymatically converting 3-methylbutyraldehyde into isoamyl alcohol as defined above (step 7 as shown in FIG. 2); (iii) an enzyme capable of enzymatically converting 3-methylglutaconyl-CoA into 3-methylcrotonyl-CoA (step 4 as shown in FIG. 2); and (iv) an enzyme capable of enzymatically converting 3-methylcrotonyl-CoA into 3-methylbutyryl-CoA (step 5 as shown in FIG. 2) is a recombinant organism or microorganism, wherein the enzyme capable of enzymatically converting said 3-methylbutyraldehyde into said isoamyl alcohol (step 7 as shown in FIG. 2) is an enzyme which is classified as EC 1.1.1.- and which is an oxidoreductase acting on the aldehyde group as acceptor with NADH and NADPH as donor as defined above.

In a preferred embodiment, this recombinant organism or microorganism is a recombinant organism or microorganism, wherein the enzyme capable of enzymatically converting said 3-methylbutyraldehyde into said isoamyl alcohol (step 7 as shown in FIG. 2) is a 3-methylbutanal reductase (EC 1.1.1.265), an alcohol dehydrogenase (EC 1.1.1.1) or an NADP dependent alcohol dehydrogenase (EC 1.1.1.2) as defined above.

In a preferred embodiment, the recombinant organism or microorganism which expresses (i) an enzyme capable of enzymatically converting 3-methylbutyryl-CoA into 3-methylbutyraldehyde as defined above (step 6 as shown in FIG. 2); (ii) an enzyme capable of enzymatically converting 3-methylbutyraldehyde into isoamyl alcohol as defined above (step 7 as shown in FIG. 2); (iii) an enzyme capable of enzymatically converting 3-methylglutaconyl-CoA into 3-methylcrotonyl-CoA (step 4 as shown in FIG. 2); and (iv)

an enzyme capable of enzymatically converting 3-methylcrotonyl-CoA into 3-methylbutyryl-CoA (step 5 as shown in FIG. 2) is a recombinant organism or microorganism, wherein the enzyme capable of enzymatically converting 3-methylglutaconyl-CoA into 3-methylcrotonyl-CoA (step 4 as shown in FIG. 2) is an enzyme which is a 3-methylcrotonyl-CoA carboxylase (EC 6.4.1.4), geranoyl-CoA carboxylase (EC 6.4.1.5) or a glutaconyl-CoA decarboxylase (EC 4.1.1.70).

In a preferred embodiment, the recombinant organism or microorganism which expresses (i) an enzyme capable of enzymatically converting 3-methylbutyryl-CoA into 3-methylbutyraldehyde as defined above (step 6 as shown in FIG. 2); (ii) an enzyme capable of enzymatically converting 3-methylbutyraldehyde into isoamyl alcohol as defined above (step 7 as shown in FIG. 2); (iii) an enzyme capable of enzymatically converting 3-methylglutaconyl-CoA into 3-methylcrotonyl-CoA (step 4 as shown in FIG. 2); and (iv) an enzyme capable of enzymatically converting 3-methylcrotonyl-CoA into 3-methylbutyryl-CoA (step 5 as shown in FIG. 2) is a recombinant organism or microorganism, wherein the enzyme capable of enzymatically converting 3-methylcrotonyl-CoA into 3-methylbutyryl-CoA according to (iv) is an enzyme which is classified as EC 1.3.-.- and which is an oxidoreductase acting on a CH—CH group as described herein above.

In a preferred embodiment, the recombinant organism or microorganism is an organism or microorganism, wherein the enzyme classified as EC 1.3.-.- is selected from the group consisting of
(i) an acyl-CoA dehydrogenase (NADP+) (EC 1.3.1.8);
(ii) an enoyl-[acyl-carrier-protein] reductase (NADPH, Si-specific) (EC 1.3.1.10);
(iii) a cis-2-enoyl-CoA reductase (NADPH) (EC 1.3.1.37);
(iv) a trans-2-enoyl-CoA reductase (NADPH) (EC 1.3.1.38);
(v) an enoyl-[acyl-carrier-protein] reductase (NADPH, Re-specific) (EC 1.3.1.39);
(vi) crotonyl-CoA reductase (EC 1.3.1.86);
(vii) an enoyl-[acyl-carrier-protein] reductase (NADH) (EC 1.3.1.9);
(viii) a trans-2-enoyl-CoA reductase (NAD$^+$) (EC 1.3.1.44); and
(ix) an isovaleryl-CoA dehydrogenase (EC 1.3.8.4) as described herein above.

In a further aspect, the above recombinant organism or microorganism is an organism or microorganism which further expresses an enzyme capable of enzymatically converting isoamyl alcohol into 3-methylbutyl acetate (isoamyl acetate) as defined above (step 9 as shown in FIG. 2).

In a preferred embodiment, the above recombinant organism or microorganism which further expresses an enzyme capable of enzymatically converting isoamyl alcohol into 3-methylbutyl acetate (isoamyl acetate) as defined above (step 9 as shown in FIG. 2) is a recombinant organism or microorganism, wherein the enzyme capable of enzymatically converting isoamyl alcohol into 3-methylbutyl acetate (isoamyl acetate) is an alcohol-O-acetyl-transferase (EC 2.3.1.84) as described herein above. In a further aspect, the present invention relates to a recombinant organism or microorganism which expresses
(i) an alcohol-forming short chain acyl-CoA dehydrogenase/fatty acyl-CoA reductase as described herein above (step 8 as shown in FIG. 2), preferably an alcohol-forming fatty acyl-CoA reductase (long-chain acyl-CoA:NADPH reductase) (EC 1.2.1.84) as described herein above;

(ii) an enzyme capable of enzymatically converting 3-methylcrotonyl-CoA into 3-methylbutyryl-CoA as described herein above (step 5 as shown in FIG. 2); and
(iii) an enzyme capable of enzymatically converting 3-methylglutaconyl-CoA into 3-methylcrotonyl-CoA (step 4 as shown in FIG. 2).

In a preferred embodiment, the recombinant organism or microorganism which expresses (i) an alcohol-forming short chain acyl-CoA dehydrogenase/fatty acyl-CoA reductase as described herein above (step 8 as shown in FIG. 2) or an alcohol-forming fatty acyl-CoA reductase (long-chain acyl-CoA:NADPH reductase) (EC 1.2.1.84) as described herein above; and (ii) an enzyme capable of enzymatically converting 3-methylcrotonyl-CoA into 3-methylbutyryl-CoA as described herein above (step 5 as shown in FIG. 2); and (iii) an enzyme capable of enzymatically converting 3-methylglutaconyl-CoA into 3-methylcrotonyl-CoA step 4 as shown in FIG. 2)
is a recombinant organism or microorganism, wherein the enzyme capable of enzymatically converting 3-methylcrotonyl-CoA into 3-methylbutyryl-CoA according to (ii) is an enzyme which is classified as EC 1.3.-.- and which is an oxidoreductase acting on a CH—CH group as described herein above.

In a further preferred embodiment, the recombinant organism or microorganism is a recombinant organism or microorganism, wherein the enzyme classified as EC 1.3.-.- is selected from the group consisting of
(i) an acyl-CoA dehydrogenase (NADP+) (EC 1.3.1.8);
(ii) an enoyl-[acyl-carrier-protein] reductase (NADPH, Si-specific) (EC 1.3.1.10);
(iii) a cis-2-enoyl-CoA reductase (NADPH) (EC 1.3.1.37);
(iv) a trans-2-enoyl-CoA reductase (NADPH) (EC 1.3.1.38);
(v) an enoyl-[acyl-carrier-protein] reductase (NADPH, Re-specific) (EC 1.3.1.39);
(vi) crotonyl-CoA reductase (EC 1.3.1.86);
(vii) an enoyl-[acyl-carrier-protein] reductase (NADH) (EC 1.3.1.9);
(viii) a trans-2-enoyl-CoA reductase (NAD$^+$) (EC 1.3.1.44); and
(ix) an isovaleryl-CoA dehydrogenase (EC 1.3.8.4).

In a preferred embodiment, the recombinant organism or microorganism which expresses (i) an alcohol-forming short chain acyl-CoA dehydrogenase/fatty acyl-CoA reductase as described herein above (step 8 as shown in FIG. 2) or an alcohol-forming fatty acyl-CoA reductase (long-chain acyl-CoA:NADPH reductase) (EC 1.2.1.84) as described herein above; and (ii) an enzyme capable of enzymatically converting 3-methylcrotonyl-CoA into 3-methylbutyryl-CoA as described herein above (step 5 as shown in FIG. 2); and (iii) an enzyme capable of enzymatically converting 3-methylglutaconyl-CoA into 3-methylcrotonyl-CoA (step 4 as shown in FIG. 2)
is a recombinant organism or microorganism, wherein the enzyme capable of enzymatically converting 3-methylglutaconyl-CoA into 3-methylcrotonyl-CoA according to (iii) is an enzyme which is a 3-methylcrotonyl-CoA carboxylase (EC 6.4.1.4), geranoyl-CoA carboxylase (EC 6.4.1.5) or a glutaconyl-CoA decarboxylase (EC 4.1.1.70).

In a further aspect, the above recombinant organism or microorganism is an organism or microorganism which further expresses an enzyme capable of enzymatically converting isoamyl alcohol into 3-methylbutyl acetate (isoamyl acetate) as defined above (step 9 as shown in FIG. 2).

In a preferred embodiment, the above recombinant organism or microorganism which further expresses an enzyme capable of enzymatically converting isoamyl alcohol into 3-methylbutyl acetate (isoamyl acetate) as defined above (step 9 as shown in FIG. 2) is a recombinant organism or microorganism, wherein the enzyme capable of enzymatically converting isoamyl alcohol into 3-methylbutyl acetate (isoamyl acetate) is an alcohol-O-acetyl-transferase (EC 2.3.1.84) as described herein above.

The microorganism is preferably a bacterium, a yeast or a fungus. In another preferred embodiment, the organism is a plant or a non-human animal. As regards other preferred embodiments of the bacterium, recombinant organism or microorganism, the same applies as has been set forth above in connection with the methods according to the present invention.

The present invention furthermore relates to the use of an enzyme which is classified as EC 1.2.1.- and which is an oxidoreductase acting on the CoA thioester group of acyl-CoA as acceptor with NADH or NADPH as donor (step 6 as shown in FIG. 2) or an organism or microorganism which expresses such an enzyme for the conversion of 3-methylbutyryl-CoA into 3-methylbutyraldehyde. In a preferred embodiment, said enzyme, is an acetaldehyde dehydrogenase (acetylating) (EC 1.2.1.10) or a propanal dehydrogenase (CoA-propanoylating) (EC 1.2.1.87).

As regards the enzyme which is classified as EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87) and the organism or microorganism the same applies as has been set forth above in connection with the methods and the organisms or microorganisms according to the present invention.

Furthermore, the present invention furthermore relates to the use
(i) of a combination of an enzyme which is classified as an EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and
   an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or
(ii) of an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2)
for the conversion of 3-methylbutyryl-CoA into isoamyl alcohol.

As regards the enzyme which is classified as an EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on aldehyde group as acceptor with NADH and NADPH as donor, the 3-methylbutanal reductase (EC 1.1.1.265), the alcohol dehydrogenase (EC 1.1.1.1), the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) the same applies as has been set forth above in connection with the methods according to the present invention.

Correspondingly, the present invention furthermore relates to the use
(i) of an organism or microorganism which expresses a combination of an enzyme which is classified as an EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and
   an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or
(ii) of an organism or microorganism which expresses an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2)
for the conversion of 3-methylbutyryl-CoA into isoamyl alcohol.

As regards the enzyme which is classified as an EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on the aldehyde group as acceptor with NADH and NADPH as donor, the 3-methylbutanal reductase (EC 1.1.1.265), the alcohol dehydrogenase (EC 1.1.1.1), the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) as well as the organism or microorganism the same applies as has been set forth above in connection with the methods and/or the organisms or microorganisms according to the present invention.

Furthermore, the present invention relates to the use of a combination comprising
(i) an oxidoreductase acting on a CH—CH group (EC 1.3.-.-) (step 5 as shown in FIG. 2), and
(ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and
   an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or
(iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2);

for the enzymatic conversion of 3-methylcrotonyl-CoA into isoamyl alcohol.

As regards the oxidoreductase acting on a CH—CH group (EC 1.3.-.-), the enzyme which is classified as EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on the aldehyde group as acceptor with NADH and NADPH as donor, the 3-methylbutanal reductase (EC 1.1.1.265), the alcohol dehydrogenase (EC 1.1.1.1) the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) the same applies as has been set forth above in connection with the methods according to the present invention.

In a further preferred embodiment, the present invention relates to the use of a combination comprising (i) an oxidoreductase acting on a CH—CH group (EC 1.3.-.-) (step 5 as shown in FIG. 2), and (ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or (iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2); for the enzymatic conversion of 3-methylcrotonyl-CoA into isoamyl alcohol;
wherein the oxidoreductase acting on a CH—CH group as donor (EC 1.3.-.-) according to (i) is selected from the group consisting of:
(i) an acyl-CoA dehydrogenase (NADP+) (EC 1.3.1.8); (ii) an enoyl-[acyl-carrier-protein] reductase (NADPH, Si-specific) (EC 1.3.1.10); (iii) a cis-2-enoyl-CoA reductase (NADPH) (EC 1.3.1.37); (iv) a trans-2-enoyl-CoA reductase (NADPH) (EC 1.3.1.38); (v) an enoyl-[acyl-carrier-protein] reductase (NADPH, Re-specific) (EC 1.3.1.39); (vi) crotonyl-CoA reductase (EC 1.3.1.86); (vii) an enoyl-[acyl-carrier-protein] reductase (NADH) (EC 1.3.1.9); (viii) a trans-2-enoyl-CoA reductase (NAD$^+$) (EC 1.3.1.44); and (ix) an isovaleryl-CoA dehydrogenase (EC 1.3.8.4). As regards these enzymes, the same applies as has been set forth above in connection with the methods according to the present invention.

Correspondingly, the present invention furthermore relates to the use of an organism or microorganism which expresses a combination comprising
(i) an oxidoreductase acting on a CH—CH group (EC 1.3.-.-) (step 5 as shown in FIG. 2), and
(ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and
an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or
(iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2);
for the enzymatic conversion of 3-methylcrotonyl-CoA into isoamyl alcohol.

As regards the oxidoreductase acting on a CH—CH group (EC 1.3.-.-), the enzyme which is classified as EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on the aldehyde group as acceptor with NADH and NADPH as donor, the 3-methylbutanal reductase (EC 1.1.1.265), the alcohol dehydrogenase (EC 1.1.1.1) the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) the same applies as has been set forth above in connection with the methods, the organisms and microorganisms according to the present invention.

In a further preferred embodiment, the present invention relates to the use of an organism or microorganism which expresses a combination comprising (i) an oxidoreductase acting on a CH—CH group (EC 1.3.-.-) (step 5 as shown in FIG. 2), and (ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or (iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2); for the enzymatic conversion of 3-methylcrotonyl-CoA into isoamyl alcohol;
wherein the oxidoreductase acting on a CH—CH group (EC 1.3.-.-) according to (i) is selected from the group consisting of:
(i) an acyl-CoA dehydrogenase (NADP+) (EC 1.3.1.8); (ii) an enoyl-[acyl-carrier-protein] reductase (NADPH, Si-specific) (EC 1.3.1.10); (iii) a cis-2-enoyl-CoA reductase (NADPH) (EC 1.3.1.37); (iv) a trans-2-enoyl-CoA reductase (NADPH) (EC 1.3.1.38); (v) an enoyl-[acyl-carrier-protein] reductase (NADPH, Re-specific) (EC 1.3.1.39); (vi) crotonyl-CoA reductase (EC 1.3.1.86); (vii) an enoyl-[acyl-carrier-protein] reductase (NADH) (EC 1.3.1.9); (viii) a trans- 2-enoyl-CoA reductase (NAD$^+$) (EC 1.3.1.44); and (ix) an isovaleryl-CoA dehydrogenase (EC 1.3.8.4). As regards these enzymes, the same applies as has been set forth above in connection with the methods, organisms and microorganisms according to the present invention.

In another aspect, the present invention also relates to a composition comprising:

(a) 3-methylbutyryl-CoA; and (b) an enzyme which is classified as EC 1.2.1.- and which is an oxidoreductase acting on the CoA thioester group of acyl-CoA as acceptor with NADH or NADPH as donor (step 6 as shown in FIG. 2) or an organism or microorganism which expresses such an enzyme. In a preferred embodiment, said enzyme is an acetaldehyde dehydrogenase (acetylating) (EC 1.2.1.10) or a propanal dehydrogenase (CoA-propanoylating) (EC 1.2.1.87).

As regards the enzyme which is classified as EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87) and the organism or microorganism the same applies as has been set forth above in connection with the methods and the organisms or microorganisms according to the present invention.

Furthermore, the present invention relates to a composition comprising:

(a) 3-methylbutyryl-CoA; and (b) (i) a combination of an enzyme which is classified as an EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or (ii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2).

As regards the enzyme which is classified as an EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on the aldehyde group as acceptor with NADH and NADPH as donor, the 3-methylbutanal reductase (EC 1.1.1.265), the alcohol dehydrogenase (EC 1.1.1.1), the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) the same applies as has been set forth above in connection with the methods according to the present invention.

Correspondingly, the present invention furthermore relates to a composition comprising:

(a) 3-methylbutyryl-CoA; and (b) (i) an organism or microorganism which expresses a combination of an enzyme which is classified as an EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or (ii) an organism or microorganism which expresses an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2).

As regards the enzyme which is classified as an EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on the aldehyde group as acceptor with NADH and NADPH as donor, the 3-methylbutanal reductase (EC 1.1.1.265), the alcohol dehydrogenase (EC 1.1.1.1), the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) as well as the organism or microorganism the same applies as has been set forth above in connection with the methods and/or the organisms or microorganisms according to the present invention.

Furthermore, the present invention relates to a composition comprising:

(a) 3-methylcrotonyl-CoA; and (b) a combination comprising (i) an oxidoreductase acting on a CH—CH group (EC 1.3.-.-) (step 5 as shown in FIG. 2), and (ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or (iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2).

As regards the oxidoreductase acting on a CH—CH group (EC 1.3.-.-), the enzyme which is classified as EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on the aldehyde group as acceptor with NADH and NADPH as donor, the 3-methylbutanal reductase (EC 1.1.1.265), the alcohol dehydrogenase (EC 1.1.1.1) the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) the same applies as has been set forth above in connection with the methods according to the present invention.

In a further preferred embodiment, the present invention relates to a composition comprising
(a) 3-methylcrotonyl-CoA; and
(b) a combination comprising (i) an oxidoreductase acting on a CH—CH group (EC 1.3.-.-) (step 5 as shown in FIG. 2), and (ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or
(iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2);
wherein the oxidoreductase acting on a CH—CH group (EC 1.3.-.-) according to (i) is selected from the group consisting of (i) an acyl-CoA dehydrogenase (NADP+) (EC 1.3.1.8); (ii) an enoyl-[acyl-carrier-protein] reductase (NADPH, Si-specific) (EC 1.3.1.10); (iii) a cis-2-enoyl-CoA reductase (NADPH) (EC 1.3.1.37); (iv) a trans-2-enoyl-CoA reductase (NADPH) (EC 1.3.1.38); (v) an enoyl-[acyl-carrier-protein] reductase (NADPH, Re-specific) (EC 1.3.1.39); (vi) crotonyl-CoA reductase (EC 1.3.1.86); (vii) an enoyl-[acyl-carrier-protein] reductase (NADH) (EC 1.3.1.9); (viii) a trans-2-enoyl-CoA reductase (NAD$^+$) (EC 1.3.1.44); and (ix) an isovaleryl-CoA dehydrogenase (EC 1.3.8.4). As regards these enzymes, the same applies as has been set forth above in connection with the methods according to the present invention.

Correspondingly, the present invention furthermore relates to a composition comprising:
(a) 3-methylcrotonyl-CoA; and
(b) an organism or microorganism which expresses a combination comprising:
(i) an oxidoreductase acting on a CH—CH group (EC 1.3.-.-) (step 5 as shown in FIG. 2), and
(ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or
(iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2).

As regards the oxidoreductase acting on a CH—CH group (EC 1.3.-.-), the enzyme which is classified as EC 1.2.1.- and which is an oxidoreductase acting on the CoA thioester group of acyl-CoA as acceptor with NADH or NADPH as donor, the acetaldehyde dehydrogenase (acetylating) (EC 1.2.1.10), the propanal dehydrogenase (CoA-propanoylating) (EC 1.2.1.87), the enzyme which is classified as EC 1.1.1.- and which is an oxidoreductase acting on the aldehyde group as acceptor with NADH and NADPH as donor, the 3-methylbutanal reductase (EC 1.1.1.265), the alcohol dehydrogenase (EC 1.1.1.1) the NADP dependent alcohol dehydrogenase (EC 1.1.1.2), the alcohol-forming short chain acyl-CoA dehydrogenase/fatty acyl-CoA reductase and the alcohol-forming fatty acyl-CoA reductase (long-chain acyl-CoA:NADPH reductase) (EC 1.2.1.84) the same applies as has been set forth above in connection with the methods, the organisms and microorganisms according to the present invention.

In a further preferred embodiment, the present invention relates to a composition comprising
(a) 3-methylcrotonyl-CoA; and
(b) an organism or microorganism which expresses a combination comprising (i) an oxidoreductase acting on a CH—CH group (EC 1.3.-.-) (step 5 as shown in FIG. 2), and (ii) a combination of an enzyme which is classified as EC 1.2.1.- and which is an oxidoreductase acting on the CoA thioester group of acyl-CoA as acceptor with NADH or NADPH as donor (step 6 as shown in FIG. 2), preferably an acetaldehyde dehydrogenase (acetylating) (EC 1.2.1.10) or a propanal dehydrogenase (CoA-propanoylating) (EC 1.2.1.87), and an enzyme which is classified as EC 1.1.1.- and which is an oxidoreductase acting on the aldehyde group as acceptor with NADH and NADPH as donor (step 7 as shown in FIG. 2), preferably a 3-methylbutanal reductase (EC 1.1.1.265), an alcohol dehydrogenase (EC 1.1.1.1) or an NADP dependent alcohol dehydrogenase (EC 1.1.1.2), or
(iii) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84) (step 8 as shown in FIG. 2);
wherein the oxidoreductase acting on a CH—CH group (EC 1.3.-.-) according to (i) is selected from the group consisting of (i) an acyl-CoA dehydrogenase (NADP+) (EC 1.3.1.8); (ii) an enoyl-[acyl-carrier-protein] reductase (NADPH, Si-specific) (EC 1.3.1.10); (iii) a cis-2-enoyl-CoA reductase (NADPH) (EC 1.3.1.37); (iv) a trans-2-enoyl-CoA reductase (NADPH) (EC 1.3.1.38); (v) an enoyl-[acyl-carrier-protein] reductase (NADPH, Re-specific) (EC 1.3.1.39); (vi) crotonyl-CoA reductase (EC 1.3.1.86); (vii) an enoyl-[acyl-carrier-protein] reductase (NADH) (EC 1.3.1.9); (viii) a trans-2-enoyl-CoA reductase (NAD$^+$) (EC 1.3.1.44); and (ix) an isovaleryl-CoA dehydrogenase (EC 1.3.8.4). As regards these enzymes, the same applies as has been set forth above in connection with the methods, organisms and microorganisms according to the present invention.

FIG. 1: The natural occurring decarboxylation of an alpha-keto acid (2-keto-isocaproate) into 3-methylbutanal.

FIG. 2: shows an artificial metabolic pathway for isoamyl alcohol (or isoamyl acetate) production from acetyl-CoA via acetoacetyl-CoA, 3-hydroxy-3-methylglutaryl-CoA, 3-methylglutaconyl-CoA, 3-methylbut-2-enoyl-CoA, 3-methylbutyryl-CoA and 3-methylbutyraldehyde or an alternative route for isoamyl alcohol (or isoamyl acetate) production from acetyl-CoA via acetoacetyl-CoA, 3-hydroxy-3-methylglutaryl-CoA, 3-methylglutaconyl-CoA, 3-methylbut-2-enoyl-CoA and 3-methylbutyryl-CoA.

FIG. 3: Schematic reactions for the alternative conversions of 3-methylbutyryl-CoA into isoamyl alcohol.

FIG. 4: Schematic reaction for the reduction of the thioester Coenzyme A of 3-methylbutyryl-CoA into 3-methylbutyraldehyde.

FIG. 5: Schematic reaction for the enzymatic conversion of 3-methylbutyraldehyde (3-methylbutanal) into isoamyl alcohol (3-methylbutanol).

FIG. 6: Schematic reaction for the enzymatic conversion of 3-methylbutyryl-CoA into 3-methylbutanol via 3-methylbutyraldehyde catalyzed by a single enzyme in accordance with step 8 as illustrated in FIG. 2.

FIGS. 7a and 7b:
Schematic reaction for the enzymatic conversion of 3-methylcrotonyl-CoA into 3-methylbutyryl-CoA utilizing NAD(P)H, H$^+$ or FADH$_2$ as a co-factor.

FIG. 8: Schematic reaction for the enzymatic conversion of isoamyl alcohol into isoamyl acetate.

FIG. 9: Schematic reaction for the enzymatic conversion of 3-methylglutaconyl-CoA into 3-methylcrotonyl-CoA.

FIG. 10: Schematic reaction for the enzymatic conversion of 3-hydroxy-3-methylglutaryl-CoA into 3-methylglutaconyl-CoA.

FIG. 11: Schematic reaction of the condensation of acetoacetyl-CoA and acetyl-CoA into 3-hydroxy-3-methylglutaryl-CoA.

FIG. 12: shows schematically possible ways of producing acetoacetyl-CoA from acetyl-CoA, i.e., the reaction of the condensation of two molecules of acetyl-CoA into acetoacetyl-CoA or the reaction of the condensation of one molecule of acetyl-CoA and one molecule of malonyl-CoA into acetoacetyl-CoA and the concomitant release of 002.

Figure 13:
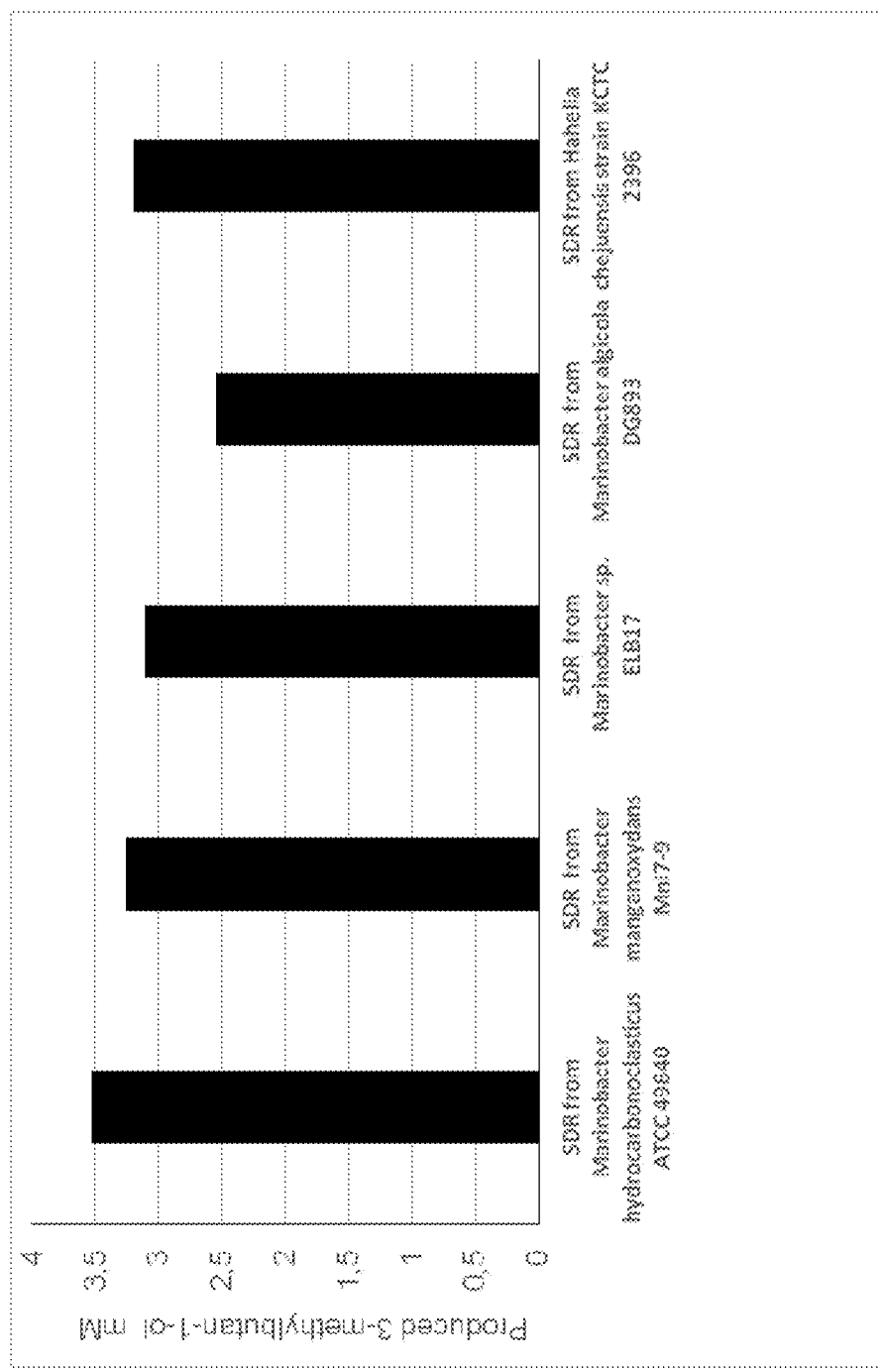

FIG. 13: shows the quantification of 3-methylbutan-1-ol produced via enzymatic reduction of 3-methylbutyryl-CoA catalyzed by different Short chain Dehydrogenase/Reductase (SDR) in the presence of NADPH as co-factor.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Example 1: Cloning, Expression and Purification of Enzymes

Gene synthesis, cloning and expression of recombinant proteins The sequences of the studied enzymes inferred from the genomes of target organisms were generated by oligonucleotide concatenation to fit the codon usage of *E. coli* (genes were commercially synthesized by GeneArt®). A stretch of 6 histidine codons was inserted after the methionine initiation codon so as to provide an affinity tag for purification. The genes thus synthesized were cloned in a pET-25b(+) expression vector (vectors were constructed by GeneArt®).

Competent *E. coli* BL21(DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 6 h at 30° C. and protein expression was continued at 18° C. overnight (approximately 16 h). The cells were collected by centrifugation at 4° C., 10,000 rpm for 20 min and the pellets were stored at −80° C.

Protein Purification and Concentration

The pellets from 500 ml of culture cells were thawed on ice and resuspended in 15 ml of the appropriate buffer solution pH 7.5 (i.e., 50 mM potassium phosphate for the short chain reductase/dehydrogenase or 50 mM Tris-HCl for the propanal dehydrogenase (CoA-propanoylating)), containing 200 mM NaCl, 10 mM MgCl$_2$, 10 mM imidazole and 1 mM DTT. Twenty microliters of lysonase (Novagen) were added. Cells were incubated 10 minutes at room temperature and then returned to ice for 20 minutes. Cell lysis was completed by sonication for 2×15 seconds. The bacterial extracts were then clarified by centrifugation at 4° C., 4000 rpm for 40 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of the above-described respective appropriate buffer solution pH 7.5, yet containing 100 mM NaCl and 250 mM imidazole. Eluates were then concentrated, desalted on Amicon Ultra-4 10 kDa filter unit (Millipore) and enzymes were resuspended in buffers compatible with downstream enzyme activity assay. The purity of proteins thus purified varied from 60% to 90% as estimated by SDS-PAGE analysis. Protein concentrations were determined by direct UV 280 nm measurement on the NanoDrop 1000 spectrophotometer (Thermo Scientific) or by Bradford assay (BioRad).

Example 2: Screening of a Collection of Short Chain Dehydrogenases/Reductases Using 3-Methylbutyryl-CoA as Substrate and NADPH as Cofactor A set of 5 genes encoding representatives of short chain dehydrogenases/reductases across marine bacteria was created and tested for their ability to reduce 3-methylbutyryl-CoA (isovaleryl-CoA) into 3-methylbutan-1-ol (isoamyl alcohol). The genes were synthesized and corresponding enzymes were then produced according to the procedure described in Example 1.

The following set of 5 genes has been tested:
Short chain dehydrogenase/reductase from *Marinobacter hydrocarbonoclasticus* ATCC 49840 (Uniprot accession number H8W980).
Short chain dehydrogenase/reductase from *Marinobacter manganoxydans* Mnl7-9 (Uniprot accession number G6YQS9).
Short chain dehydrogenase/reductase from *Marinobacter* sp. ELB17 (Uniprot accession number A3JCC5).
Short chain dehydrogenase/reductase from *Marinobacter algicola* DG893 (Uniprot accession number A6EUH6).

Short-chain alcohol dehydrogenase-like protein from *Hahella chejuensis* strain KCTC 2396 (Uniprot accession number Q2SCE0).

For the reductase assays, a reaction mixture containing 50 mM potassium phosphate buffer pH 7.5, 20 mM NADPH, 100 mM NaCl, 5 mM 3-methylbutyryl-CoA and 0.5 mg/ml enzyme in a total volume of 150 µl was used and the reactions were carried out at 37° C. for 18 h. According the following procedure, control reactions were performed in which a) no enzyme was added b) no substrate was added, c) no cofactor was added.

The reactions were stopped by adding 50 µl of acetonitrile in the reaction medium. The samples were then centrifuged, filtered through a 0.22 µm filter and the clarified supernatants were transferred into a clean vial for HPLC analysis. Commercial 3-methylbutyraldehyde and 3-methylbutan-1-ol (Sigma-Aldrich) were used as reference.

HPLC analysis was performed using an 1260 Inifinity LC System (Agilent), equipped with column heating module and refractometer detector.

5 µl of each samples were separated on a Hi-Plex H column (Agilent), (50×7.5 mm, 8 µm particle size, column temp. 30° C.) with a mobile phase flow rate of 1 ml/min. The mobile phase consisted of 8.4 mM sulfuric acid in water. Retention time of 3-methylbutan-1-ol under these conditions was 6.85 min.

The results of HPLC analysis for each enzymatic assay are summarized in FIG. 13.

No production of 3-methylbutan-1-ol was observed in control assays. Significant production of 3-methylbutan-1-ol from 3-methylbutyryl-CoA was observed in the enzymatic assays. Therefore, the target enzymes were able to catalyze this conversion.

Example 3: Reduction of 3-Methylbutyryl-CoA into 3-Methylbutyraldehyde Catalyzed by a Propanal Dehydrogenase (CoA-Propanoylating) Using NADH as Cofactor The genes of propanal dehydrogenase (CoA-propanoylating) from *Salmonella typhimurium* (Uniprot accession number H9L4I6) and *Klebsiella pneumonia* (Uniprot accession number A6TDE3) are synthesized and corresponding enzymes are produced according to the procedure described in Example 1.

For the reductase assays, a typical reaction mixture containing 50 mM Tris-HCl pH 7.5, 20 mM NADH, 100 mM NaCl, 5 mM 3-methylbutyryl-CoA and 0.5-1 mg/ml enzyme in a total volume of 200 µl is used and the reactions are carried out at 37° C. for 1 h. Controls are performed in parallel, according to the procedure described in Example 2.

The reactions are stopped by adding 50 µl of acetonitrile to the reaction medium. The samples are then centrifuged, filtered through a 0.22 µm filter and the clarified supernatants are transferred into a clean vial for HPLC analysis. HPLC analysis are conducted according to the method described in Example 2.

The invention claimed is:

1. A method for the production of isoamyl alcohol (3-methylbutan-1-ol) comprising the enzymatic conversion of 3-methylbutyryl-CoA into isoamyl alcohol comprising:

(a) two enzymatic steps comprising (i) first the enzymatic conversion of 3-methylbutyryl-CoA into 3-methylbutyraldehyde by an acetaldehyde dehydrogenase (acetylating) (EC 1.2.1.10) or a propanal dehydrogenase (CoA-propanoylating) (EC 1.2.1.87); and (ii) then enzymatically converting the thus obtained 3-methylbutyraldehyde into said isoamyl alcohol; or (b) a single enzymatic reaction in which 3-methylbutyryl-CoA is directly converted into isoamyl alcohol by using an alcohol-forming short chain acyl-CoA dehydrogenase/fatty acyl-CoA reductase or an alcohol-forming fatty acyl-CoA reductase (long-chain acyl-CoA:Nicotinamide Adenine Dinucleotide Phosphate Hydrogen ("NADPH") reductase) (EC 1.2.1.84).

2. The method of claim 1(a), wherein the enzymatic conversion of said 3-methylbutyraldehyde into said isoamyl alcohol according to (ii) is achieved by using an enzyme which is classified as EC 1.1.1.- and which is an oxidoreductase acting on the aldehyde group as acceptor with Nicotinamide Adenine Dinucleotide, reduced ("NADH") or NADPH as donor.

3. The method of claim 1, further comprising providing the 3-methylbutyryl-CoA by the enzymatic conversion of 3-methylcrotonyl-CoA into said 3-methyl butyryl-CoA.

4. The method of claim 3, wherein the enzymatic conversion of 3-methylcrotonyl-CoA into said 3-methylbutyryl-CoA is achieved by using an enzyme which is classified as EC 1.3.-.- and which is an oxidoreductase acting on a CH—CH group.

5. The method of claim 4, wherein the enzyme is selected from the group consisting of (i) an acyl-CoA dehydrogenase (NADP+) (EC 1.3.1.8);

(ii) an enoyl-[acyl-carrier-protein] reductase (NADPH, Si-specific) (EC 1.3.1.10);

(iii) a cis-2-enoyl-CoA reductase (NADPH) (EC 1.3.1.37);

(iv) a trans-2-enoyl-CoA reductase (NADPH) (EC 1.3.1.38);

(v) an enoyl-[acyl-carrier-protein] reductase (NADPH, Re-specific) (EC 1.3.1.39);

(vi) crotonyl-CoA reductase (EC 1.3.1.86);

(vii) an enoyl-[acyl-carrier-protein] reductase (NADH) (EC 1.3.1.9);

(viii) a trans-2-enoyl-CoA reductase (Nicotinamide Adenine Dinucleotide, oxidized ("NAD+")) (EC 1.3.1.44); and (ix) an isovaleryl-CoA dehydrogenase (EC 1.3.8.4).

6. The method of claim 1, further comprising the enzymatic conversion of isoamyl alcohol into 3-methylbutyl acetate (isoamyl acetate).

7. The method of claim 6, wherein the enzymatic conversion of isoamyl alcohol into 3-methylbutyl acetate (isoamyl acetate) is achieved by using an alcohol-O-acetyltransferase (EC 2.3.1.84).

8. The method of claim 1, wherein said method is carried out in a recombinant microorganism which expresses (i) an acetaldehyde dehydrogenase (acetylating) (EC 1.2.1.10) or a propanal dehydrogenase (CoA-propanoylating) (EC1.2.1.87);

(ii) an enzyme capable of enzymatically converting 3-methylbutyraldehyde into isoamyl alcohol;

(iii) an enzyme capable of enzymatically converting 3-methylglutaconyl-CoA into 3-methylcrotonyl-CoA; and (iv) an enzyme capable of enzymatically converting 3-methylcrotonyl-CoA into 3-methylbutyryl-CoA.

9. The method of claim 8, wherein the enzyme capable of enzymatically converting said 3-methylbutyraldehyde into said isoamyl alcohol is an enzyme which is classified as EC 1.1.1.- and which is an oxidoreductase acting on the aldehyde group as acceptor with NADH or NADPH as donor.

10. The method of claim 8, wherein the enzyme capable of enzymatically converting 3-methylglutaconyl-CoA into 3-methylcrotonyl-CoA is an enzyme which is a 3-methylcrotonyl-CoA carboxylase (EC 6.4.1.4), geranoyl-CoA carboxylase (EC 6.4.1.5) or a glutaconyl-CoA decarboxylase (EC 4.1.1.70).

11. The method of claim 8, wherein the enzyme capable of enzymatically converting 3-methylcrotonyl-CoA into 3-methylbutyryl-CoA according to (iv) is an enzyme which is classified as EC 1.3.-.- and which is an oxidoreductase acting on a CH—CH group.

12. The method of claim 11, wherein the enzyme is selected from the group consisting of
(i) an acyl-CoA dehydrogenase (NADP+) (EC 1.3.1.8);
(ii) an enoyl-[acyl-carrier-protein] reductase (NADPH, Si-specific) (EC 1.3.1.10);
(iii) a cis-2-enoyl-CoA reductase (NADPH) (EC 1.3.1.37);
(iv) a trans-2-enoyl-CoA reductase (NADPH) (EC 1.3.1.38);
(v) an enoyl-[acyl-carrier-protein] reductase (NADPH, Re-specific) (EC 1.3.1.39);
(vi) crotonyl-CoA reductase (EC 1.3.1.86);
(vii) an enoyl-[acyl-carrier-protein] reductase (NADH) (EC 1.3.1.9);
(viii) a trans-2-enoyl-CoA reductase (NAD$^+$) (EC 1.3.1.44); and
(ix) an isovaleryl-CoA dehydrogenase (EC 1.3.8.4).

13. The method of claim 8 which further expresses an enzyme capable of enzymatically converting isoamyl alcohol into 3-methylbutyl acetate (isoamyl acetate).

14. The method of claim 13, wherein the enzyme capable of enzymatically converting isoamyl alcohol into 3-methylbutyl acetate (isoamyl acetate) is an alcohol-O-acetyl-transferase (EC 2.3.1.84).

15. The method of claim 1, wherein said method is carried out in a recombinant microorganism which expresses
(i) an alcohol-forming short chain acyl-CoA dehydrogenase/fatty acyl-CoA reductase or an alcohol-forming fatty acyl-CoA reductase (long-chain acyl-CoA:NADPH reductase) (EC 1.2.1.84); and
(ii) an enzyme capable of enzymatically converting 3-methylcrotonyl-CoA into 3-methylbutyryl-CoA;
(iii) an enzyme capable of enzymatically converting 3-methylglutaconyl-CoA into 3-methylcrotonyl-CoA.

16. The method of claim 15, wherein the enzyme capable of enzymatically converting 3-methylcrotonyl-CoA into 3-methylbutyryl-CoA according to (ii) [step 5] is an enzyme which is classified as EC 1.3.-.- and which is an oxidoreductase acting on a CH—CH group.

17. The method of claim 16, wherein the enzyme is selected from the group consisting of
(i) an acyl-CoA dehydrogenase (NADP+) (EC 1.3.1.8);
(ii) an enoyl-[acyl-carrier-protein] reductase (NADPH, Si-specific) (EC 1.3.1.10);
(iii) a cis-2-enoyl-CoA reductase (NADPH) (EC 1.3.1.37);
(iv) a trans-2-enoyl-CoA reductase (NADPH) (EC 1.3.1.38);
(v) an enoyl-[acyl-carrier-protein] reductase (NADPH, Re-specific) (EC 1.3.1.39);
(vi) crotonyl-CoA reductase (EC 1.3.1.86);
(vii) an enoyl-[acyl-carrier-protein] reductase (NADH) (EC 1.3.1.9);
(viii) a trans-2-enoyl-CoA reductase (NAD$^+$) (EC 1.3.1.44); and
(ix) an isovaleryl-CoA dehydrogenase (EC 1.3.8.4).

18. The method of claim 15, wherein the enzyme capable of enzymatically converting 3-methylglutaconyl-CoA into 3-methylcrotonyl-CoA according to (iii) is an enzyme which is a 3-methylcrotonyl-CoA carboxylase (EC 6.4.1.4), geranoyl-CoA carboxylase (EC 6.4.1.5) or a glutaconyl-CoA decarboxylase (EC 4.1.1.70).

19. The method of claim 15 which further expresses an enzyme capable of enzymatically converting isoamyl alcohol into 3-methylbutyl acetate (isoamyl acetate).

20. The method of claim 19, wherein the enzyme capable of enzymatically converting isoamyl alcohol into 3-methylbutyl acetate (isoamyl acetate) is an alcohol-O-acetyl-transferase (EC 2.3.1.84).

21. The method of claim 8, wherein the recombinant microorganism is *E. coli* or yeast.

22. The method of claim 9, wherein the recombinant microorganism is *E. coli* or a yeast.

23. The method of claim 10, wherein the recombinant microorganism is *E. coli* or a yeast.

24. The method of claim 11, wherein the recombinant microorganism is *E. coli* or a yeast.

25. The method of claim 12, wherein the recombinant microorganism is *E. coli* or a yeast.

26. The method of claim 13, wherein the recombinant microorganism is *E. coli* or a yeast.

27. The method of claim 14, wherein the recombinant microorganism is *E. coli* or a yeast.

28. The method of claim 15, wherein the recombinant microorganism is *E. coli* or a yeast.

29. The method of claim 16, wherein the recombinant microorganism is *E. coli* or a yeast.

30. The method of claim 17, wherein the recombinant microorganism is *E. coli* or a yeast.

31. The method of claim 18, wherein the recombinant microorganism is *E. coli* or a yeast.

32. The method of claim 19, wherein the recombinant microorganism is *E. coli* or a yeast.

33. The method of claim 20, wherein the recombinant microorganism is *E. coli* or a yeast.

* * * * *